(12) United States Patent
Cuevas-Cordobés et al.

(10) Patent No.: US 10,745,361 B2
(45) Date of Patent: Aug. 18, 2020

(54) PIPERAZINE DERIVATIVES HAVING MULTIMODAL ACTIVITY AGAINST PAIN

(71) Applicant: ESTEVE PHARMACEUTICALS, S.A., Barcelona (ES)

(72) Inventors: Félix Cuevas-Cordobés, Valdemoro (ES); Carmen Almansa-Rosales, Barcelona (ES); Monica Garcia-Lopez, Barcelona (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 0 days.

(21) Appl. No.: 16/426,024

(22) Filed: May 30, 2019

(65) Prior Publication Data

US 2019/0276415 A1    Sep. 12, 2019

Related U.S. Application Data

(63) Continuation of application No. 15/106,423, filed as application No. PCT/EP2014/078852 on Dec. 19, 2014, now Pat. No. 10,351,535.

(30) Foreign Application Priority Data

Dec. 20, 2013 (EP) ..................... 13384006

(51) Int. Cl.

| | |
|---|---|
| *A61P 25/04* | (2006.01) |
| *A61K 31/4155* | (2006.01) |
| *A61K 31/4178* | (2006.01) |
| *A61K 31/4192* | (2006.01) |
| *A61K 31/4196* | (2006.01) |
| *A61K 31/4439* | (2006.01) |
| *A61K 31/407* | (2006.01) |
| *C07D 487/04* | (2006.01) |
| *C07D 249/06* | (2006.01) |
| *C07D 401/14* | (2006.01) |
| *C07D 231/12* | (2006.01) |
| *C07D 233/64* | (2006.01) |
| *C07D 401/04* | (2006.01) |
| *C07D 403/06* | (2006.01) |
| *C07D 249/04* | (2006.01) |
| *C07D 487/08* | (2006.01) |
| *C07D 401/06* | (2006.01) |
| *C07D 401/12* | (2006.01) |

(52) U.S. Cl.
CPC ......... *C07D 249/06* (2013.01); *C07D 231/12* (2013.01); *C07D 233/64* (2013.01); *C07D 249/04* (2013.01); *C07D 401/04* (2013.01); *C07D 401/06* (2013.01); *C07D 401/12* (2013.01); *C07D 401/14* (2013.01); *C07D 403/06* (2013.01); *C07D 487/04* (2013.01); *C07D 487/08* (2013.01)

(58) Field of Classification Search
CPC . A61P 25/04; A61K 31/4155; A61K 31/4178; A61K 31/4192; A61K 31/4196; A61K 31/4439; A61K 31/407; C07D 487/04
See application file for complete search history.

(56) References Cited

U.S. PATENT DOCUMENTS

| | | |
|---|---|---|
| 4,711,885 A | 12/1987 | Wierzbicki et al. |
| 8,288,373 B2 | 10/2012 | Chen et al. |
| 8,853,202 B2 | 10/2014 | Chen et al. |
| 2004/0267016 A1 | 12/2004 | Tucker |
| 2010/0075976 A1 | 3/2010 | Cohen et al. |
| 2010/0184759 A1 | 7/2010 | Wünsch et al. |
| 2013/0064770 A1 | 3/2013 | Newington et al. |
| 2013/0158029 A1 | 6/2013 | Lopez et al. |

FOREIGN PATENT DOCUMENTS

| | | |
|---|---|---|
| CA | 2683461 | 10/2008 |
| EP | 0199641 | 10/1986 |
| EP | 0241053 | 10/1987 |
| EP | 1982714 | 10/2008 |
| EP | 2009005 | 12/2008 |
| EP | 2078003 | 7/2009 |
| EP | 2395003 | 12/2011 |

(Continued)

OTHER PUBLICATIONS

Boechat, Nubia, et al., "Novel 1,2,3-Triazole Derivatives for Use against *Mycobacterium tuberculosis* H37Rv (ATCC 27294) Strain", J. Med. Chem., 2011, 54, 5988-5999.

(Continued)

*Primary Examiner* — Brenda L Coleman
(74) *Attorney, Agent, or Firm* — Hueschen and Sage

(57) ABSTRACT

The present invention relates to compounds having dual pharmacological activity towards both the sigma (σ) receptor, and the μ-opiod receptor and more particularly to piperazine compounds having this pharmacological activity, to processes of preparation of such compounds, to pharmaceutical compositions comprising them, and to their use in therapy, in particular for the treatment of pain.

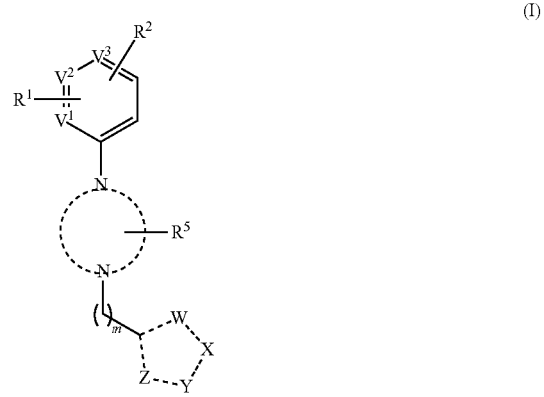

13 Claims, No Drawings

(56) References Cited

FOREIGN PATENT DOCUMENTS

| WO | WO2004011441 | 2/2004 |
|---|---|---|
| WO | WO 2008/008480 | 1/2008 |
| WO | WO2008011611 | 1/2008 |
| WO | WO 2008/054702 | 5/2008 |
| WO | WO 2008/077552 | 7/2008 |
| WO | WO 2008/141020 | 11/2008 |
| WO | WO2008157844 | 12/2008 |
| WO | WO2009027820 | 3/2009 |
| WO | WO2010046780 | 4/2010 |
| WO | WO 2010/054006 | 5/2010 |
| WO | WO2010080864 | 7/2010 |
| WO | WO2011098904 | 8/2011 |

OTHER PUBLICATIONS

Bornot, A, et al., "Systematic Exploration of Dual-Acting Modulators from a Combined Medicinal Chemistry and Biology Perspective." J. Med Chem, 56, 1197-1210 (2013).

Brotherton, Wendy, S., et al., "Apparent Copper(II)-Accelerated Azide-Alkyne Cycloaddition", Organic Letters, 2009, vol. 11, No. 21, pp. 4954-4957.

Chattopadhyay, B., et al., "Fused Tetrazoles as Azide Surrogates in Click Reaction: Efficient Synthesis of N-Heterocycle-Substituted 1,2,3-Triazoles", Organic Letters, 2010, vol. 12, No. 9, 2166-2169.

Chien, et al., "Sigma antagonists potentiate opioid analgesia in rats", Neuroscience Letters, 1995, 190, 137-139.

Dickenson, A.H., Suzuki, R., "Opioids in neuropathic pain: clues from animal studies." Eur J Pain 9, 113-116 (2005).

Goldberg, et al., "Pain as a global public health priority", BMC Public Health. 11, 770 (2011).

International Search Report for International Application No. PCT/EP2014/078852, dated Jan. 26, 2015.

Kuang, Gui-Chao, et al.,"Chelation-Assisted, Copper(II)-Acetate-Accelerated Azide-Alkyne Cycloaddition", J. Org. Chem., 2010, 75, 6540-6548.

Liu, Yuxiu, et al., "Efficient Synthesis of N-2-Aryl-1,2,3-Triazole Fluorophores via Post-Triazole Arylation", Organic Letters, 2008, vol. 10, No. 23, 5389-5392.

Mao, J, et al., "Combination Drug Therapy for Chronic Pain: A Call for More Clinical Studies." J. Pain 12, 157-166 (2011).

Matsumoto, K., et al., "A New Synthesis of 1-Aryl-1H-1,2,4-Triazole-3-carboxylic Acid Esters", Synthesis, 1975, 9, 609-610.

Ou, et al., Molecular Diversity, 2011, 15, 927-946.

Turk, DC, et al., "Treatment of chronic non-cancer pain", Lancet 377, 2226-2235 (2011).

Whiting, et al., "S1 Supporting Information for Rapid Discovery and Structure Activity Profiling of Novel Inhibitors of HIV-1 Protease Enabled by the Copper(I)-Catalyzed Synthesis of 1,2,3-Triazoles and Their Further Functionalization," Nov. 30, 2005.

Yan, Ze-Yi, et al., "General synthesis of (1-substituted-1H-1,2,3-triazol-4-ylmethyl)-dialkylamines via a copper(I)-catalyzed three-component reaction in water". Tetrahedron, 2005, 61, 9331-9337.

Zamanillo, D., et al., "Sigma 1 receptor: A new therapeutic target for pain", Eur. J. Pharmacol, 716, 78-93 (2013).

Nagesh, Hunsur Nagenra, et al., "Design, synthesis and evaluation of 6-(4-((substituted-1H-1,2,3-triazol-4-yl)methyl)piperazin-1-yl)phenanthridine analogues as antimycobacterial agents", Bioorganic & Medicinal Chemistry Letters, 23, 2013, 6803-6810.

Neves, Gilda, et al., "Searching for multi-target antipsychotics: discovery of orally active heterocyclic N-phenylpiperazine ligands of D2-like and 5-HT1A receptors", Bioorganic & Medicinal Chemistry, 18, 2010, pp. 1925-1935.

Pazini, Francine, et al., "Design of new dopamine D2 receptor ligands: biosynthesis and pharmacological evaluation of the hydroxylated metabolite of LASSBio-581", Bioorganic & Medicinal Chemistry Letters, 20, 2010, pp. 2888-2891.

Van Wijngaarden, Ineke, et al., "2-phenylpyrroles as conformationally restricted benzamide analogues. A new class of potential antipsychotics", J. Med. Chem., 31, 1988, pp. 1934-1940.

PIPERAZINE DERIVATIVES HAVING MULTIMODAL ACTIVITY AGAINST PAIN

FIELD OF THE INVENTION

The present invention relates to compounds having dual pharmacological activity towards both the sigma (σ) receptor, and the μ-opiod receptor (MOR or mu-opioid) and more particularly to piperidine compounds having this pharmacological activity, to processes of preparation of such compounds, to pharmaceutical compositions comprising them, and to their use in therapy, in particular for the treatment of pain.

BACKGROUND OF THE INVENTION

The adequate management of pain constitutes an important challenge, since currently available treatments provide in many cases only modest improvements, leaving many patients unrelieved [Turk D C, Wilson H D, Cahana A. Treatment of chronic non-cancer pain. Lancet 377, 2226-2235 (2011)]. Pain affects a big portion of the population with an estimated prevalence of around 20% and its incidence, particularly in the case of chronic pain, is increasing due to the population ageing. Additionally, pain is clearly related to comorbidities, such as depression, anxiety and insomnia, which lead to important productivity losses and socio-economical burden [Goldberg D S, McGee S J. Pain as a global public health priority. BMC Public Health. 11, 770 (2011)]. Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

As mentioned before, there are few available therapeutic classes for the treatment of pain, and opioids are among the most effective, especially when addressing severe pain states. They act through three different types of opioid receptors (mu, kappa and gamma) which are transmembrane G-protein coupled receptors (GPCRs). Still, the main analgesic action is attributed to the activation of the p-opioid receptor (MOR). However, the general administration of MOR agonists is limited due to their important side effects, such as constipation, respiratory depression, tolerance, emesis and physical dependence [Meldrum, M. L. (Ed.). Opioids and Pain Relief: A Historical Perspective. Progress in Pain Research and Management, Vol 25. IASP Press, Seattle, 2003]. Additionally, MOR agonists are not optimal for the treatment of chronic pain as indicated by the diminished effectiveness of morphine against chronic pain conditions. This is especially proven for the chronic pain conditions of neuropathic or inflammatory origin, in comparison to its high potency against acute pain. The finding that chronic pain can lead to MOR down-regulation may offer a molecular basis for the relative lack of efficacy of morphine in long-term treatment settings [Dickenson, A. H., Suzuki, R. Opioids in neuropathic pain: Clues from animal studies. Eur J Pain 9, 113-6 (2005)]. Moreover, prolonged treatment with morphine may result in tolerance to its analgesic effects, most likely due to treatment-induced MOR down-regulation, internalization and other regulatory mechanisms. As a consequence, long-term treatment can result in substantial increases in dosing in order to maintain a clinically satisfactory pain relief, but the narrow therapeutic window of MOR agonists finally results in unacceptable side effects and poor patient compliance.

The sigma-1 ($\sigma_1$) receptor was discovered 35 years ago and initially assigned to a new subtype of the opioid family, but later on and based on the studies of the enantiomers of SKF-10,047, its independent nature was established. The first link of the $\sigma_1$ receptor to analgesia was established by Chien and Pasternak [Chien C C, Pasternak G W. Sigma antagonists potentiate opioid analgesia in rats. Neurosci. Lett. 190, 137-9 (1995)], who described it as an endogenous anti-opioid system, based on the finding that $\sigma_1$ receptor agonists counteracted opioid receptor mediated analgesia, while $\sigma_1$ receptor antagonists, such as haloperidol, potentiated it.

Many additional preclinical evidences have indicated a clear role of the $\sigma_1$ receptor in the treatment of pain [Zamanillo D, Romero L, Merlos M, Vela J M. Sigma 1 receptor: A new therapeutic target for pain. Eur. J. Pharmacol, 716, 78-93 (2013)]. The development of the $\sigma_1$ receptor knockout mice, which show no obvious phenotype and perceive normally sensory stimuli, was a key milestone in this endeavour. In physiological conditions the responses of the $\sigma_1$ receptor knockout mice to mechanical and thermal stimuli were found to be undistinguishable from WT ones but they were shown to possess a much higher resistance to develop pain behaviours than WT mice when hypersensitivity entered into play. Hence, in the $\sigma_1$ receptor knockout mice capsaicin did not induce mechanical hypersensitivity, both phases of formalin-induced pain were reduced, and cold and mechanical hypersensitivity were strongly attenuated after partial sciatic nerve ligation or after treatment with paclitaxel, which are models of neuropathic pain. Many of these actions were confirmed by the use of $\sigma_1$ receptor antagonists and led to the advancement of one compound, S1RA, into clinical trials for the treatment of different pain states. Compound S1RA exerted a substantial reduction of neuropathic pain and anhedonic state following nerve injury (i.e., neuropathic pain conditions) and, as demonstrated in an operant self-administration model, the nerve-injured mice, but not sham-operated mice, acquired the operant responding to obtain it (presumably to get pain relief), indicating that $\sigma_1$ receptor antagonism relieves neuropathic pain and also address some of the comorbidities (i.e., anhedonia, a core symptom in depression) related to pain states.

Pain is multimodal in nature, since in nearly all pain states several mediators, signaling pathways and molecular mechanisms are implicated. Consequently, monomodal therapies fail to provide complete pain relief. Currently, combining existing therapies is a common clinical practice and many efforts are directed to assess the best combination of available drugs in clinical studies [Mao J, Gold M S, Backonja M. Combination drug therapy for chronic pain: a call for more clinical studies. J. Pain 12, 157-166 (2011)]. Hence, there is an urgent need for innovative therapeutics to address this unmet medical need.

As mentioned previously, opioids are among the most potent analgesics but they are also responsible for various adverse effects which seriously limit their use.

Accordingly, there is still a need to find compounds that have an alternative or improved pharmacological activity in the treatment of pain, being both effective and showing the desired selectivity, and having good "drugability" properties, i.e. good pharmaceutical properties related to administration, distribution, metabolism and excretion.

Thus, the technical problem can therefore be formulated as finding compounds that have an alternative or improved pharmacological activity in the treatment of pain.

In view of the existing results of the currently available therapies and clinical practices, the present invention offers a solution by combining in a single compound binding as a ligand to two different receptors relevant for the treatment of pain. This was mainly achieved by providing the compound according to the invention that bind both to the µ-opiod receptor and to the $\sigma_1$ receptor.

SUMMARY OF THE INVENTION

In this invention a family of structurally distinct piperazine derivatives which have a dual pharmacological activity towards both the sigma (σ) receptor, and the µ-opiod receptor was identified thus solving the above problem of identifying alternative or improved pain treatments by offering such dual compounds.

The invention is in one aspect directed to a compound having a dual activity binding to the $\sigma_1$ receptor and the µ-opioid receptor for use in the treatment of pain.

As this invention is aimed at providing a compound or a chemically related series of compounds which act as dual ligands of the $\sigma_1$ receptor and the µ-opioid receptor it is a very preferred embodiment if the compound has a binding expressed as $K_i$ which is <100 nm for both receptors, the µ-opioid receptor and the $\sigma_1$ receptor.

The invention is directed in a main aspect to a compound of general formula (I),

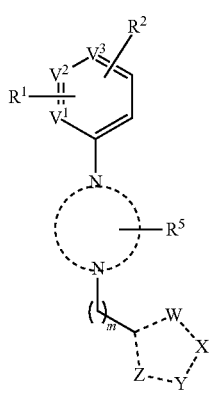

(I)

wherein $R^1$, $R^2$, $R^5$, $V^1$, $V^2$, $V^3$, W, X, Y, Z and m are as defined below in the detailed description.

DETAILED DESCRIPTION OF THE INVENTION

The invention is directed to a family of structurally distinct piperazine derivatives which have a dual pharmacological activity towards both the sigma (σ) receptor, and the µ-opiod receptor was identified thus solving the above problem of identifying alternative or improved pain treatments by offering such dual compounds.

The invention is in one aspect directed to a compound having a dual activity binding to the $\sigma_1$ receptor and the µ-opioid receptor for use in the treatment of pain.

As this invention is aimed at providing a compound or a chemically related series of compounds which act as dual ligands of the $\sigma_1$ receptor and the µ-opioid receptor it is a very preferred embodiment if the compound has a binding expressed as $K_i$ which is <100 nm for both receptors, the µ-opioid receptor and the $\sigma_1$ receptor.

The applicant has surprisingly found that the problem on which the present invention is based can be solved by using a multimodal balanced analgesic approach combining two different synergistic activities in a single drug (i.e., dual ligands which are bifunctional and bind to MOR and to $\sigma_1$ receptor), thereby enhancing the opioid analgesia through the $\sigma_1$ activation without increasing the undesirable side effects. This supports the therapeutic value of a dual MOR/$\sigma_1$ receptor compound whereby the $\sigma_1$ receptor binding component acts as an intrinsic adjuvant of the MOR binding component.

This solution offered the advantage that the two mechanisms complement each other in order to treat pain and chronic pain using lower and better tolerated doses needed based on the potentiation of analgesia but avoiding the adverse events of p opioid receptor agonists.

A dual compound that possess binding to both the µ-opiod receptor and to the $\sigma_1$ receptor shows a highly valuable therapeutic potential by achieving an outstanding analgesia (enhanced in respect to the potency of the opioid component alone) with a reduced side-effect profile (safety margin increased compared to that of the opioid component alone) versus existing opiod therapies.

Advantageously, the dual compounds according to the present invention would in addition show one or more the following functionalities: $\sigma_1$ receptor antagonism and MOR agonism. It has to be noted, though, that both functionalities "antagonism" and "agonism" are also sub-divided in their effect into subfunctionalities like partial agonism or inverse agonism. Accordingly, the functionalities of the dual compound should be considered within a relatively broad bandwidth.

An antagonist on one of the named receptors blocks or dampens agonist-mediated responses. Known subfunctionalities are neutral antagonists or inverse agonists.

An agonist on one of the named receptors increases the activity of the receptor above its basal level. Known subfunctionalities are full agonists, or partial agonists.

In addition, the two mechanisms complement each other since MOR agonists are only marginally effective in the treatment of neuropathic pain, while $\sigma_1$ receptor antagonists show outstanding effects in preclinical neuropathic pain models. Thus, the $\sigma_1$ receptor component adds unique analgesic actions in opioid-resistant pain. Finally, the dual approach has clear advantages over MOR agonists in the treatment of chronic pain as lower and better tolerated doses would be needed based on the potentiation of analgesia but not of the adverse events of MOR agonists.

A further advantage of using designed multiple ligands is a lower risk of drug-drug interactions compared to cocktails or multi-component drugs, thus involving simpler pharmacokinetics and less variability among patients. Additionally, this approach may improve patient compliance and broaden the therapeutic application in relation to monomechanistic drugs, by addressing more complex aetiologies. It is also seen as a way of improving the R&D output obtained using the "one drug-one target" approach, which has been questioned over the last years [Bornot A, Bauer U, Brown A, Firth M, Hellawell C, Engkvist O. Systematic Exploration of Dual-Acting Modulators from a Combined Medicinal Chemistry and Biology Perspective. *J. Med. Chem*, 56, 1197-1210 (2013)].

In a particular aspect, the present invention is directed to compounds of general formula (I):

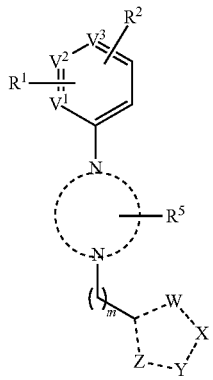 (I)

wherein
m is 1 or 2;
one of $V^1$, $V^2$ and $V^3$ is selected from nitrogen or carbon while the other two are carbon;
$R^1$ is hydroxyl, —$NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl and substituted or unsubstituted heterocyclyl; $R^2$ is hydrogen, halogen (F, Cl, I, Br), —$NR^6R^7$, —$SR^6$, —$OR^6$, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl;
or
$R^1$ and $R^2$ are bonded to neighbouring atoms in the ring and together with these atoms form a saturated or unsaturated, substituted or unsubstituted ring, fused to the ring

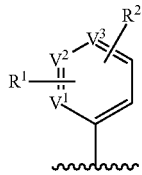

of the corestructure of formula I, which may be condensed with a further unsubstituted or substituted ring system;
$R^5$ is hydrogen, hydroxy or $CH_3$;
$R^6$, $R^7$ and $R^8$ are independent from each other and selected from the group formed by hydrogen, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom may form a cycloalkylic or heterocyclic 4 to 7-membered ring;
and wherein W, X, Y and Z are selected from carbon, nitrogen, or oxygen while W—X—Y—Z are forming together with the bridging C-atom, that is connected to the core scaffold, a 5-membered heterocyclic ring, which is substituted on one of W, X, Y or Z by

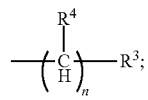

wherein
n is 0 or 1;
$R^3$ is substituted or unsubstituted alkyl, $CONR^6R^7$, substituted or unsubstituted cycloalkyl, substituted or unsubstituted alkenyl, substituted or unsubstituted alkynyl, substituted or unsubstituted aryl and substituted or unsubstituted heterocyclyl;
$R^4$ is hydrogen, substituted or unsubstituted alkyl, substituted of unsubstituted cycloalkyl, substituted or unsubstituted alkenyl, substituted or unsubstituted alkynyl, substituted of unsubstituted aryl and substituted of unsubstituted heterocyclyl;
and wherein

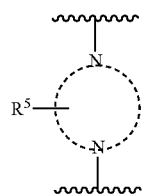

is selected from

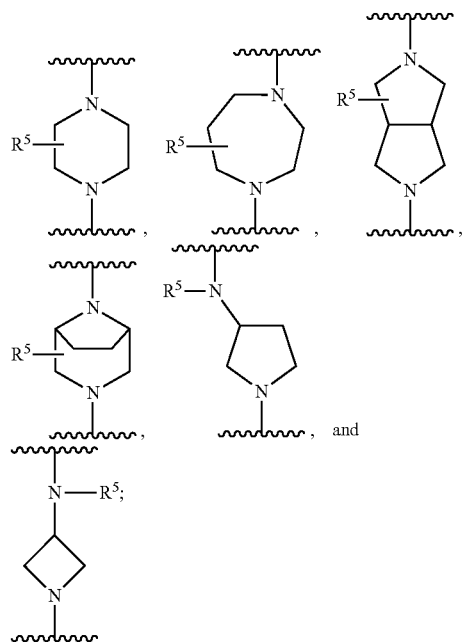

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.
In another embodiment the compound according to the invention—especially according to general formula (I)—is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt therefore a corresponding solvate thereof.

In another embodiment the compound according to the invention—especially according to general formula (I)—is optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In another embodiment the compound according to the invention—especially according to general formula (I)—is optionally in form of one of the stereoisomers, preferably enantiomers or diastereomers, a racemate or in form of a mixture of at least two of the stereoisomers, preferably enantiomers and/or diastereomers, in any mixing ratio.

In one embodiment one or more of the following provisos are applying:

with the proviso that if $V^1$, $V^2$ and $V^3$ are carbon and one of W, X, Y or Z is

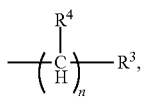

then $R^2$ may not be —OCH$_3$ in meta position;
and/or
with the proviso that if $V^1$, $V^2$ and $V^3$ are carbon, n is 0 and $R^3$ is —CH$_3$ or —C$_2$H$_5$, then neither $R^1$ nor $R^2$ may be —NH$_2$ in meta position;
and/or
with the proviso that if n is 0, $R^3$ may not be alkyl;
and/or
with the proviso that the compound may not be Benzenamine, 3-[4-[2-(3-methyl-5-isoxazolyl)ethyl]-1-piperazinyl];
and/or
with the proviso that the compound may not be Benzenamine, 3-[4-[(1-methyl-1H-pyrazol-4-yl)methyl]-1-piperazinyl];
and/or
with the proviso that the compound may not be Benzenamine, 3-[4-[(1-ethyl-1H-pyrazol-4-yl)methyl]-1-piperazinyl].

In one embodiment the following substituents are preferred:

wherein said aryl or heterocyclyl in $R^1$, and/or said cycloalkyl, aryl or heterocyclyl in $R^2$, or said ring formed by $R^1$ and $R^2$ or the ring condensed to it, if substituted, is substituted with one or more substituents selected from halogen, —$R^9$, —$OR^9$, —$NO_2$, —$NR^9R^{9'}$, $NR^9C(O)R^{9'}$, —$NR^9S(O)_2R^{9'}$, —$S(O)_2NR^9R^{9'}$, —$NR^9C(O)NR^{9'}R^{9''}$, —$SR^9$, —$S(O)R^9$, $S(O)_2R^9$, —CN, haloalkyl, haloalkoxy, —$C(O)OR^9$, —$C(O)NR^9R^{9'}$, —$OCH_2CH_2OH$, —$NR^9S(O)_2NR^{9'}R^{9''}$ and $C(CH_3)_2OR^9$;

wherein said alkyl, alkenyl or alkynyl in $R^2$, if substituted, is substituted with one or more substituents selected from —$OR^9$, halogen, —CN, haloalkyl, haloalkoxy, —$NR^9R^{9'''}$, —$SR^9$, —$S(O)R^9$, and —$S(O)_2R^9$;

wherein $R^9$, $R^{9'}$ and $R^{9''}$ are independently selected from hydrogen, unsubstituted $C_{1-6}$ alkyl, unsubstituted $C_{2-6}$ alkenyl, unsubstituted $C_{2-6}$ alkynyl;

and wherein $R^{9'''}$ is selected from hydrogen, unsubstituted $C_{1-6}$ alkyl, unsubstituted $C_{2-6}$ alkenyl, unsubstituted $C_{2-6}$ alkynyl and -Boc;

wherein said cycloalkyl, aryl or heterocyclyl in $R^6$, in $R^7$, and/or in $R^8$, if substituted, is substituted with one or more substituents selected from halogen, —$R^{10}$, —$OR^{10}$, —$NO_2$, —$NR^{10}R^{10'''}$, $NR^{10}C(O)R^{10'}$, —$NR^{10}S(O)_2R^{10'}$, —$S(O)_2NR^{10}R^{10'}$, —$NR^{10}C(O)NR^{10'}R^{10''}$, —$SR^{10}$, —$S(O)R^{10}$, $S(O)_2R^{10}$, —CN, haloalkyl, haloalkoxy, —$C(O)OR^{10}$, —$C(O)NR^{10}R^{10'}$, —$OCH_2CH_2OH$, $NR^{10}S(O)_2NR^{10'}R^{10''}$ and $C(CH_3)_2OR^{10}$;

wherein said alkyl, alkenyl, or alkynyl in $R^6$, in $R^7$, ad/or in $R^8$, if substituted, is substituted with one or more substituents selected from —$OR^{10}$, halogen, —CN, haloalkyl, haloalkoxy, —$NR^{10}R^{10'''}$, —$SR^{10}$, —$S(O)R^{10}$, and —$S(O)_2R^{10}$;

wherein $R^{10}$, $R^{10'}$ and $R^{10''}$ are independently selected from hydrogen, unsubstituted $C_{1-6}$ alkyl, unsubstituted $C_{2-6}$ alkenyl, unsubstituted $C_{2-6}$ alkynyl;

and wherein $R^{10'''}$ is selected from hydrogen, unsubstituted $C_{1-6}$ alkyl, unsubstituted $C_{2-6}$ alkenyl, unsubstituted $C_{2-6}$ alkynyl and -Boc;

wherein said cycloalkyl, aryl or heterocyclyl in $R^3$ and/or in $R^4$, if substituted, is substituted with one or more substituents selected from halogen, —$R^{11}$, —$OR^{11}$, —$NO_2$, —$NR^{11}R^{11'''}$, $NR^{11}C(O)R^{11'}$, —$NR^{11}S(O)_2R^{11'}$, —$S(O)_2NR^{11}R^{11'}$, $NR^{11}C(O)NR^{11'}R^{11''}$, —$SR^{11}$, —$S(O)R^{11}$, $S(O)_2R^{11}$, —CN, haloalkyl, haloalkoxy, —$C(O)OR^{11}$, —$C(O)NR^{11}R^{11'}$, —$OCH_2CH_2OH$, —$NR^{11}S(O)_2NR^{11'}R^{11''}$ and $C(CH_3)_2OR^{11}$;

wherein said alkyl, alkenyl, or alkynyl in $R^3$ and/or in $R^4$, if substituted, is substituted with one or more substituents selected from —$OR^{11}$, halogen, —CN, haloalkyl, haloalkoxy, —$NR^{11}R^{11'''}$, —$SR^{11}$, —$S(O)R^{11}$, and —$S(O)_2R^{11}$;

wherein $R^{11}$, $R^{11'}$ and $R^{11''}$ are independently selected from hydrogen, unsubstituted $C_{1-6}$ alkyl, unsubstituted $C_{2-6}$ alkenyl, unsubstituted $C_{2-6}$ alkynyl;

and wherein $R^{11'''}$ is selected from hydrogen, unsubstituted $C_{1-6}$ alkyl, unsubstituted $C_{2-6}$ alkenyl, unsubstituted $C_{2-6}$ alkynyl and -Boc.

In one other embodiment the following substituents are preferred:

wherein said aryl or heterocyclyl in $R^1$, and/or said cycloalkyl, aryl or heterocyclyl in $R^2$, or said ring formed by $R^1$ and $R^2$ or the ring condensed to it, if substituted, is substituted with one or more substituents selected from OH, SH, =O, halogen (F, Cl, Br, I), CN, $NO_2$, COOH, $R_z$, O—$R_z$, S—$R_z$, —C(O)—$R_z$, —C(O)—O—$R_z$, $NR_xR_y$; a substituted or unsubstituted aryl or alkyl-aryl; a substituted or unsubstituted cycloalkyl or alkyl-cycloalkyl; a substituted or unsubstituted heterocyclyl or alkyl-heterocyclyl;

wherein said alkyl, alkenyl or alkynyl in $R^2$, if substituted, is substituted with one or more substituents selected from F, Cl, Br, I, $NH_2$, SH or OH, —C(O)OH, or —$OC_{1-4}$alkyl being unsubstituted or substituted by one or more of OH or halogen (F, Cl, I, Br);

wherein $R_z$ is selected from saturated or unsaturated, linear or branched, substituted or unsubstituted $C_{1-6}$ alkyl, unsubstituted $C_{2-6}$ alkenyl, unsubstituted $C_{2-6}$ alkynyl;

with $R_x$ and $R_y$ independently being either H or a saturated or unsaturated, linear or branched, substituted or unsubstituted $C_{1-6}$-alkyl;

wherein said cycloalkyl, aryl or heterocyclyl in $R^6$, in $R^7$, and/or in $R^8$, if substituted, is substituted with one or more substituents selected from OH, SH, =O, halogen (F, Cl, Br, I), CN, $NO_2$, COOH, $R_z$, O—$R_z$, S—$R_z$, —C(O)—$R_z$, —C(O)—O—$R_z$, $NR_xR_y$; a substituted or unsubstituted aryl or alkyl-aryl; a substituted or unsubstituted cycloalkyl or alkyl-cycloalkyl; a substituted or unsubstituted heterocyclyl or alkyl-heterocyclyl;

wherein said alkyl, alkenyl or alkynyl in $R^6$, in $R^7$, and/or in $R^8$, if substituted, is substituted with one or more substituents selected from F, Cl, Br, I, $NH_2$, SH or OH, —C(O)OH, or —$OC_{1-4}$alkyl being unsubstituted or substituted by one or more of OH or halogen (F, Cl, I, Br);

wherein $R_z$ is selected from saturated or unsaturated, linear or branched, substituted or unsubstituted $C_{1-6}$ alkyl, unsubstituted $C_{2-6}$ alkenyl, unsubstituted $C_{2-6}$ alkynyl;

with $R_x$ and $R_y$ independently being either H or a saturated or unsaturated, linear or branched, substituted or unsubstituted $C_{1-6}$-alkyl;

wherein said cycloalkyl, aryl or heterocyclyl in $R^3$ and/or in $R^4$, if substituted, is substituted with one or more substituents selected from OH, SH, =O, halogen (F, Cl, Br, I), CN, $NO_2$, COOH, $R_z$, O—$R_z$, S—$R_z$, —C(O)—$R_z$, —C(O)—O—$R_z$, $NR_xR_y$; a substituted or unsubstituted aryl or alkyl-aryl; a substituted or unsubstituted cycloalkyl or alkyl-cycloalkyl; a substituted or unsubstituted heterocyclyl or alkyl-heterocyclyl;

wherein said alkyl, alkenyl or alkynyl in $R^3$ and/or in $R^4$, if substituted, is substituted with one or more substituents selected from F, Cl, Br, I, $NH_2$, SH or OH, —C(O)OH, or —$OC_{1-4}$alkyl being unsubstituted or substituted by one or more of OH or halogen (F, Cl, I, Br);

wherein $R_z$ is selected from saturated or unsaturated, linear or branched, substituted or unsubstituted $C_{1-6}$ alkyl, unsubstituted $C_{2-6}$ alkenyl, unsubstituted $C_{2-6}$ alkynyl;

with $R_x$ and $R_y$ independently being either H or a saturated or unsaturated, linear or branched, substituted or unsubstituted $C_{1-6}$-alkyl.

In one further embodiment the following substituents are preferred wherein said aryl in $R^1$ and/or in $R^2$, or said ring formed by $R^1$ and $R^2$ or the ring condensed to it, if a substituted aryl, is substituted with one or more substituents selected from halogen (F, Cl, I, Br), —OH, —$NH_2$, —SH, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br);

wherein said heterocyclyl in $R^1$ and/or said heterocyclyl or cycloalkyl in $R^2$, or said ring formed by $R^1$ and $R^2$ or the ring condensed to it, if a substituted heterocyclyl or cycloalkyl, is substituted with one or more substituents selected from halogen (F, Cl, I, Br), —OH, —$NH_2$, —SH, =O, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br);

wherein said alkyl, alkenyl or alkynyl in $R^2$, if substituted, is substituted with one or more substituents selected from F, Cl, Br, I, $NH_2$, SH or OH, —C(O)OH, or —$OC_{1-4}$alkyl being unsubstituted or substituted by one or more of OH or halogen (F, Cl, I, Br);

wherein said aryl in $R^6$, in $R^7$, and/or in $R^8$, if a substituted aryl, is substituted with one or more substituents selected from halogen (F, Cl, I, Br), —OH, —$NH_2$, —SH, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br);

wherein said heterocyclyl or cycloalkyl in in $R^6$, in $R^7$, and/or in $R^8$, if a substituted heterocyclyl or cycloalkyl, is substituted with one or more substituents selected from halogen (F, Cl, I, Br), —OH, —$NH_2$, —SH, =O, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br);

wherein said alkyl, alkenyl or alkynyl in $R^6$, in $R^7$, and/or in $R^8$, if substituted, is substituted with one or more substituents selected from F, Cl, Br, I, $NH_2$, SH or OH, —C(O)OH, or —$OC_{1-4}$alkyl being unsubstituted or substituted by one or more of OH or halogen (F, Cl, I, Br);

wherein said aryl in $R^3$ and/or in $R^4$, if a substituted aryl, is substituted with one or more substituents selected from halogen (F, Cl, I, Br), —OH, —$NH_2$, —SH, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br);

wherein said heterocyclyl or cycloalkyl in in $R^3$ and/or in $R^4$, if a substituted heterocyclyl or cycloalkyl, is substituted with one or more substituents selected from halogen (F, Cl, I, Br), —OH, —$NH_2$, —SH, =O, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br);

wherein said alkyl, alkenyl or alkynyl in $R^3$ and/or in $R^4$, if substituted, is substituted with one or more substituents selected from F, Cl, Br, I, $NH_2$, SH or OH, —C(O)OH, or —$OC_{1-4}$alkyl being unsubstituted or substituted by one or more of OH or halogen (F, Cl, I, Br).

When different radicals $R^1$ to $R^{11}$, $R_x$, $R_y$ or $R_z$ are present simultaneously in the different Formulas of the present invention they may be identical or different.

In the general context of this invention, alkyl is understood as meaning saturated, linear or branched hydrocarbons, which may be unsubstituted or substituted once or several times. It encompasses e.g. —$CH_3$ and —$CH_2$—$CH_3$. In these radicals, $C_{1-2}$-alkyl represents C1- or C2-alkyl, $C_{1-3}$-alkyl represents C1-, C2- or C3-alkyl, $C_{1-4}$-alkyl represents C1-, C2-, C3- or C4-alkyl, $C_{1-5}$-alkyl represents C1-, C2-, C3-, C4-, or C5-alkyl, C1-6-alkyl represents C1-, C2-, C3-, C4-, C5- or C6-alkyl, $C_{1-7}$-alkyl represents C1-, C2-, C3-, C4-, C5-, C6- or C7-alkyl, $C_{1-8}$-alkyl represents C1-, C2-, C3-, C4-, C5-, C6-, C7- or C8-alkyl, $C_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc. Preferably alkyl is understood in the context of this invention as $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl.

Alkenyl is understood as meaning unsaturated, linear or branched hydrocarbons, which may be unsubstituted or substituted once or several times. It encompasses groups like e.g. —CH=CH—$CH_3$. The alkenyl radicals are preferably vinyl (ethenyl), allyl (2-propenyl). Preferably in the context of this invention alkenyl is $C_{2-10}$-alkenyl or $C_{2-8}$-alkenyl like ethylene, propylene, butylene, pentylene, hexylene, heptylene or octylene; or is $C_{1-6}$-alkenyl like ethylene, propylene, butylene, pentylene, or hexylene; or is $C_{1-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. —C≡C—$CH_3$ (1-propinyl). Preferably alkynyl in the context of this invention is $C_{2-10}$-alkynyl or $C_{2-8}$-alkynyl like ethyne, propyne, butyene, pentyne, hexyne, heptyne, or octyne; or is $C_{2-6}$-alkynyl like ethyne, propyne, butyene, pentyne, or hexyne; or is $C_{2-4}$-alkynyl like ethyne, propyne, butyene, pentyne, or hexyne.

In the context of this invention cycloalkyl is understood as meaning saturated and unsaturated (but not aromatic) cyclic hydrocarbons (without a heteroatom in the ring), which can be unsubstituted or once or several times substituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantly. Preferably in the context of this invention cycloalkyl is $C_{3-8}$cycloalkyl like cyclopropyl, cyclobutyl, cyclopentyl, cyclohexyl, cycloheptyl, or cyclooctyl; or is $C_{3-7}$cycloalkyl like cyclopropyl, cyclobutyl, cyclopentyl, cyclohexyl, or cycloheptyl; or is $C_{3-6}$cycloalkyl like cyclopropyl, cyclobutyl, cyclopentyl or cyclohexyl, especially cyclopentyl or cyclohexyl.

In the general connection with alkyl, alkenyl, alkynyl and O-alkyl—unless defined otherwise—the term substituted in the context of this invention is understood as meaning replacement of at least one hydrogen radical on a carbon atom by F, Cl, Br, I, $NH_2$, SH or OH, —C(O)OH, or —$OC_{1-4}$alkyl being unsubstituted or substituted by one or more of OH or halogen (F, Cl, I, Br). More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH=CH—$CHCl_2$.

More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. —CH(OH)—CH=CH—$CHCl_2$.

In the general context of this invention haloalkyl is understood as meaning an alkyl being substituted once or several times by a halogen (selected from F, Cl, Br, I). It encompasses e.g. —$CH_2Cl$, —$CH_2F$, —$CHCl_2$, —$CHF_2$, —$CCl_3$, —$CF_3$ and —$CH_2$—$CHCl_2$. Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include —$CH_2Cl$, —$CH_2F$, —$CHCl_2$, —$CHF_2$, and —$CF_3$.

In the context of this invention haloalkoxy is understood as meaning an —O-alkyl being substituted once or several times by a halogen (selected from F, Cl, Br, I). It encompasses e.g. —$OCH_2Cl$, —$OCH_2F$, —$OCHCl_2$, —$OCHF_2$, —$OCCl_3$, —$OCF_3$ and —$OCH_2$—$CHC_2$. Preferably haloalkoxy is understood in the context of this invention as halogen-substituted —$OC_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include —$OCH_2Cl$, —$OCH_2F$, —$OCHCl_2$, —$OCHF_2$, and —$OCF_3$.

Most preferably in connection with alkyl, alkenyl, alkynyl or O-alkyl, substituted is understood in the context of this invention that any alkyl, alkenyl, alkynyl or O-alkyl which is substituted is substituted by one or more of halogen (F, Cl, I, Br), —OH, —$NH_2$, —SH, —C(O)OH, or —$OC_{1-4}$alkyl being unsubstituted or substituted by one or more of OH or halogen (F, Cl, I, Br).

Aryl is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or once or several times substituted. Most preferably aryl is understood in the context of this invention as phenyl, naphtyl or anthracenyl, preferably is phenyl.

In the context of this invention alkylaryl is understood as meaning an aryl group (see above) being connected to another atom through a $C_{1-6}$-alkyl (see above), which may be branched or linear and is unsubstituted or substituted once or several times. Thus, in the context of this invention alkylaryl is understood as meaning an aryl group (see above) being connected to another atom through a $C_{1-6}$-alkyl (see above). The alkyl may be branched or linear and is unsubstituted, while the aryl may be unsubstituted or substituted once or several times. Preferably alkylaryl is understood as meaning an aryl group (see above) being connected to another atom through 1 to 4 (—$CH_2$—) groups. Most preferably alkylaryl is benzyl (i.e. —$CH_2$-phenyl).

In the context of this invention alkylheterocyclyl is understood as meaning a heterocyclyl group being connected to another atom through a $C_{1-6}$-alkyl (see above), which may be branched or linear and is unsubstituted or substituted once or several times. Thus, in the context of this invention alkylheterocyclyl is understood as meaning a heterocyclyl group (see above) being connected to another atom through a $C_{1-6}$-alkyl (see above). The alkyl may be branched or linear and is unsubstituted, while the heterocyclyl may be unsubstituted or substituted once or several times. Preferably alkylheterocyclyl is understood as meaning an heterocyclyl group (see above) being connected to another atom through 1 to 4 (—$CH_2$—) groups. Most preferably alkylheterocyclyl is —$CH_2$-pyridine.

In the context of this invention alkylcycloalkyl is understood as meaning a cycloalkyl group being connected to another atom through a $C_{1-6}$-alkyl (see above), which may be branched or linear and is unsubstituted or substituted once or several times. Thus, in the context of this invention alkylcycloalkyl is understood as meaning a cycloalkyl group (see above) being connected to another atom through a $C_{1-6}$-alkyl (see above). The alkyl may be branched or linear and is unsubstituted, while the cycloalkyl may be substituted once or several times. Preferably alkylcycloalkyl is understood as meaning a cycloalkyl group (see above) being connected to another atom through 1 to 4 (—$CH_2$—) groups. Most preferably alkylcycloalkyl is —$CH_2$-cyclopropyl.

A heterocyclyl radical or group (also called heterocyclyl hereinafter) is understood as meaning heterocyclic ring systems, with at least one saturated or unsaturated ring which contains one or more heteroatoms from the group consisting of nitrogen, oxygen and/or sulfur in the ring. A heterocyclic group can also be substituted once or several times. Examples include non-aromatic heterocyclyls such as tetrahydropyrane, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, benzo-1,2,5-thiadiazole, benzothiazole, indole, benzotriazole, benzodioxolane, benzodioxane, carbazole and quinazoline.

Subgroups inside the heterocyclyls as understood herein include heteroaryls and non-aromatic heterocyclyls.

the heteroaryl (being equivalent to heteroaromatic radicals or aromatic heterocyclyls) is an aromatic heterocyclic ring system of one or more rings of which at least one aromatic ring contains one or more heteroatoms from the group consisting of nitrogen, oxygen and/or sulfur in the ring; preferably is an aromatic heterocyclic ring system of one or two rings of which at least one aromatic ring contains one or more heteroatoms from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;

the non-aromatic heterocyclyl is a heterocyclic ring system of one or more rings of which at least one ring—with this (or these) ring(s) then not being aromatic—contains one or more heteroatoms from the group consisting of nitrogen, oxygen and/or sulfur in the ring; preferably is a heterocyclic ring system of one or two rings of which one or both rings—with this one or two rings then not being aromatic—contain/s one or more heteroatoms from the group consisting of nitrogen, oxygen and/or sulfur in the ring, more preferably is selected from oxazepam, pyrrolidine, piperidine, piperazine, indene, 2,3-dihydroindene (indane), tetrahydropyran, morpholine, indoline, oxopyrrolidine, benzodioxane, especially is benzodioxane, morpholine, tetrahydropyran, piperidine, oxopyrrolidine, and pyrrolidine.

Preferably in the context of this invention heterocyclyl is defined as a heterocyclic ring system of one or more saturated or unsaturated rings of which at least one ring contains one or more heteroatoms from the group consisting of nitrogen, oxygen and/or sulfur in the ring. Preferably it is a heterocyclic ring system of one or two saturated or unsaturated rings of which at least one ring contains one or more heteroatoms from the group consisting of nitrogen, oxygen and/or sulfur in the ring.

Preferred examples of heterocyclyls include oxazepan, pyrrolidine, imidazole, oxadiazole, tetrazole, pyridine, pyrimidine, piperidine, piperazine, indene, 2,3-dihydroindene, benzofuran, benzimidazole, indazole, benzodiazole, thiazole, benzothiazole, tetrahydropyrane, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyrane, pyrazole, imidazole, piperidine, thiophene, indole, benzimidazole, pyrrolo[2,3b]pyridine, benzoxazole, oxopyrrolidine, pyrimidine, oxazepane and pyrrolidine.

In the context of this invention oxopyrrolidine is understood as meaning pyrrolidin-2-one.

In connection with aryl (including alkyl-aryl), cycloalkyl (including alkyl-cycloalkyl), or heterocyclyl (including alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl by OH, SH, =O, halogen (F, Cl, Br, I), CN, $NO_2$, COOH; $NR_xR_y$, with $R_x$ and $R_y$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl.

Most preferably in connection with aryl (including alkyl-aryl), substituted is understood in the context of this invention that any aryl (including alkyl-aryl), which is substituted is substituted by one or more of halogen (F, Cl, I, Br), —OH, —$NH_2$, —SH, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br).

Most preferably in connection with cycloalkyl (including alkyl-cycloalkyl) or heterocyclyl (including alkyl-heterocyclyl), substituted is understood in the context of this invention that any cycloalkyl and heterocyclyl which is substituted is substituted by one or more of halogen (F, Cl, I, Br), —OH, —$NH_2$, —SH, =O, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br).

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—).

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes which are complexed via ionic interactions.

The term "physiologically acceptable salt" means in the context of this invention any salt that is physiologically tolerated (most of the time meaning not being toxic-especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with $NH_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals.

By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides.

Examples of well known methods of producing a prodrug of a given acting compound are known to those skilled in the art and can be found e.g. in Krogsgaard-Larsen et al. "Textbook of Drug design and Discovery" Taylor & Francis (April 2002).

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon or of a nitrogen by $^{15}N$-enriched nitrogen are within the scope of this invention.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels.

Purity levels for the drug substance are preferably above 50%, more preferably above 70%, most preferably above 90%. In a preferred embodiment it is above 95% of the compound of formula (I) or, or of its salts. This applies also to its solvates or prodrugs.

In a preferred embodiment of the compound according to the invention according to general formula I

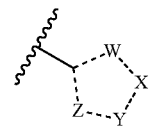

while being either substituted on one of W, X, Y or Z by

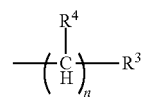

or being fused at W and X to a further ringsystem to the 5-membered heterocyclic ring formed by W—X—Y—Z while being otherwise unsubstituted—is selected from:

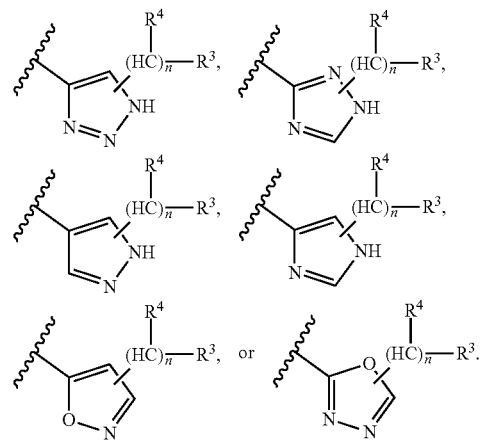

In another embodiment of the invention in the compound according to the invention according to formula I,

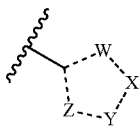

can also form together with the substituent

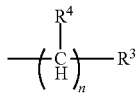

the following unsubstituted ring system:

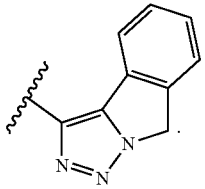

In another preferred embodiment of the compound according to the invention according to general formula I

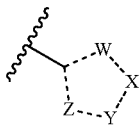

while being either substituted on one of W, X, Y or Z by

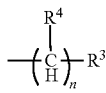

or being fused at W and X to a further ringsystem to the 5-membered heterocyclic ring formed by W—X—Y—Z while being otherwise unsubstituted—is selected from

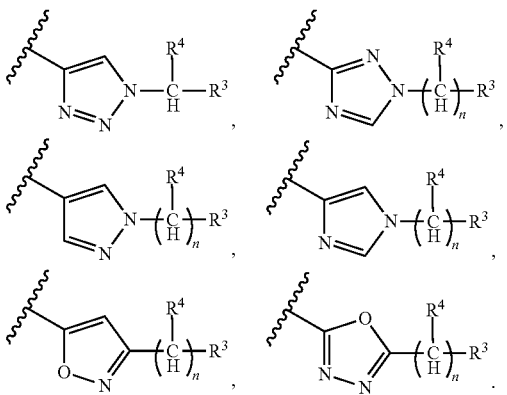

In another preferred embodiment of the compound according to the invention according to general formula I

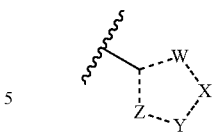

while being either substituted on one of W, X, Y or Z by

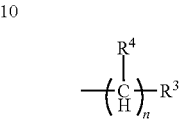

or being fused at W and X to a further ringsystem to the 5-membered heterocyclic ring formed by W—X—Y—Z while being otherwise unsubstituted—is selected from

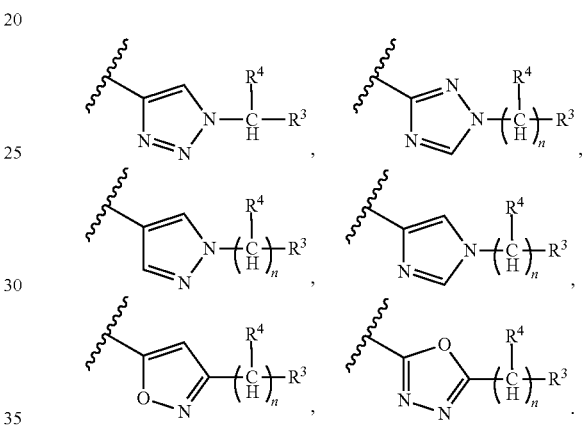

In a further preferred embodiment of the compound according to the invention according to general formula I the compound is a compound according to Formula II,

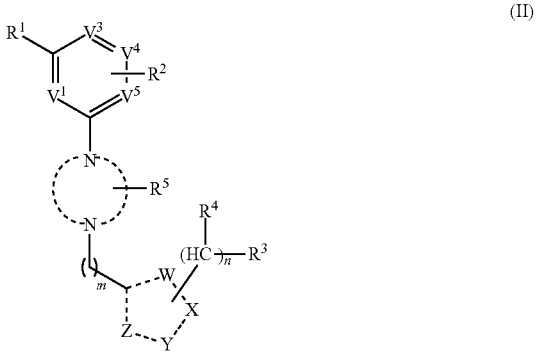

(II)

wherein
m is 1 or 2;
n is 0 or 1;
one of $V^1$, $V^3$, $V^4$ and $V^5$ is selected from nitrogen or carbon while the others are carbon;
$R^1$ is hydroxyl, —$NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl and substituted or unsubstituted heterocyclyl;
$R^2$ is hydrogen, halogen (F, Cl, I, Br), —$NR^6R^7$, —$SR^6$, —$OR^6$, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl; or $R^1$ and $R^2$ are bonded to neighbouring atoms in the ring and together with these atoms form a saturated or unsaturated, substituted or unsubstituted ring, fused to the ring

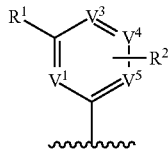

of the corestructure of formula II, which may be condensed with a further unsubstituted or substituted ring system;

$R^3$ is substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl; and $R^4$ is hydrogen, substituted or unsubstituted alkyl, substituted of unsubstituted cycloalkyl, substituted or unsubstituted alkenyl, substituted or unsubstituted alkynyl, substituted of unsubstituted aryl and substituted of unsubstituted heterocyclyl;

$R^5$ is hydrogen, hydroxy, or $CH_3$;

$R^6$, $R^7$ and $R^8$ are independent from each other and selected from the group formed by hydrogen, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom may form a cycloalkylic or heterocyclic 4 to 7-membered ring;

and wherein W, X, Y and Z are selected from carbon, nitrogen, or oxygen while W—X—Y—Z are forming together with the bridging C-atom, that is connected to the core scaffold, a 5-membered heterocyclic ring;

and wherein

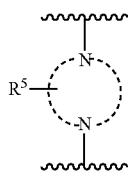

is selected from

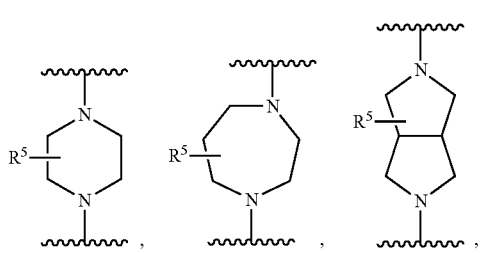

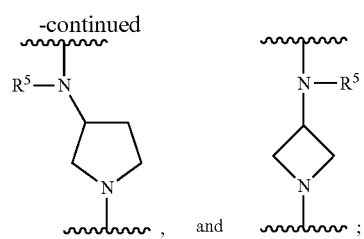

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In one embodiment one or more of the following provisos apply:

with the following provisos applying:
with the proviso that if $V^1$, $V^3$, $V^4$ and $V^5$ are carbon and any of W, X, Y or Z is

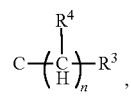

then $R^1$ may not be —$OCH_3$;
and/or
with the proviso that if $V^1$, $V^3$, $V^4$ and $V^5$ are carbon, n is 0 and $R^3$ is —$CH_3$ or —$C_2H_5$, then $R^1$ may not be —$NH_2$.

In a preferred embodiment of the compound according to the invention according to general formula II

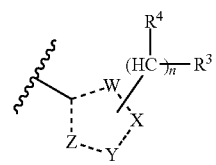

is selected from:

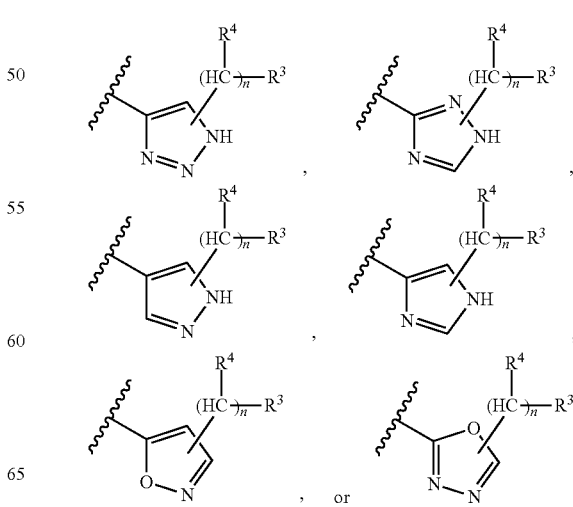

In another preferred embodiment of the compound according to the invention according to general formula II

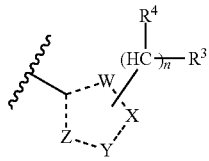

is selected from

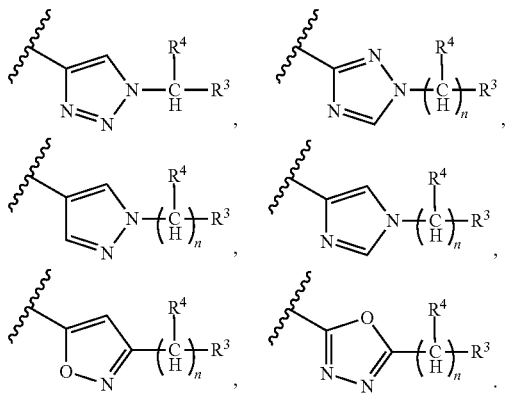

In another embodiment of the invention in the compound according to the invention according to Formula II,

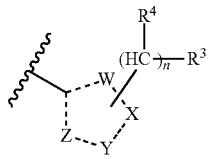

can also form the following unsubstituted ring system

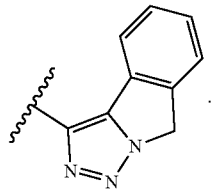 [SMILES: *c1nnn2c1-c1ccccc1C2]

In another preferred embodiment of the compound according to the invention according to general formulas I or II the compound is a compound according to Formula III,

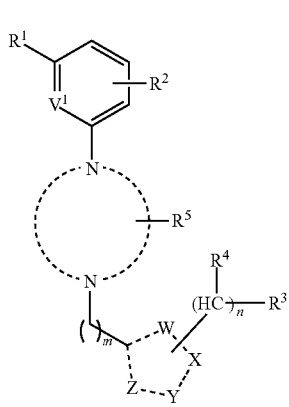

(III)

wherein
m is 1 or 2;
n is 0 or 1;

$V^1$ is selected from nitrogen or carbon;

$R^1$ is hydroxyl, —$NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl and substituted or unsubstituted heterocyclyl;

$R^2$ is hydrogen, halogen (F, Cl, I, Br), —$NR^6R^7$, —$SR^6$, —$OR^6$, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl; or $R^1$ and $R^2$ are bonded to neighbouring atoms in the ring and together with these atoms form a saturated or unsaturated, substituted or unsubstituted ring, fused to the ring

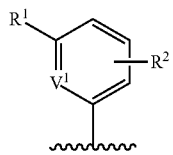

of the corestructure of formula III, which may be condensed with a further unsubstituted or substituted ring system;

$R^3$ is substituted or unsubstituted alkyl, $CONR^6R^7$, substituted or unsubstituted cycloalkyl, substituted or unsubstituted alkenyl, substituted or unsubstituted alkynyl, substituted or unsubstituted aryl and substituted or unsubstituted heterocyclyl;

$R^4$ is hydrogen, substituted or unsubstituted alkyl, substituted of unsubstituted cycloalkyl, substituted or unsubstituted alkenyl, substituted or unsubstituted alkynyl, substituted of unsubstituted aryl and substituted of unsubstituted heterocyclyl;

$R^5$ is hydrogen, hydroxy, or $CH_3$;

$R^6$, $R^7$ and $R^8$ are independent from each other and selected from the group formed by hydrogen, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom may form a cycloalkylic or heterocyclic 4 to 7-membered ring;

and

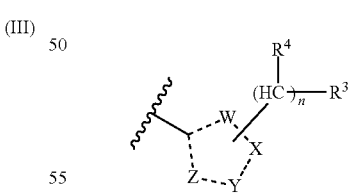

is selected from:

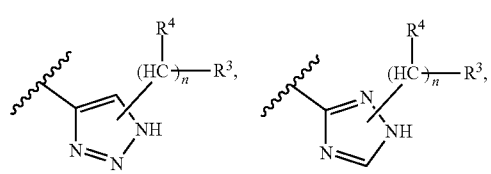

-continued

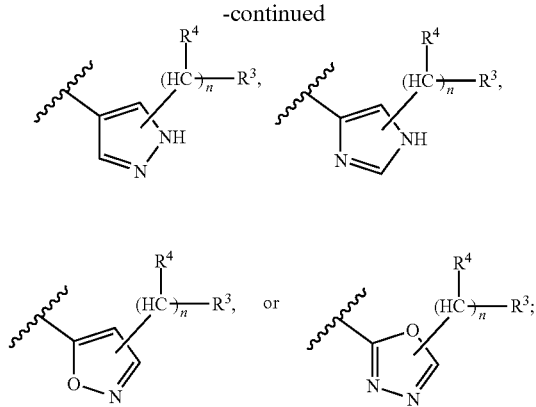

and wherein

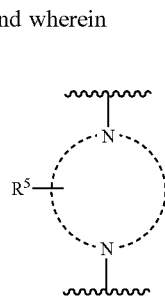

is selected from

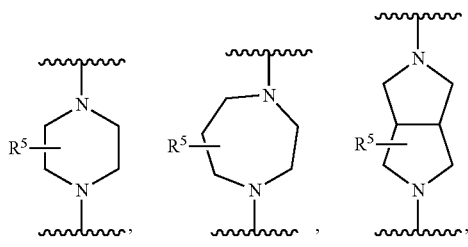

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In one embodiment one or more of the following provisos apply:

with the proviso that if $V^1$ is carbon and

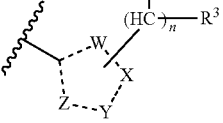

is

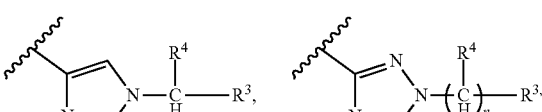

with n=0 and $R^3$ being —$CH_3$ or $O_2H_5$, then $R^1$ may not be $OCH_3$:

and/or with the proviso that if V1 is carbon, n is 0 and $R^3$ is —$CH_3$ or —$O_2H_5$, then $R^1$ may not be —$NH_2$.

In a preferred embodiment of the compound according to the invention according to general formula III

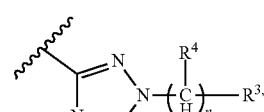

is selected from:

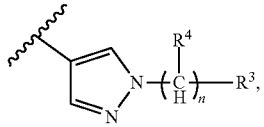
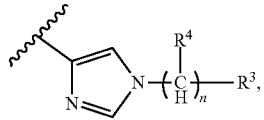

In another preferred embodiment of the compound according to the invention according to general formulas I or II the compound is a compound according to Formula IV,

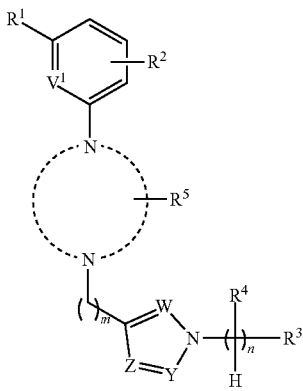
(IV)

wherein
m is 1 or 2;
n is 0 or 1;
$V^1$ is selected from nitrogen or carbon;
$R^1$ is hydroxyl, —$NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl and substituted or unsubstituted heterocyclyl;
$R^2$ is hydrogen, halogen (F, Cl, I, Br), —$NR^6R^7$, —$SR^6$, —$OR^6$, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl;
or
$R^1$ and $R^2$ are bonded to neighbouring atoms in the ring and together with these atoms form a saturated or unsaturated, substituted or unsubstituted ring, fused to the ring

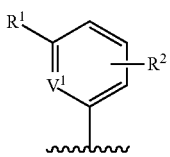

of the corestructure of formula IV, which may be condensed with a further unsubstituted or substituted ring system;
$R^3$ is substituted or unsubstituted alkyl, $CONR^6R^7$, substituted or unsubstituted cycloalkyl, substituted or unsubstituted alkenyl, substituted or unsubstituted alkynyl, substituted or unsubstituted aryl and substituted or unsubstituted heterocyclyl;
$R^4$ is hydrogen, substituted or unsubstituted alkyl, substituted of unsubstituted cycloalkyl, substituted or unsubstituted alkenyl, substituted or unsubstituted alkynyl, substituted of unsubstituted aryl and substituted of unsubstituted heterocyclyl;
$R^5$ is hydrogen, hydroxy, or $CH_3$;
$R^6$, $R^7$ and $R^8$ are independent from each other and selected from the group formed by hydrogen, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom may form a cycloalkylic or heterocyclic 4 to 7-membered ring;

and W, Y and Z are independently from one another selected from N or CH with only 1 or 2 of them being CH; and wherein

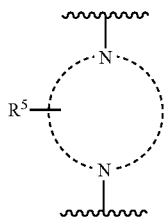

is selected from

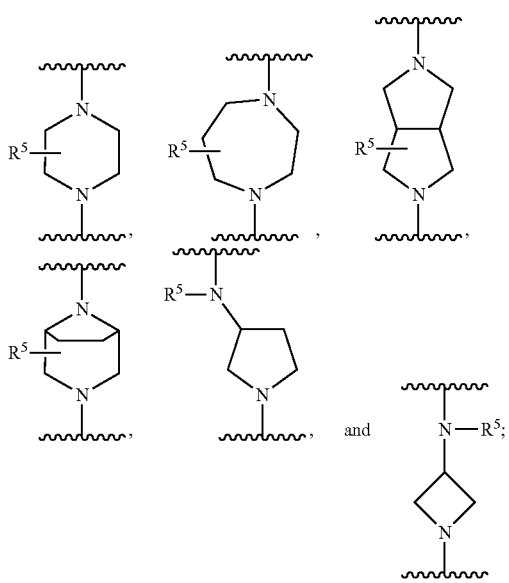

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In one embodiment the following proviso applies:
with the proviso that if $V^1$ is carbon, 2 of W, Y and Z are CH, n is 0 and $R^3$ is —$CH_3$ or —$C_2H_5$, then $R^1$ may not be —$NH_2$.

In a preferred embodiment of the compound according to the invention according to general formula IV above

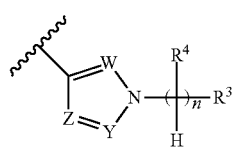

is selected from:

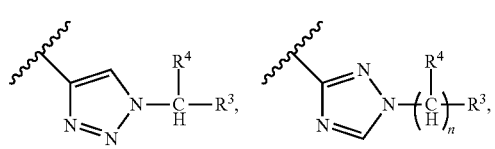

-continued

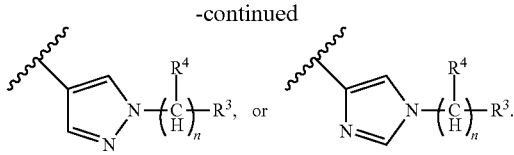

In a preferred embodiment of the compound according to the invention according to general formula IV above the compound is a compound according to Formula IV, wherein $R^3$ is $CONR^6R^7$, substituted or unsubstituted cycloalkyl, substituted or unsubstituted alkenyl, substituted or unsubstituted alkynyl, substituted or unsubstituted aryl and substituted or unsubstituted heterocyclyl, preferably is substituted or unsubstituted cycloalkyl, substituted or unsubstituted aryl and substituted or unsubstituted heterocyclyl.

In another preferred embodiment of the compound according to the invention according to general formulas I or II the compound is a compound according to Formula V

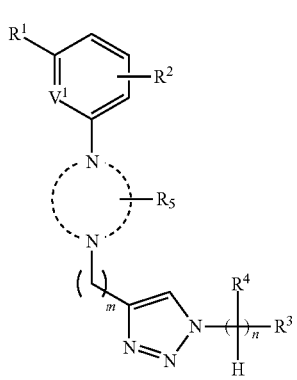

(V)

wherein
m is 1 or 2;
n is 0 or 1;
$V^1$ is selected from nitrogen or carbon;
$R^1$ is hydroxyl, $-NR^6R^7$, $-NR^6S(O)_2R^7$, $-NR^6COR^7$, $-NR^6CONR^7R^8$, $-SR^6$, $-S(O)_2R^6$, $-S(O)_2NR^6R^7$, $-CONR^6R^7$, substituted or unsubstituted aryl and substituted or unsubstituted heterocyclyl;
$R^2$ is hydrogen, halogen (F, Cl, I, Br), $-NR^6R^7$, $-SR^6$, $-OR^6$, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl;
or
$R^1$ and $R^2$ are bonded to neighbouring atoms in the ring and together with these atoms form a saturated or unsaturated, substituted or unsubstituted ring, fused to the ring

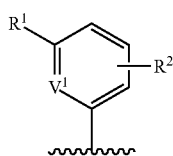

of the corestructure of formula IV, which may be condensed with a further unsubstituted or substituted ring system;
$R^3$ is substituted or unsubstituted alkyl, $CONR^6R^7$, substituted or unsubstituted cycloalkyl, substituted or unsubstituted alkenyl, substituted or unsubstituted alkynyl, substituted or unsubstituted aryl and substituted or unsubstituted heterocyclyl;
$R^4$ is hydrogen, substituted or unsubstituted alkyl, substituted of unsubstituted cycloalkyl, substituted or unsubstituted alkenyl, substituted or unsubstituted alkynyl, substituted of unsubstituted aryl and substituted of unsubstituted heterocyclyl;
$R^5$ is hydrogen, hydroxy, or $CH_3$;
$R^6$, $R^7$ and $R^8$ are independent from each other and selected from the group formed by hydrogen, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom may form a cycloalkylic or heterocyclic 4 to 7-membered ring;
and wherein

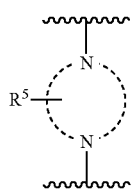

is selected from

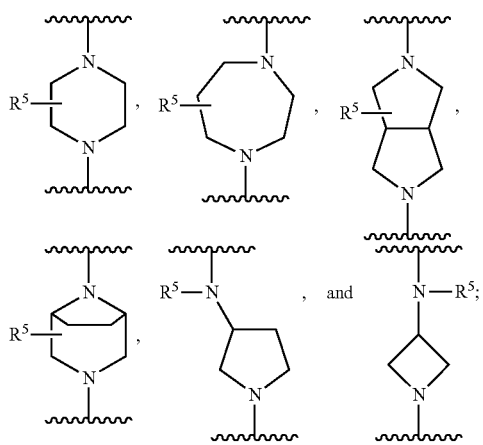

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I or II the compound is a compound according to Formula V (with the preferred substituents)

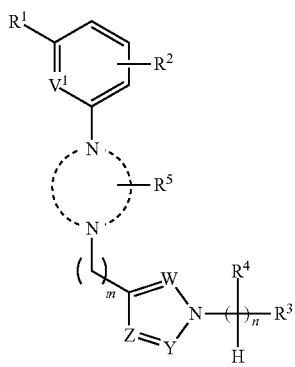

(IV)

wherein
m is 1 or 2;
n is 0 or 1;
$V^1$ is selected from nitrogen or carbon;
$R^1$ is hydroxyl, —$NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl and substituted or unsubstituted heterocyclyl;
$R^2$ is hydrogen, halogen, —$NR^6R^7$, —$SR^6$, —$OR^6$, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl;
or
$R^1$ and $R^2$ are bonded to neighbouring atoms in the ring and together with these atoms form a saturated or unsaturated, substituted or unsubstituted ring, fused to the ring

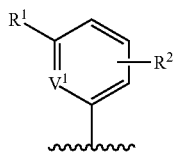

of the corestructure of formula IV, which may be condensed with a further unsubstituted or substituted ring system;
wherein said aryl in $R^1$ and/or in $R^2$, or said ring formed by $R^1$ and $R^2$ or the ring condensed to it, if a substituted aryl, is substituted with one or more substituents selected from halogen (F, Cl, I, Br), —OH, —$NH_2$, —SH, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br);
wherein said heterocyclyl in $R^1$ and/or said heterocyclyl or cycloalkyl in $R^2$, or said ring formed by $R^1$ and $R^2$ or the ring condensed to it, if a substituted heterocyclyl or cycloalkyl, is substituted with one or more substituents selected from halogen (F, Cl, I, Br), —OH, —$NH_2$, —SH, =O, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br);

wherein said alkyl, alkenyl or alkynyl in $R^2$, if substituted, is substituted with one or more substituents selected from F, Cl, Br, I, $NH_2$, SH or OH, —C(O)OH, or —$OC_{1-4}$alkyl being unsubstituted or substituted by one or more of OH or halogen (F, Cl, I, Br);
$R^3$ is substituted or unsubstituted alkyl, $CONR^6R^7$, substituted or unsubstituted cycloalkyl, substituted or unsubstituted alkenyl, substituted or unsubstituted alkynyl, substituted or unsubstituted aryl and substituted or unsubstituted heterocyclyl;
$R^4$ is hydrogen, substituted or unsubstituted alkyl, substituted of unsubstituted cycloalkyl, substituted or unsubstituted alkenyl, substituted or unsubstituted alkynyl, substituted of unsubstituted aryl and substituted of unsubstituted heterocyclyl;
wherein said aryl in $R^3$ and/or in $R^4$, if a substituted aryl, is substituted with one or more substituents selected from halogen (F, Cl, I, Br), —OH, —$NH_2$, —SH, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br);
wherein said heterocyclyl or cycloalkyl in in $R^3$ and/or in $R^4$, if a substituted heterocyclyl or cycloalkyl, is substituted with one or more substituents selected from halogen (F, Cl, I, Br), —OH, —$NH_2$, —SH, =O, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br);
wherein said alkyl, alkenyl or alkynyl in $R^3$ and/or in $R^4$, if substituted, is substituted with one or more substituents selected from F, Cl, Br, I, $NH_2$, SH or OH, —C(O)OH, or —$OC_{1-4}$alkyl being unsubstituted or substituted by one or more of OH or halogen (F, Cl, I, Br);
$R^5$ is hydrogen, hydroxy, or $CH_3$;
$R^6$, $R^7$ and $R^8$ are independent from each other and selected from the group formed by hydrogen, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom may form a cycloalkylic or heterocyclic 4 to 7-membered ring;
wherein said aryl in $R^6$, in $R^7$, and/or in $R^8$, if a substituted aryl, is substituted with one or more substituents selected from halogen (F, Cl, I, Br), —OH, —$NH_2$, —SH, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br);
wherein said heterocyclyl or cycloalkyl in in $R^6$, in $R^7$, and/or in $R^8$, if a substituted heterocyclyl or cycloalkyl, is substituted with one or more substituents selected from halogen (F, Cl, I, Br), —OH, —$NH_2$, —SH, =O, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br);
wherein said alkyl, alkenyl or alkynyl in $R^6$, in $R^7$, and/or in $R^8$, if substituted, is substituted with one or more substituents selected from F, Cl, Br, I, $NH_2$, SH or OH, —C(O)OH, or —$OC_{1-4}$alkyl being unsubstituted or substituted by one or more of OH or halogen (F, Cl, I, Br);

and W, Y and Z are independently from one another selected from N or CH with only 1 or 2 of them being CH;

and wherein

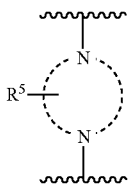

is selected from

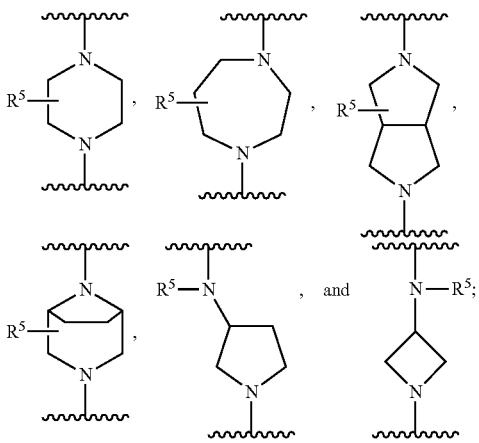

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof;

with the following proviso applying:
with the proviso that if $V^1$ is carbon, 2 of W, Y and Z are CH, n is 0 and $R^3$ is —$CH_3$ or —$O_2H_5$, then $R^1$ may not be —$NH_2$.

In another preferred embodiment of the compound according to the invention according to general formula V the compound is selected from N-(3-(4-((1-phenyl-1H-1,2,3-triazol-4-yl)methyl)piperazin-1-yl)phenyl)propane-2-sulfonamide,
N-(6-(4-((1-(5-chloropyridin-3-yl)-1H-1,2,3-triazol-4-yl)methyl)piperazin-1-yl)pyridin-2-yl)propane-2-sulfonamide,
N-(3-(4-((1-benzyl-1H-1,2,3-triazol-4-yl)methyl)piperazin-1-yl)phenyl)methanesulfonamide,
N-(3-(4-((1-phenyl-1H-1,2,3-triazol-4-yl)methyl)piperazin-1-yl)phenyl)methanesulfonamide,
3-(4-((1-phenyl-1H-1,2,3-triazol-4-yl)methyl)piperazin-1-yl)phenol,
3-(4-((1-benzyl-1H-1,2,3-triazol-4-yl)methyl)piperazin-1-yl)phenol,
3-(4-((1-(pyridin-2-yl)-1H-1,2,3-triazol-4-yl)methyl)piperazin-1-yl)phenol,
N-(3-(4-((1-(6-(trifluoromethyl)pyridin-3-yl)-1H-1,2,3-triazol-4-yl)methyl)piperazin-1-yl)phenyl)methanesulfonamide,
N-(3-(4-((1-(2-fluorophenyl)-1H-1,2,3-triazol-4-yl)methyl)piperazin-1-yl)phenyl)propane-2-sulfonamide,
N-(3-(4-((1-phenyl-1H-1,2,3-triazol-4-yl)methyl)piperazin-1-yl)phenyl)ethanesulfonamide,
N-(3-(1-((1-phenyl-1H-1,2,3-triazol-4-yl)methyl)pyrrolidin-3-ylamino)phenyl)methanesulfonamide,
N-(3-(1-((1-phenyl-1H-1,2,3-triazol-4-yl)methyl)azetidin-3-ylamino)phenyl)methanesulfonamide,
N-(3-(5-((1-phenyl-1H-1,2,3-triazol-4-yl)methyl)hexahydropyrrolo[3,4-c]pyrrol-2(1H)-yl)phenyl)methanesulfonamide,
N-(3-(methyl(1-((1-phenyl-1H-1,2,3-triazol-4-yl)methyl)pyrrolidin-3-yl)amino)phenyl)methanesulfonamide,
N-(3-(methyl(1-((1-phenyl-1H-1,2,3-triazol-4-yl)methyl)azetidin-3-yl)amino)phenyl)methanesulfonamide,
N-(3-(4-((1-(pyridin-2-ylmethyl)-1H-1,2,3-triazol-4-yl)methyl)piperazin-1-yl)phenyl)propane-2-sulfonamide,
N-(3-(4-((1-(pyridin-2-yl)-1H-1,2,3-triazol-4-yl)methyl)piperazin-1-yl)phenyl)propane-2-sulfonamide,
1,1,1-trifluoro-N-(3-(4-((1-phenyl-1H-1,2,3-triazol-4-yl)methyl)piperazin-1-yl)phenyl)methanesulfonamide,
N-(3-(4-((1-(5-fluoropyridin-2-yl)-1H-1,2,3-triazol-4-yl)methyl)piperazin-1-yl)phenyl)propane-2-sulfonamide,
N-(3-(4-((1-phenyl-1H-1,2,3-triazol-4-yl)methyl)piperazin-1-yl)phenyl)cyclopropanesulfonamide,
N-(3-(4-((1-(3-fluoropyridin-2-yl)-1H-1,2,3-triazol-4-yl)methyl)piperazin-1-yl)phenyl)propane-2-sulfonamide,
N-(3-(4-((1-(4-fluoropyridin-2-yl)-1H-1,2,3-triazol-4-yl)methyl)piperazin-1-yl)phenyl)propane-2-sulfonamide,
N-(3-((1R,5S)-3-((1-phenyl-1H-1,2,3-triazol-4-yl)methyl)-3,8-diazabicyclo[3.2.1]octan-8-yl)phenyl)methanesulfonamide,
N-(3-(4-((2-(pyridin-2-yl)-2H-1,2,3-triazol-4-yl)methyl)piperazin-1-yl)phenyl)propane-2-sulfonamide,
N-(3-(4-((1-phenyl-1H-1,2,3-triazol-4-yl)methyl)-1,4-diazepan-1-yl)phenyl)methanesulfonamide,
N-(3-(methyl(1-((1-phenyl-1H-1,2,3-triazol-4-yl)methyl)pyrrolidin-3-yl)amino)phenyl)propane-2-sulfonamide,
N-(3-(4-((1-(3-fluorophenyl)-1H-1,2,3-triazol-4-yl)methyl)piperazin-1-yl)phenyl)propane-2-sulfonamide,
N-(3-(4-((1-(4-fluorophenyl)-1H-1,2,3-triazol-4-yl)methyl)piperazin-1-yl)phenyl)propane-2-sulfonamide,
N-(3-(4-((1-(6-fluoropyridin-2-yl)-1H-1,2,3-triazol-4-yl)methyl)piperazin-1-yl)phenyl)propane-2-sulfonamide,
N-(3-(5-((1-phenyl-1H-1,2,3-triazol-4-yl)methyl)hexahydropyrrolo[3,4-c]pyrrol-2(1H)-yl)phenyl)propane-2-sulfonamide,
3-(4-((1-phenyl-1H-1,2,3-triazol-4-yl)methyl)piperazin-1-yl)aniline,
N-tert-butyl-3-(4-((1-phenyl-1H-1,2,3-triazol-4-yl)methyl)piperazin-1-yl)benzenesulfonamide,
N-(6-(4-((1-phenyl-1H-1,2,3-triazol-4-yl)methyl)piperazin-1-yl)pyridin-2-yl)methanesulfonamide,
N-(6-(4-((1-phenyl-1H-1,2,3-triazol-4-yl)methyl)piperazin-1-yl)pyridin-2-yl)propane-2-sulfonamide,
N-(6-(4-((1-(2-fluorophenyl)-1H-1,2,3-triazol-4-yl)methyl)piperazin-1-yl)pyridin-2-yl)propane-2-sulfonamide,
N-(6-(4-((1-(2-fluorophenyl)-1H-1,2,3-triazol-4-yl)methyl)piperazin-1-yl)pyridin-2-yl)cyclopropanesulfonamide,
N-(6-(4-((1-(2-fluorophenyl)-1H-1,2,3-triazol-4-yl)methyl)piperazin-1-yl)pyridin-2-yl)propionamide,
N-(6-(4-((1-(2-hydroxyphenyl)-1H-1,2,3-triazol-4-yl)methyl)piperazin-1-yl)pyridin-2-yl)propane-2-sulfonamide, N-(6-(4-((1-(pyridin-2-yl)-1H-pyrazol-4-yl)methyl)piperazin-1-yl)pyridin-2-yl)propane-2-sulfonamide,
N-(6-(4-((1-(2,6-difluorophenyl)-1H-1,2,3-triazol-4-yl)methyl)piperazin-1-yl)pyridin-2-yl)propane-2-sulfonamide,
N-(6-(4-((1-(3,4-difluorophenyl)-1H-1,2,3-triazol-4-yl)methyl)piperazin-1-yl)pyridin-2-yl)propane-2-sulfonamide,
N-(6-(4-((1-(4-chloro-2-fluorophenyl)-1H-1,2,3-triazol-4-yl)methyl)piperazin-1-yl)pyridin-2-yl)propane-2-sulfonamide,
N-(6-(4-((1-phenyl-1H-1,2,3-triazol-4-yl)methyl)piperazin-1-yl)pyridin-2-yl)cyclopropanesulfonamide,
N-(5-chloro-6-(4-((1-phenyl-1H-1,2,3-triazol-4-yl)methyl)piperazin-1-yl)pyridin-2-yl)propane-2-sulfonamide,
N-(6-(5-((1-phenyl-1H-1,2,3-triazol-4-yl)methyl)hexahydropyrrolo[3,4-c]pyrrol-2(1H)-yl)pyridin-2-yl)propane-2-sulfonamide,
N-(6-(5-((1-benzyl-1H-1,2,3-triazol-4-yl)methyl)hexahydropyrrolo[3,4-c]pyrrol-2(1H)-yl)pyridin-2-yl)propane-2-sulfonamide,
N-(6-(5-((1-(pyridin-2-ylmethyl)-1H-1,2,3-triazol-4-yl)methyl)hexahydropyrrolo[3,4-c]pyrrol-2(1H)-yl)pyridin-2-yl)propane-2-sulfonamide,
N-(6-(4-((1-(5-methoxypyridin-3-yl)-1H-1,2,3-triazol-4-yl)methyl)piperazin-1-yl)pyridin-2-yl)propane-2-sulfonamide,
N-(6-(4-((1-phenyl-1H-1,2,3-triazol-4-yl)methyl)-1,4-diazepan-1-yl)pyridin-2-yl)propane-2-sulfonamide,
N-(6-(4-((1-(5-chloropyridin-2-yl)-1H-1,2,3-triazol-4-yl)methyl)piperazin-1-yl)pyridin-2-yl)propane-2-sulfonamide,
N-(6-(4-((1-(pyridin-2-ylmethyl)-1H-1,2,3-triazol-4-yl)methyl)-1,4-diazepan-1-yl)pyridin-2-yl)propane-2-sulfonamide,
N-(6-(4-((1-(2-fluorophenyl)-1H-1,2,3-triazol-4-yl)methyl)-1-1,4-diazepan-1-yl)pyridin-2-yl)propane-2-sulfonamide,
N-(6-(5-((1-(2-fluorophenyl)-1H-1,2,3-triazol-4-yl)methyl)hexahydropyrrolo[3,4-c]pyrrol-2(1H)-yl)pyridin-2-yl)propane-2-sulfonamide, and
N-(6-(4-((1-(pyridin-2-yl)-1H-imidazol-4-yl)methyl)piperazin-1-yl)pyridin-2-yl)propane-2-sulfonamide;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment of the compound according to the invention according to general formulas I, II, III, or IV the compound is selected from
N-(3-(4-((1-phenyl-1H-1,2,3-triazol-4-yl)methyl)piperazin-1-yl)phenyl)propane-2-sulfonamide,
N-(6-(4-((1-(5-chloropyridin-3-yl)-1H-1,2,3-triazol-4-yl)methyl)piperazin-1-yl)pyridin-2-yl)propane-2-sulfonamide,
N-(3-(4-((1-benzyl-1H-1,2,3-triazol-4-yl)methyl)piperazin-1-yl)phenyl)methanesulfonamide,
N-(3-(4-((1-phenyl-1H-1,2,3-triazol-4-yl)methyl)piperazin-1-yl)phenyl)methanesulfonamide,
3-(4-((1-phenyl-1H-1,2,3-triazol-4-yl)methyl)piperazin-1-yl)phenol,
3-(4-((1-benzyl-1H-1,2,3-triazol-4-yl)methyl)piperazin-1-yl)phenol,
3-(4-((1-(pyridin-2-yl)-1H-1,2,3-triazol-4-yl)methyl)piperazin-1-yl)phenol,
N-(3-(4-((1-(2-fluorophenyl)-1H-1,2,3-triazol-4-yl)methyl)piperazin-1-yl)phenyl)propane-2-sulfonamide,
N-(3-(4-((1-phenyl-1H-1,2,3-triazol-4-yl)methyl)piperazin-1-yl)phenyl)ethanesulfonamide,
N-(3-(1-((1-phenyl-1H-1,2,3-triazol-4-yl)methyl)pyrrolidin-3-ylamino)phenyl)methanesulfonamide,
N-(3-(1-((1-phenyl-1H-1,2,3-triazol-4-yl)methyl)azetidin-3-ylamino)phenyl)methanesulfonamide,
N-(3-(5-((1-phenyl-1H-1,2,3-triazol-4-yl)methyl)hexahydropyrrolo[3,4-c]pyrrol-2(1H)-yl)phenyl)methanesulfonamide,
N-(3-(methyl(1-((1-phenyl-1H-1,2,3-triazol-4-yl)methyl)pyrrolidin-3-yl)amino)phenyl)methanesulfonamide,
N-(3-(methyl(1-((1-phenyl-1H-1,2,3-triazol-4-yl)methyl)azetidin-3-yl)amino)phenyl)methanesulfonamide,
N-(3-(4-((1-(pyridin-2-ylmethyl)-1H-1,2,3-triazol-4-yl)methyl)piperazin-1-yl)phenyl)propane-2-sulfonamide,
N-(3-(4-((1-(pyridin-2-yl)-1H-1,2,3-triazol-4-yl)methyl)piperazin-1-yl)phenyl)propane-2-sulfonamide,
N-(3-(4-((1-(5-fluoropyridin-2-yl)-1H-1,2,3-triazol-4-yl)methyl)piperazin-1-yl)phenyl)propane-2-sulfonamide,
N-(3-(4-((1-phenyl-1H-1,2,3-triazol-4-yl)methyl)piperazin-1-yl)phenyl)cyclopropanesulfonamide,
N-(3-(4-((1-(3-fluoropyridin-2-yl)-1H-1,2,3-triazol-4-yl)methyl)piperazin-1-yl)phenyl)propane-2-sulfonamide,
N-(3-(4-((1-(4-fluoropyridin-2-yl)-1H-1,2,3-triazol-4-yl)methyl)piperazin-1-yl)phenyl)propane-2-sulfonamide,
N-(3-((1R,5S)-3-((1-phenyl-1H-1,2,3-triazol-4-yl)methyl)-3,8-diazabicyclo[3.2.1]octan-8-yl)phenyl)methanesulfonamide,
N-(3-(4-((2-(pyridin-2-yl)-2H-1,2,3-triazol-4-yl)methyl)piperazin-1-yl)phenyl)propane-2-sulfonamide,
N-(3-(4-((1-phenyl-1H-1,2,3-triazol-4-yl)methyl)-1,4-diazepan-1-yl)phenyl)methanesulfonamide,
N-(3-(methyl(1-((1-phenyl-1H-1,2,3-triazol-4-yl)methyl)pyrrolidin-3-yl)amino)phenyl)propane-2-sulfonamide,
N-(3-(4-((1-(3-fluorophenyl)-1H-1,2,3-triazol-4-yl)methyl)piperazin-1-yl)phenyl)propane-2-sulfonamide,
N-(3-(4-((1-(4-fluorophenyl)-1H-1,2,3-triazol-4-yl)methyl)piperazin-1-yl)phenyl)propane-2-sulfonamide,
N-(3-(4-((1-(6-fluoropyridin-2-yl)-1H-1,2,3-triazol-4-yl)methyl)piperazin-1-yl)phenyl)propane-2-sulfonamide,
N-(3-(5-((1-phenyl-1H-1,2,3-triazol-4-yl)methyl)hexahydropyrrolo[3,4-c]pyrrol-2(1H)-yl)phenyl)propane-2-sulfonamide,
N-tert-butyl-3-(4-((1-phenyl-1H-1,2,3-triazol-4-yl)methyl)piperazin-1-yl)benzenesulfonamide,
N-(6-(4-((1-phenyl-1H-1,2,3-triazol-4-yl)methyl)piperazin-1-yl)pyridin-2-yl)methanesulfonamide,
N-(6-(4-((1-phenyl-1H-1,2,3-triazol-4-yl)methyl)piperazin-1-yl)pyridin-2-yl)propane-2-sulfonamide,
N-(6-(4-((1-(2-fluorophenyl)-1H-1,2,3-triazol-4-yl)methyl)piperazin-1-yl)pyridin-2-yl)propane-2-sulfonamide,
N-(6-(4-((1-(2-fluorophenyl)-1H-1,2,3-triazol-4-yl)methyl)piperazin-1-yl)pyridin-2-yl)cyclopropanesulfonamide,
N-(6-(4-((1-(2-fluorophenyl)-1H-1,2,3-triazol-4-yl)methyl)piperazin-1-yl)pyridin-2-yl)propionamide,
N-(6-(4-((1-(2-hydroxyphenyl)-1H-1,2,3-triazol-4-yl)methyl)piperazin-1-yl)pyridin-2-yl)propane-2-sulfonamide,
N-(6-(4-((1-(pyridin-2-yl)-1H-pyrazol-4-yl)methyl)piperazin-1-yl)pyridin-2-yl)propane-2-sulfonamide,
N-(6-(4-((1-(2,6-difluorophenyl)-1H-1,2,3-triazol-4-yl)methyl)piperazin-1-yl)pyridin-2-yl)propane-2-sulfonamide, N-(6-(4-((1-(3,4-difluorophenyl)-1H-1,2,3-triazol-4-yl)
methyl)piperazin-1-yl)pyridin-2-yl)propane-2-sulfona-
mide,
N-(6-(4-((1-(4-chloro-2-fluorophenyl)-1H-1,2,3-triazol-4-
yl)methyl)piperazin-1-yl)pyridin-2-yl)propane-2-sulfo-
namide,
N-(6-(4-((1-phenyl-1H-1,2,3-triazol-4-yl)methyl)piperazin-
1-yl)pyridin-2-yl)cyclopropanesulfonamide,
N-(5-chloro-6-(4-((1-phenyl-1H-1,2,3-triazol-4-yl)methyl)
piperazin-1-yl)pyridin-2-yl)propane-2-sulfonamide,
N-(6-(5-((1-phenyl-1H-1,2,3-triazol-4-yl)methyl)hexahy-
dropyrrolo[3,4-c]pyrrol-2(1H)-yl)pyridin-2-yl)propane-
2-sulfonamide,
N-(6-(5-((1-benzyl-1H-1,2,3-triazol-4-yl)methyl)hexahy-
dropyrrolo[3,4-c]pyrrol-2(1H)-yl)pyridin-2-yl)propane-
2-sulfonamide,
N-(6-(5-((1-(pyridin-2-ylmethyl)-1H-1,2,3-triazol-4-yl)
methyl)hexahydropyrrolo[3,4-c]pyrrol-2(1H)-yl)pyridin-
2-yl)propane-2-sulfonamide,
N-(6-(4-((1-(5-methoxypyridin-3-yl)-1H-1,2,3-triazol-4-yl)
methyl)piperazin-1-yl)pyridin-2-yl)propane-2-sulfona-
mide,
N-(6-(4-((1-phenyl-1H-1,2,3-triazol-4-yl)methyl)-1,4-diaz-
epan-1-yl)pyridin-2-yl)propane-2-sulfonamide,
N-(6-(4-((1-(5-chloropyridin-2-yl)-1H-1,2,3-triazol-4-yl)
methyl)piperazin-1-yl)pyridin-2-yl)propane-2-sulfona-
mide,
N-(6-(4-((1-(pyridin-2-ylmethyl)-1H-1,2,3-triazol-4-yl)
methyl)-1,4-diazepan-1-yl)pyridin-2-yl)propane-2-sulfo-
namide,
N-(6-(4-((1-(2-fluorophenyl)-1H-1,2,3-triazol-4-yl)
methyl)-1-1,4-diazepan-1-yl)pyridin-2-yl)propane-2-sul-
fonamide,
N-(6-(5-((1-(2-fluorophenyl)-1H-1,2,3-triazol-4-yl)methyl)
hexahydropyrrolo[3,4-c]pyrrol-2(1H)-yl)pyridin-2-yl)
propane-2-sulfonamide, and
N-(6-(4-((1-(pyridin-2-yl)-1H-imidazol-4-yl)methyl)piper-
azin-1-yl)pyridin-2-yl)propane-2-sulfonamide;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, II, III, or IV the compound is selected from
N-(3-(4-((1-phenyl-1H-1,2,3-triazol-4-yl)methyl)piperazin-
1-yl)phenyl)propane-2-sulfonamide,
N-(3-(4-((1-phenyl-1H-1,2,3-triazol-4-yl)methyl)piperazin-
1-yl)phenyl)methanesulfonamide,
3-(4-((1-benzyl-1H-1,2,3-triazol-4-yl)methyl)piperazin-1-
yl)phenol,
N-(3-(4-((1-(2-fluorophenyl)-1H-1,2,3-triazol-4-yl)methyl)
piperazin-1-yl)phenyl)propane-2-sulfonamide,
N-(3-(4-((1-phenyl-1H-1,2,3-triazol-4-yl)methyl)piperazin-
1-yl)phenyl)ethanesulfonamide,
N-(3-(1-((1-phenyl-1H-1,2,3-triazol-4-yl)methyl)pyrroli-
din-3-ylamino)phenyl)methanesulfonamide,
N-(3-(1-((1-phenyl-1H-1,2,3-triazol-4-yl)methyl)azetidin-
3-ylamino)phenyl)methanesulfonamide,
N-(3-(5-((1-phenyl-1H-1,2,3-triazol-4-yl)methyl)hexahy-
dropyrrolo[3,4-c]pyrrol-2(1H)-yl)phenyl)methanesulfo-
namide,
N-(3-(methyl(1-((1-phenyl-1H-1,2,3-triazol-4-yl)methyl)
pyrrolidin-3-yl)amino)phenyl)methanesulfonamide,
N-(3-(methyl(1-((1-phenyl-1H-1,2,3-triazol-4-yl)methyl)
azetidin-3-yl)amino)phenyl)methanesulfonamide,
N-(3-(4-((1-(pyridin-2-yl)-1H-1,2,3-triazol-4-yl)methyl)
piperazin-1-yl)phenyl)propane-2-sulfonamide,
N-(3-(4-((1-phenyl-1H-1,2,3-triazol-4-yl)methyl)piperazin-
1-yl)phenyl)cyclopropanesulfonamide,
N-(3-(4-((1-phenyl-1H-1,2,3-triazol-4-yl)methyl)-1,4-diaz-
epan-1-yl)phenyl)methanesulfonamide,
N-(3-(methyl(1-((1-phenyl-1H-1,2,3-triazol-4-yl)methyl)
pyrrolidin-3-yl)amino)phenyl)propane-2-sulfonamide,
N-(3-(4-((1-(3-fluorophenyl)-1H-1,2,3-triazol-4-yl)methyl)
piperazin-1-yl)phenyl)propane-2-sulfonamide,
N-(3-(4-((1-(4-fluorophenyl)-1H-1,2,3-triazol-4-yl)methyl)
piperazin-1-yl)phenyl)propane-2-sulfonamide,
N-(3-(4-((1-(6-fluoropyridin-2-yl)-1H-1,2,3-triazol-4-yl)
methyl)piperazin-1-yl)phenyl)propane-2-sulfonamide,
N-(3-(5-((1-phenyl-1H-1,2,3-triazol-4-yl)methyl)hexahy-
dropyrrolo[3,4-c]pyrrol-2(1H)-yl)phenyl)propane-2-sul-
fonamide,
N-(6-(4-((1-phenyl-1H-1,2,3-triazol-4-yl)methyl)piperazin-
1-yl)pyridin-2-yl)methanesulfonamide,
N-(6-(4-((1-phenyl-1H-1,2,3-triazol-4-yl)methyl)piperazin-
1-yl)pyridin-2-yl)propane-2-sulfonamide,
N-(6-(4-((1-(2-fluorophenyl)-1H-1,2,3-triazol-4-yl)methyl)
piperazin-1-yl)pyridin-2-yl)propane-2-sulfonamide,
N-(6-(4-((1-(2-fluorophenyl)-1H-1,2,3-triazol-4-yl)methyl)
piperazin-1-yl)pyridin-2-yl)cyclopropanesulfonamide,
N-(6-(4-((1-(2-hydroxyphenyl)-1H-1,2,3-triazol-4-yl)
methyl)piperazin-1-yl)pyridin-2-yl)propane-2-sulfona-
mide,
N-(6-(4-((1-(pyridin-2-yl)-1H-pyrazol-4-yl)methyl)piper-
azin-1-yl)pyridin-2-yl)propane-2-sulfonamide,
N-(6-(4-((1-(3,4-difluorophenyl)-1H-1,2,3-triazol-4-yl)
methyl)piperazin-1-yl)pyridin-2-yl)propane-2-sulfona-
mide,
N-(6-(4-((1-(4-chloro-2-fluorophenyl)-1H-1,2,3-triazol-4-
yl)methyl)piperazin-1-yl)pyridin-2-yl)propane-2-sulfo-
namide,
N-(6-(4-((1-phenyl-1H-1,2,3-triazol-4-yl)methyl)piperazin-
1-yl)pyridin-2-yl)cyclopropanesulfonamide,
N-(5-chloro-6-(4-((1-phenyl-1H-1,2,3-triazol-4-yl)methyl)
piperazin-1-yl)pyridin-2-yl)propane-2-sulfonamide,
N-(6-(5-((1-phenyl-1H-1,2,3-triazol-4-yl)methyl)hexahy-
dropyrrolo[3,4-c]pyrrol-2(1H)-yl)pyridin-2-yl)propane-
2-sulfonamide,
N-(6-(4-((1-phenyl-1H-1,2,3-triazol-4-yl)methyl)-1,4-diaz-
epan-1-yl)pyridin-2-yl)propane-2-sulfonamide,
N-(6-(4-((1-(2-fluorophenyl)-1H-1,2,3-triazol-4-yl)
methyl)-1-1,4-diazepan-1-yl)pyridin-2-yl)propane-2-sul-
fonamide,
N-(6-(5-((1-(2-fluorophenyl)-1H-1,2,3-triazol-4-yl)methyl)
hexahydropyrrolo[3,4-c]pyrrol-2(1H)-yl)pyridin-2-yl)
propane-2-sulfonamide, and
N-(6-(4-((1-(pyridin-2-yl)-1H-imidazol-4-yl)methyl)piper-
azin-1-yl)pyridin-2-yl)propane-2-sulfonamide,
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another highly preferred embodiment of the compound according to the invention according to general formulas I, II, III, or IV the compound is selected from
N-(3-(4-((1-phenyl-1H-1,2,3-triazol-4-yl)methyl)piperazin-
1-yl)phenyl)propane-2-sulfonamide, N-(3-(4-((1-(2-fluorophenyl)-1H-1,2,3-triazol-4-yl)methyl)piperazin-1-yl)phenyl)propane-2-sulfonamide, N-(3-(methyl(1-((1-phenyl-1H-1,2,3-triazol-4-yl)methyl)pyrrolidin-3-yl)amino)phenyl)methanesulfonamide, N-(3-(4-((1-phenyl-1H-1,2,3-triazol-4-yl)methyl)piperazin-1-yl)phenyl)cyclopropanesulfonamide, N-(3-(methyl(1-((1-phenyl-1H-1,2,3-triazol-4-yl)methyl)pyrrolidin-3-yl)amino)phenyl)propane-2-sulfonamide, N-(3-(4-((1-(3-fluorophenyl)-1H-1,2,3-triazol-4-yl)methyl)piperazin-1-yl)phenyl)propane-2-sulfonamide, N-(3-(5-((1-phenyl-1H-1,2,3-triazol-4-yl)methyl)hexahydropyrrolo[3,4-c]pyrrol-2(1H)-yl)phenyl)propane-2-sulfonamide, and N-(6-(4-((1-phenyl-1H-1,2,3-triazol-4-yl)methyl)-1,4-diazepan-1-yl)pyridin-2-yl)propane-2-sulfonamide;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, II, III, IV or V the compound is a compound, wherein $R^1$ is hydroxyl, —$NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl and substituted or unsubstituted heterocyclyl, wherein the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline;

and/or most preferably $R^1$ is hydroxyl, —$NR^6R^7$, —$NR^6S(O)_2R^7$, —$NR^6COR^7$, $NR^6CONR^7R^8$, —$S(O)_2R^6$, —$S(O)_2NR^6R^7$, —$CONR^6R^7$, substituted or unsubstituted aryl like phenyl and substituted or unsubstituted heterocyclyl like imidazol;

and/or $R^2$ is hydrogen, halogen (F, Cl, I, Br), —$NR^6R^7$, —$SR^6$, —$OR^6$, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, wherein the aryl is phenyl, naphtyl or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline;

and/or the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl;

and/or the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;

and/or the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;

and/or the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl;

and/or halogen is any of fluorine, chlorine, iodine or bromine, preferably chlorine or fluorine;

and/or most preferably $R^2$ is selected from hydrogen, halogen like fluorine, or $C_{1-4}$alkyl like $CH_3$ or $CF_3$;

and/or $R^1$ and $R^2$ are bonded to neighbouring atoms in the ring and together with these atoms form a saturated or unsaturated, substituted or unsubstituted ring, fused to the ring

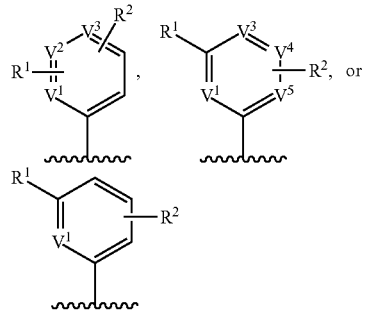

or J of the corestructure of formulas I, II, III, IV, or V respectively, which may be condensed with a further unsubstituted or substituted ring system, wherein the ring is either unsubstituted or substituted by one or more of halogen (F, Cl, I, Br), —OH, —NH$_2$, —SH, =O, —OC$_{1-4}$alkyl being unsubstituted or substituted by one or more of OH or halogen (F, Cl, I, Br), —CN, or C$_{1-4}$alkyl being unsubstituted or substituted by one or more of OH or halogen (F, Cl, I, Br); preferably the ring being formed with V$^1$, V$^2$, V$^3$, V$^4$ and V$^5$ all being carbon is fused with a phenyl ring on the corestructure

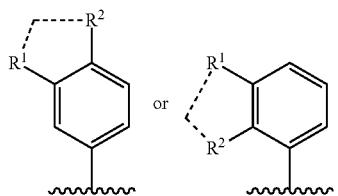

forming a double ring, more preferably forming a heterocyclic double ring, most preferably the heterocyclic double ring formed by R$^1$ and R$^2$ with the corestructure is selected from benzoimidazole, indazole, indoline and benzothiazole being unsubstituted or being substituted by one or more of halogen (F, Cl, I, Br), —OH, —NH$_2$, —SH, =O, —OC$_{1-4}$alkyl being unsubstituted or substituted by one or more of OH or halogen (F, Cl, I, Br), —CN, or C$_{1-4}$alkyl being unsubstituted or substituted by one or more of OH or halogen (F, Cl, I, Br);

and/or

R$^3$ is substituted or unsubstituted alkyl, CONR$^6$R$^7$, substituted or unsubstituted cycloalkyl, substituted or unsubstituted alkenyl, substituted or unsubstituted alkynyl, substituted or unsubstituted aryl and substituted or unsubstituted heterocyclyl, wherein the aryl is phenyl, naphtyl or anthracene; preferably is napthyl and phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, especially is pyridine, imidazole, indene, 2,3-dihydroindene, benzofuran, pyrimidine;
and/or
the alkyl is C$_{1-8}$alkyl like methyl, ethyl, propyl, butyl, pentyl, hexyl, heptyl, or octyl; preferably is C$_{1-6}$alkyl like methyl, ethyl, propyl, butyl, pentyl, or hexyl; more preferably is C$_{1-4}$alkyl like methyl, ethyl, propyl or butyl or R$^3$ is not alkyl;

and/or
the alkenyl is C$_{2-10}$-alkenyl or C$_{2-8}$-alkenyl like ethylene, propylene, butylene, pentylene, hexylene, heptylene or octylene; preferably id C$_{1-6}$-alkenyl like ethylene, propylene, butylene, pentylene, or hexylene; more preferably from C$_{1-4}$-alkenyl, like ethylene, propylene, or butylene;
and/or
the alkynyl is C$_{2-10}$-alkynyl or C$_{2-8}$-alkynyl like ethyne, propyne, butyene, pentyne, hexyne, heptyne, or octyne; preferably is C$_{2-6}$-alkynyl like ethyne, propyne, butyene, pentyne, or hexyne; more preferably is C$_{2-4}$-alkynyl like ethyne, propyne, butyene, pentyne, or hexyne;
and/or
the cycloalkyl is C$_{3-8}$cycloalkyl like cyclopropyl, cyclobutyl, cyclopentyl, cyclohexyl, cycloheptyl, or cyclooctyl; preferably is C$_{3-7}$cycloalkyl like cyclopropyl, cyclobutyl, cyclopentyl, cyclohexyl, or cycloheptyl; more preferably from C$_{3-6}$cycloalkyl like cyclopropyl, cyclobutyl, cyclopentyl or cyclohexyl, especially cyclopentyl or cyclohexyl;
and/or
preferably R$^3$ is not alkyl;
and/or
most preferably R$^3$ is selected from substituted or unsubstituted alkyl like propyl or butyl, CONR$^6$R$^7$ like diethylacetamide, from substituted or unsubstituted cycloalkyl like cyclopentyl or cyclohexyl, or from substituted or unsubstituted aryl, like phenyl, or from substituted or unsubstituted heterocyclyl, like pyridine, imidazole, indene, 2,3-dihydroindene, benzofuran, pyrimidine,
or most preferably R$^3$ is selected from substituted or unsubstituted cycloalkyl like cyclopentyl or cyclohexyl, or from substituted or unsubstituted aryl, like phenyl, or from substituted or unsubstituted heterocyclyl, like pyridine, imidazole, indene, 2,3-dihydroindene, benzofuran, pyrimidine;
and/or
R$^4$ is hydrogen, substituted or unsubstituted alkyl, substituted of unsubstituted cycloalkyl, substituted or unsubstituted alkenyl, substituted or unsubstituted alkynyl, substituted of unsubstituted aryl and substituted of unsubstituted heterocyclyl, wherein
the aryl is phenyl, naphtyl or anthracene; preferably is napthyl and phenyl; more preferably is phenyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, especially is pyridine, imidazole, indene, 2,3-dihydroindene, benzofuran, pyrimidine;

and/or the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl;

and/or the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;

and/or the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;

and/or the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl, especially cyclopentyl or cyclohexyl;

and/or most preferably $R^4$ is selected from hydrogen or from substituted or unsubstituted $C_{1-4}$alkyl like $CH_3$ or $CH_2OH$;

and/or $R^5$ is hydrogen, hydroxy, or $CH_3$, or is only hydrogen or $CH_3$;

and/or $R^6$, $R^7$ and $R^8$ are independent from each other and selected from the group formed by hydrogen, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom may form a cycloalkylic or heterocyclic 4 to 7-membered ring, wherein the aryl is phenyl, naphtyl or anthracene; preferably is napthyl and phenyl; more preferably is phenyl;

and/or the alkyl-aryl is $C_{1-4}$-alkyl-aryl; preferably is benzyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, especially is pyridine, imidazole, indene, 2,3-dihydroindene, benzofuran, pyrimidine;

and/or the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl;

and/or the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;

and/or the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;

and/or the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl, especially cyclopentyl or cyclohexyl;

and/or when $R^6$, $R^7$ or $R^8$ together with their respective connecting carbon or nitrogen atom form a cycloalkylic or heterocyclic ring this ring is 5 or 6 membered, preferably form a saturated cycloalkylic ring of 5 or 6 members, like saturated, unsubstituted cyclohexyl;

and/or most preferably $R^6$, $R^7$, and $R^8$ are independently from each other selected from hydrogen, from substituted or unsubstituted $C_{1-4}$alkyl like methyl, ethyl, propyl or butyl, from substituted or unsubstituted aryl like phenyl, from substituted or unsubstituted heterocyclyl like pyrrolidine, or from substituted or unsubstituted alkyl-aryl like benzyl, or $R^6$ and $R^7$ together with their connecting carbon atom form a cycloalkylic 5 or 6-membered ring like cyclohexyl.

In another preferred embodiment of the compound according to the invention according to general formulas I, II, III, IV or V the compound is a compound, wherein $R^1$ is hydroxyl, —$NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$, —$CONR^6R^7$, substituted or unsubstituted aryl and substituted or unsubstituted heterocyclyl, wherein the aryl is selected from phenyl, naphtyl, or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring, more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline;

and/or most preferably $R^1$ is hydroxyl, —$NR^6R^7$, —$NR^6S(O)_2R^7$, —$NR^6COR^7$, $NR^6CONR^7R^8$, —$S(O)_2R^6$, —$S(O)_2NR^6R^7$, —$CONR^6R^7$, substituted or unsubstituted aryl like phenyl and substituted or unsubstituted heterocyclyl like imidazol.

In another preferred embodiment of the compound according to the invention according to general formulas I, II, III, IV or V the compound is a compound, wherein $R^2$ is hydrogen, halogen (F, Cl, I, Br), —$NR^6R^7$, —$SR^6$, —$OR^6$, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, wherein the aryl is phenyl, naphtyl or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline;

and/or the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl;

and/or the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;

and/or the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;

and/or the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl;

and/or halogen is any of fluorine, chlorine, iodine or bromine, preferably chlorine or fluorine;

and/or most preferably $R^2$ is selected from hydrogen, halogen like fluorine, or $C_{1-4}$alkyl like $CH_3$ or $CF_3$.

In another preferred embodiment of the compound according to the invention according to general formulas I, II, III, IV or V the compound is a compound, wherein $R^1$ and $R^2$ are bonded to neighbouring atoms in the ring and together with these atoms form a saturated or unsaturated, substituted or unsubstituted ring, fused to the ring

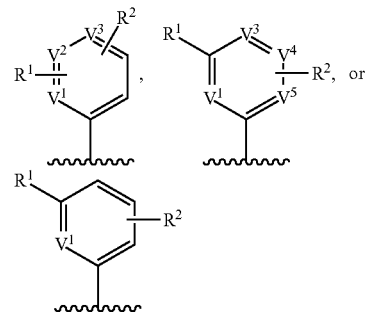

of the corestructure of formulas I, II, III, IV or V respectively, which may be condensed with a further unsubstituted or substituted ring system, wherein the ring is either unsubstituted or substituted by one or more of halogen (F, Cl, I, Br), —OH, —$NH_2$, —SH, =O, —$OC_{1-4}$alkyl being unsubstituted or substituted by one or more of OH or halogen (F, Cl, I, Br), —CN, or $C_{1-4}$alkyl being unsubstituted or substituted by one or more of OH or halogen (F, Cl, I, Br); preferably the ring being formed with $V^1$, $V^2$, $V^3$, $V^4$ and $V^5$ all being carbon is fused with a phenyl ring on the corestructure

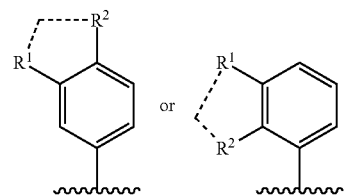

forming a double ring, more preferably forming a heterocyclic double ring, most preferably the heterocyclic double ring formed by $R^1$ and $R^2$ with the corestructure is selected from benzoimidazole, indazole, indoline and benzothiazole being unsubstituted or being substituted by one or more of halogen (F, Cl, I, Br), —OH, —$NH_2$, —SH, =O, —$OC_{1-4}$ alkyl being unsubstituted or substituted by one or more of OH or halogen (F, Cl, I, Br), —CN, or $C_{1-4}$alkyl being unsubstituted or substituted by one or more of OH or halogen (F, Cl, I, Br).

In another preferred embodiment of the compound according to the invention according to general formulas I, II, III, IV or V the compound is a compound, wherein R³ is substituted or unsubstituted alkyl, CONR⁶R⁷, substituted or unsubstituted cycloalkyl, substituted or unsubstituted alkenyl, substituted or unsubstituted alkynyl, substituted or unsubstituted aryl and substituted or unsubstituted heterocyclyl, wherein the aryl is phenyl, naphtyl or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, especially is pyridine, imidazole, indene, 2,3-dihydroindene, benzofuran, pyrimidine;

and/or the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl or R³ is not alkyl;

and/or the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;

and/or the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;

and/or the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl, especially cyclopentyl or cyclohexyl;

and/or preferably R³ is not alkyl;

and/or most preferably R³ is selected from substituted or unsubstituted alkyl like propyl or butyl, CONR⁶R⁷ like diethylacetamide, from substituted or unsubstituted cycloalkyl like cyclopentyl or cyclohexyl, or from substituted or unsubstituted aryl, like phenyl, or from substituted or unsubstituted heterocyclyl, like pyridine, imidazole, indene, 2,3-dihydroindene, benzofuran, pyrimidine, or most preferably R³ is selected from substituted or unsubstituted cycloalkyl like cyclopentyl or cyclohexyl, or from substituted or unsubstituted aryl, like phenyl, or from substituted or unsubstituted heterocyclyl, like pyridine, imidazole, indene, 2,3-dihydroindene, benzofuran, pyrimidine.

In another preferred embodiment of the compound according to the invention according to general formulas I, II, III, IV or V the compound is a compound, wherein R⁴ is hydrogen, substituted or unsubstituted alkyl, substituted of unsubstituted cycloalkyl, substituted or unsubstituted alkenyl, substituted or unsubstituted alkynyl, substituted of unsubstituted aryl and substituted of unsubstituted heterocyclyl, wherein the aryl is phenyl, naphtyl or anthracene; preferably is napthyl and phenyl; more preferably is phenyl;

and/or the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, especially is pyridine, imidazole, indene, 2,3-dihydroindene, benzofuran, pyrimidine;

and/or the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl;

and/or the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;

and/or the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;

and/or the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl, especially cyclopentyl or cyclohexyl;

and/or
most preferably $R^4$ is selected from hydrogen or from substituted or unsubstituted $C_{1-4}$alkyl like $CH_3$ or $CH_2OH$.

In another preferred embodiment of the compound according to the invention according to general formulas I, II, III, IV or V the compound is a compound, wherein $R^5$ is hydrogen, hydroxy, or $CH_3$, or is only hydrogen or $CH_3$.

In another preferred embodiment of the compound according to the invention according to general formulas I, II, III, IV or V the compound is a compound, wherein $R^6$, $R^7$ and $R^8$ are independent from each other and selected from the group formed by hydrogen, substituted or unsubstituted alkyl, substituted of unsubstituted cycloalkyl, substituted or unsubstituted alkenyl, substituted or unsubstituted alkynyl, substituted or unsubstituted aryl and substituted or unsubstituted heterocyclyl, or $R^6$, $R^7$ or $R^8$ together with their respective connecting carbon or nitrogen atom may form a cycloalkylic or heterocyclic 4 to 7-membered ring, wherein
the aryl is phenyl, naphtyl or anthracene; preferably is napthyl and phenyl; more preferably is phenyl;
and/or
the alkyl-aryl is $C_{1-4}$-alkyl-aryl; preferably is benzyl;
and/or
the heterocyclyl is a heterocyclic ring system of one or more saturated or unsaturated rings of which at least one ring contains one or more heteroatoms from the group consisting of nitrogen, oxygen and/or sulfur in the ring; preferably is a heterocyclic ring system of one or two saturated or unsaturated rings of which at least one ring contains one or more heteroatoms from the group consisting of nitrogen, oxygen and/or sulfur in the ring; more preferably is selected from imidazole, oxadiazole, tetrazole, pyridine, pyrimidine, piperidine, indene, 2,3-dihydroindene, benzofuran, benzimidazole, indazole, benzothiazole, indoline, furan, triazole, isoxazole, pyrazole, thiophene, benzothiophene, pyrrole, pyrazine, quinoline, isoquinoline, phthalazine, benzo-1,2,5-thiadiazole, indole, benzotriazole, benzodioxolane, benzodioxane, carbazole and quinazoline, especially is pyridine, imidazole, indene, 2,3-dihydroindene, benzofuran, pyrimidine;
and/or
the alkyl is $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl;
and/or
the alkenyl is $C_{2-10}$-alkenyl or $C_{2-8}$-alkenyl like ethylene, propylene, butylene, pentylene, hexylene, heptylene or octylene; preferably id $C_{1-6}$-alkenyl like ethylene, propylene, butylene, pentylene, or hexylene; more preferably from $C_{1-4}$-alkenyl, like ethylene, propylene, or butylene;
and/or
the alkynyl is $C_{2-10}$-alkynyl or $C_{2-8}$-alkynyl like ethyne, propyne, butyene, pentyne, hexyne, heptyne, or octyne; preferably is $C_{2-6}$-alkynyl like ethyne, propyne, butyene, pentyne, or hexyne; more preferably is $C_{2-4}$-alkynyl like ethyne, propyne, butyene, pentyne, or hexyne;

and/or
the cycloalkyl is $C_{3-8}$cycloalkyl like cyclopropyl, cyclobutyl, cyclopentyl, cyclohexyl, cycloheptyl, or cyclooctyl; preferably is $C_{3-7}$cycloalkyl like cyclopropyl, cyclobutyl, cyclopentyl, cyclohexyl, or cycloheptyl; more preferably from $C_{3-6}$cycloalkyl like cyclopropyl, cyclobutyl, cyclopentyl or cyclohexyl, especially cyclopentyl or cyclohexyl;
and/or
when $R^6$, $R^7$ or $R^8$ together with their respective connecting carbon or nitrogen atom form a cycloalkylic or heterocyclic ring this ring is 5 or 6 membered, preferably form a saturated cycloalkylic ring of 5 or 6 members, like saturated, unsubstituted cyclohexyl;
and/or
most preferably $R^6$, $R^7$, and $R^8$ are independently from each other selected from hydrogen, from substituted or unsubstituted $C_{1-4}$alkyl like methyl, ethyl, propyl or butyl, from substituted or unsubstituted aryl like phenyl, from substituted or unsubstituted heterocyclyl like pyrrolidine, or from substituted or unsubstituted alkyl-aryl like benzyl, or $R^6$ and $R^7$ together with their connecting carbon atom form a cycloalkylic 5 or 6-membered ring like cyclohexyl.

In another preferred embodiment of the compound according to the invention according to general formulas I, II, III, IV or V the compound is a compound, wherein
m is 1 or 2;
n is 0 or 1;
$V^1$ is selected from nitrogen or carbon;
$R^1$ is hydroxyl, $—NR^6R^7$, $—NR^6S(O)_2R^7$, $—NR^6COR^7$, $—NR^6CONR^7R^8$, $—S(O)_2R^6$, $—S(O)_2NR^6R^7$, $—CONR^6R^7$, substituted or unsubstituted aryl and substituted or unsubstituted heterocyclyl;
$R^2$ is hydrogen, halogen like fluorine, or $C_{1-4}$alkyl like $CH_3$ or $CF_3$, preferably is hydrogen;
or
$R^1$ and $R^2$ form a heterocyclic double ring with the corestructure, preferably being selected from benzoimidazole, indazole, indoline and benzothiazole being unsubstituted or being substituted by one or more of halogen (F, Cl, I, Br), $—OH$, $—NH_2$, $—SH$, $=O$, $—OC_{1-4}$alkyl being unsubstituted or substituted by one or more of OH or halogen (F, Cl, I, Br), $—CN$, or $C_{1-4}$alkyl being unsubstituted or substituted by one or more of OH or halogen (F, Cl, I, Br);
$R^3$ is selected from substituted or unsubstituted cycloalkyl like cyclopentyl or cyclohexyl, or from substituted or unsubstituted aryl, like phenyl, or from substituted or unsubstituted heterocyclyl, like pyridine, imidazole, indene, 2,3-dihydroindene, benzofuran, pyrimidine;
$R^4$ is hydrogen or substituted or unsubstituted $C_{1-4}$alkyl like $CH_3$ or $CH_2OH$;
$R^5$ is hydrogen, hydroxy, or $CH_3$, preferably hydrogen;
$R^6$, $R^7$, and $R^8$ are independently from each other selected from hydrogen, from substituted or unsubstituted $C_{1-4}$alkyl like methyl, ethyl, propyl, isopropyl, tert-butyl or butyl, from substituted or unsubstituted aryl like phenyl, from substituted or unsubstituted heterocyclyl like pyrrolidine, or from substituted or unsubstituted alkyl-aryl like benzyl, or $R^6$ and $R^7$ together with their connecting carbon atom form a cycloalkylic 5 or 6-membered ring like cyclohexyl.

In another preferred embodiment of the compound according to the invention according to general formulas I, II, III, IV or V the compound is a compound, wherein
m is 1.

In another preferred embodiment of the compound according to the invention according to general formulas I, II, III, IV or V the compound is a compound, wherein
n is 0 or 1.

In another preferred embodiment of the compound according to the invention according to general formulas I, II, III, IV or V the compound is a compound, wherein
$V^1$ is selected from nitrogen and carbon.

In another preferred embodiment of the compound according to the invention according to general formulas I, II, III, IV or V the compound is a compound, wherein
$R^1$ is hydroxyl, —$NH_2$, —$NHS(O)_2$-isopropyl, —$NHS(O)_2$-methyl, —$NHS(O)_2$-ethyl, —$NHS(O)_2$-cyclopropyl, —$NHS(O)_2$—$CF_3$, —$S(O)_2NH$-tert-butyl, $NHC(O)$-ethyl.

In another preferred embodiment of the compound according to the invention according to general formulas I, II, III, IV or V the compound is a compound, wherein
$R^2$ is hydrogen.

In another preferred embodiment of the compound according to the invention according to general formulas I, II, III, IV or V the compound is a compound, wherein
$R^3$ is selected from substituted or unsubstituted phenyl and from substituted or unsubstituted pyrimidine.

In another preferred embodiment of the compound according to the invention according to general formulas I, II, III, IV or V the compound is a compound, wherein
$R^4$ is hydrogen.

In another preferred embodiment of the compound according to the invention according to general formulas I, II, III, IV or V the compound is a compound, wherein
$R^5$ is hydrogen.

In another preferred embodiment of the compound according to the invention according to general formulas I, II, III, IV or V the compound is a compound, wherein
$R^6$ is hydrogen.

In another preferred embodiment of the compound according to the invention according to general formulas I, II, III, IV or V the compound is a compound, wherein
$R^7$ is hydrogen, substituted or unsubstituted methyl, substituted or unsubstituted ethyl, substituted or unsubstituted isopropyl, substituted or unsubstituted tert-butyl, substituted or unsubstituted cyclopropyl or —$CF_3$.

In another preferred embodiment of the compound according to the invention according to general formulas I, II or III the compound is a compound, wherein

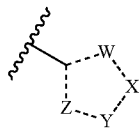

is substituted triazole, substituted pyrazole or substituted imidazole, preferably selected from

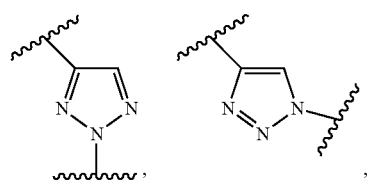

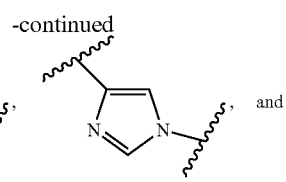

In another preferred embodiment of the compound according to the invention according to general formulas I, II or III, IV or V the compound is a compound, wherein

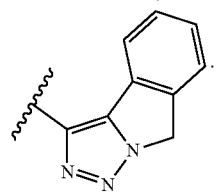

is selected from

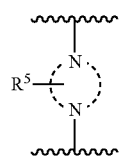

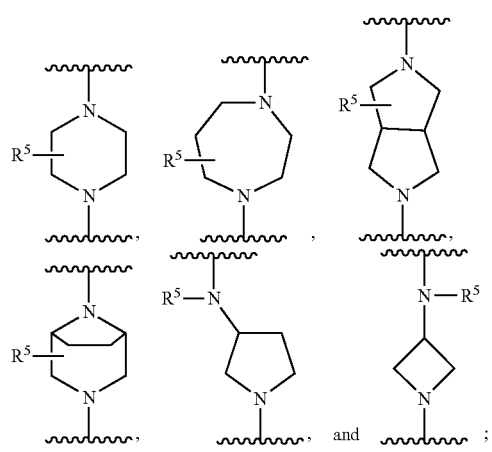

In another very preferred embodiment of the compound according to the invention according to general Formula IV, the compound is a compound, wherein
m is 1 or 2;
n is 0 or 1;
$V^1$ is selected from nitrogen or carbon;
$R^1$ is hydroxyl, —$NR^6R^7$, —$NR^6S(O)_2R^7$, —$NR^6COR^7$, —$NR^6CONR^7R^8$, —$S(O)_2R^6$, —$S(O)_2NR^6R^7$, —$CONR^6R^7$, substituted or unsubstituted phenyl and substituted or unsubstituted imidazol, preferably is hydroxyl, $NR^6R^7$, $S(O)_2NR^6R^7$, $NR^6COR^7$ and —$NR^6S(O)_2R^7$;
$R^2$ is hydrogen;
or
$R^3$ is selected from substituted or unsubstituted cyclopentyl, cyclohexyl, or from substituted or unsubstituted phenyl, or from substituted or unsubstituted heterocyclyl, like pyridine, imidazole, indene, 2,3-dihydroindene, benzofuran, pyrimidine; preferably is phenyl or pyridine;

R[4] is hydrogen or substituted or unsubstituted $C_{1-4}$alkyl, preferably is hydrogen;

R[5] is hydrogen, hydroxy, or $CH_3$, preferably is hydrogen or $CH_3$, more preferably hydrogen;

R[6], R[7] and R[8] are independent from each other and selected from the group formed by hydrogen, substituted or unsubstituted alkyl, substituted of unsubstituted cycloalkyl, substituted or unsubstituted phenyl, preferably are selected from hydrogen, substituted or unsubstituted $C_{1-4}$alkyl, substituted of unsubstituted $C_{3-6}$cycloalkyl;

and W, Y and Z are independently from one another selected from N or CH with only 1 or 2 of them being CH;

and wherein

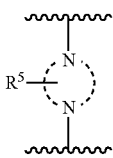

is selected from

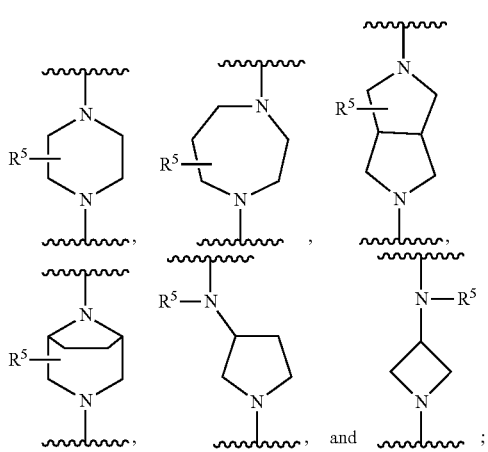

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, II, III, or IV the compound is selected from N-(3-(4-((1-phenyl-1H-1,2,3-triazol-4-yl)methyl)piperazin-1-yl)phenyl)propane-2-sulfonamide, N-(6-(4-((1-(5-chloropyridin-3-yl)-1H-1,2,3-triazol-4-yl)methyl)piperazin-1-yl)pyridin-2-yl)propane-2-sulfonamide, N-(3-(4-((1-benzyl-1H-1,2,3-triazol-4-yl)methyl)piperazin-1-yl)phenyl)methanesulfonamide, N-(3-(4-((1-phenyl-1H-1,2,3-triazol-4-yl)methyl)piperazin-1-yl)phenyl)methanesulfonamide, 3-(4-((1-phenyl-1H-1,2,3-triazol-4-yl)methyl)piperazin-1-yl)phenol, 3-(4-((1-benzyl-1H-1,2,3-triazol-4-yl)methyl)piperazin-1-yl)phenol, 3-(4-((1-(pyridin-2-yl)-1H-1,2,3-triazol-4-yl)methyl)piperazin-1-yl)phenol, N-(3-(4-((1-(6-(trifluoromethyl)pyridin-3-yl)-1H-1,2,3-triazol-4-yl)methyl)piperazin-1-yl)phenyl)methanesulfonamide, N-(3-(4-((1-(2-fluorophenyl)-1H-1,2,3-triazol-4-yl)methyl)piperazin-1-yl)phenyl)propane-2-sulfonamide, N-(3-(4-((1-phenyl-1H-1,2,3-triazol-4-yl)methyl)piperazin-1-yl)phenyl)ethanesulfonamide, N-(3-(1-((1-phenyl-1H-1,2,3-triazol-4-yl)methyl)pyrrolidin-3-ylamino)phenyl)methanesulfonamide, N-(3-(1-((1-phenyl-1H-1,2,3-triazol-4-yl)methyl)azetidin-3-ylamino)phenyl)methanesulfonamide, N-(3-(5-((1-phenyl-1H-1,2,3-triazol-4-yl)methyl)hexahydropyrrolo[3,4-c]pyrrol-2(1H)-yl)phenyl)methanesulfonamide, N-(3-(methyl(1-((1-phenyl-1H-1,2,3-triazol-4-yl)methyl)pyrrolidin-3-yl)amino)phenyl)methanesulfonamide, N-(3-(methyl(1-((1-phenyl-1H-1,2,3-triazol-4-yl)methyl)azetidin-3-yl)amino)phenyl)methanesulfonamide, N-(3-(4-((1-(pyridin-2-ylmethyl)-1H-1,2,3-triazol-4-yl)methyl)piperazin-1-yl)phenyl)propane-2-sulfonamide, N-(3-(4-((1-(pyridin-2-yl)-1H-1,2,3-triazol-4-yl)methyl)piperazin-1-yl)phenyl)propane-2-sulfonamide, 1,1,1-trifluoro-N-(3-(4-((1-phenyl-1H-1,2,3-triazol-4-yl)methyl)piperazin-1-yl)phenyl)methanesulfonamide, N-(3-(4-((1-(5-fluoropyridin-2-yl)-1H-1,2,3-triazol-4-yl)methyl)piperazin-1-yl)phenyl)propane-2-sulfonamide, N-(3-(4-((1-phenyl-1H-1,2,3-triazol-4-yl)methyl)piperazin-1-yl)phenyl)cyclopropanesulfonamide, N-(3-(4-((1-(3-fluoropyridin-2-yl)-1H-1,2,3-triazol-4-yl)methyl)piperazin-1-yl)phenyl)propane-2-sulfonamide, N-(3-(4-((1-(4-fluoropyridin-2-yl)-1H-1,2,3-triazol-4-yl)methyl)piperazin-1-yl)phenyl)propane-2-sulfonamide, N-(3-((1R,5S)-3-((1-phenyl-1H-1,2,3-triazol-4-yl)methyl)-3,8-diazabicyclo[3.2.1]octan-8-yl)phenyl)methanesulfonamide, N-(3-(4-((2-(pyridin-2-yl)-2H-1,2,3-triazol-4-yl)methyl)piperazin-1-yl)phenyl)propane-2-sulfonamide, N-(3-(4-((1-phenyl-1H-1,2,3-triazol-4-yl)methyl)-1,4-diazepan-1-yl)phenyl)methanesulfonamide, N-(3-(methyl(1-((1-phenyl-1H-1,2,3-triazol-4-yl)methyl)pyrrolidin-3-yl)amino)phenyl)propane-2-sulfonamide, N-(3-(4-((1-(3-fluorophenyl)-1H-1,2,3-triazol-4-yl)methyl)piperazin-1-yl)phenyl)propane-2-sulfonamide, N-(3-(4-((1-(4-fluorophenyl)-1H-1,2,3-triazol-4-yl)methyl)piperazin-1-yl)phenyl)propane-2-sulfonamide, N-(3-(4-((1-(6-fluoropyridin-2-yl)-1H-1,2,3-triazol-4-yl)methyl)piperazin-1-yl)phenyl)propane-2-sulfonamide, N-(3-(5-((1-phenyl-1H-1,2,3-triazol-4-yl)methyl)hexahydropyrrolo[3,4-c]pyrrol-2(1H)-yl)phenyl)propane-2-sulfonamide, 3-(4-((1-phenyl-1H-1,2,3-triazol-4-yl)methyl)piperazin-1-yl)aniline, N-tert-butyl-3-(4-((1-phenyl-1H-1,2,3-triazol-4-yl)methyl)piperazin-1-yl)benzenesulfonamide, N-(3-(4-((1-phenyl-1H-pyrazol-4-yl)methyl)piperazin-1-yl)phenyl)methanesulfonamide, N-(3-(4-((1-benzyl-1H-pyrazol-4-yl)methyl)piperazin-1-yl)phenyl)methanesulfonamide, N-(3-(4-((1-(pyridin-2-ylmethyl)-1H-pyrazol-4-yl)methyl)piperazin-1-yl)phenyl)methanesulfonamide, N-(3-(4-((1-phenyl-1H-pyrazol-4-yl)methyl)piperazin-1-yl)phenyl)propane-2-sulfonamide, 3-(4-((1-phenyl-1H-pyrazol-4-yl)methyl)piperazin-1-yl)phenol, N-(3-(4-((1-(pyridin-2-yl)-1H-pyrazol-4-yl)methyl)piperazin-1-yl)phenyl)methanesulfonamide,
N-(3-(4-((1-(pyridin-2-yl)-1H-pyrazol-4-yl)methyl)piperazin-1-yl)phenyl)propane-2-sulfonamide,
N-(3-(4-((1-benzyl-1H-imidazol-4-yl)methyl)piperazin-1-yl)phenyl)propane-2-sulfonamide,
N-(6-(4-((1-phenyl-1H-1,2,3-triazol-4-yl)methyl)piperazin-1-yl)pyridin-2-yl)methanesulfonamide,
N-(6-(4-((1-phenyl-1H-1,2,3-triazol-4-yl)methyl)piperazin-1-yl)pyridin-2-yl)propane-2-sulfonamide,
N-(6-(4-((1-(2-fluorophenyl)-1H-1,2,3-triazol-4-yl)methyl)piperazin-1-yl)pyridin-2-yl)propane-2-sulfonamide,
N-(6-(4-((1-(2-fluorophenyl)-1H-1,2,3-triazol-4-yl)methyl)piperazin-1-yl)pyridin-2-yl)cyclopropanesulfonamide,
N-(6-(4-((1-(2-fluorophenyl)-1H-1,2,3-triazol-4-yl)methyl)piperazin-1-yl)pyridin-2-yl)propionamide,
N-(6-(4-((1-(2-hydroxyphenyl)-1H-1,2,3-triazol-4-yl)methyl)piperazin-1-yl)pyridin-2-yl)propane-2-sulfonamide,
N-(6-(4-((1-(pyridin-2-yl)-1H-pyrazol-4-yl)methyl)piperazin-1-yl)pyridin-2-yl)propane-2-sulfonamide,
N-(6-(4-((1-(2,6-difluorophenyl)-1H-1,2,3-triazol-4-yl)methyl)piperazin-1-yl)pyridin-2-yl)propane-2-sulfonamide,
N-(6-(4-((1-(3,4-difluorophenyl)-1H-1,2,3-triazol-4-yl)methyl)piperazin-1-yl)pyridin-2-yl)propane-2-sulfonamide,
N-(6-(4-((1-(4-chloro-2-fluorophenyl)-1H-1,2,3-triazol-4-yl)methyl)piperazin-1-yl)pyridin-2-yl)propane-2-sulfonamide,
N-(6-(4-((1-phenyl-1H-1,2,3-triazol-4-yl)methyl)piperazin-1-yl)pyridin-2-yl)cyclopropanesulfonamide,
N-(5-chloro-6-(4-((1-phenyl-1H-1,2,3-triazol-4-yl)methyl)piperazin-1-yl)pyridin-2-yl)propane-2-sulfonamide,
N-(6-(5-((1-phenyl-1H-1,2,3-triazol-4-yl)methyl)hexahydropyrrolo[3,4-c]pyrrol-2(1H)-yl)pyridin-2-yl)propane-2-sulfonamide,
N-(6-(5-((1-benzyl-1H-1,2,3-triazol-4-yl)methyl)hexahydropyrrolo[3,4-c]pyrrol-2(1H)-yl)pyridin-2-yl)propane-2-sulfonamide,
N-(6-(5-((1-(pyridin-2-ylmethyl)-1H-1,2,3-triazol-4-yl)methyl)hexahydropyrrolo[3,4-c]pyrrol-2(1H)-yl)pyridin-2-yl)propane-2-sulfonamide,
N-(6-(4-((1-(5-methoxypyridin-3-yl)-1H-1,2,3-triazol-4-yl)methyl)piperazin-1-yl)pyridin-2-yl)propane-2-sulfonamide,
N-(6-(4-((1-phenyl-1H-1,2,3-triazol-4-yl)methyl)-1,4-diazepan-1-yl)pyridin-2-yl)propane-2-sulfonamide,
N-(6-(4-((1-(5-chloropyridin-2-yl)-1H-1,2,3-triazol-4-yl)methyl)piperazin-1-yl)pyridin-2-yl)propane-2-sulfonamide,
N-(6-(4-((1-(pyridin-2-ylmethyl)-1H-1,2,3-triazol-4-yl)methyl)-1,4-diazepan-1-yl)pyridin-2-yl)propane-2-sulfonamide,
N-(6-(4-((1-(2-fluorophenyl)-1H-1,2,3-triazol-4-yl)methyl)-1-1,4-diazepan-1-yl)pyridin-2-yl)propane-2-sulfonamide,
N-(6-(5-((1-(2-fluorophenyl)-1H-1,2,3-triazol-4-yl)methyl)hexahydropyrrolo[3,4-c]pyrrol-2(1H)-yl)pyridin-2-yl)propane-2-sulfonamide, and
N-(6-(4-((1-(pyridin-2-yl)-1H-imidazol-4-yl)methyl)piperazin-1-yl)pyridin-2-yl)propane-2-sulfonamide;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another very preferred embodiment of the compound according to the invention according to general formulas I, II, III, or IV the compound is selected from
N-(3-(4-((1-phenyl-1H-1,2,3-triazol-4-yl)methyl)piperazin-1-yl)phenyl)propane-2-sulfonamide,
N-(6-(4-((1-(5-chloropyridin-3-yl)-1H-1,2,3-triazol-4-yl)methyl)piperazin-1-yl)pyridin-2-yl)propane-2-sulfonamide,
N-(3-(4-((1-benzyl-1H-1,2,3-triazol-4-yl)methyl)piperazin-1-yl)phenyl)methanesulfonamide,
N-(3-(4-((1-phenyl-1H-1,2,3-triazol-4-yl)methyl)piperazin-1-yl)phenyl)methanesulfonamide,
3-(4-((1-phenyl-1H-1,2,3-triazol-4-yl)methyl)piperazin-1-yl)phenol,
3-(4-((1-benzyl-1H-1,2,3-triazol-4-yl)methyl)piperazin-1-yl)phenol,
3-(4-((1-(pyridin-2-yl)-1H-1,2,3-triazol-4-yl)methyl)piperazin-1-yl)phenol,
N-(3-(4-((1-(2-fluorophenyl)-1H-1,2,3-triazol-4-yl)methyl)piperazin-1-yl)phenyl)propane-2-sulfonamide,
N-(3-(4-((1-phenyl-1H-1,2,3-triazol-4-yl)methyl)piperazin-1-yl)phenyl)ethanesulfonamide,
N-(3-(1-((1-phenyl-1H-1,2,3-triazol-4-yl)methyl)pyrrolidin-3-ylamino)phenyl)methanesulfonamide,
N-(3-(1-((1-phenyl-1H-1,2,3-triazol-4-yl)methyl)azetidin-3-ylamino)phenyl)methanesulfonamide,
N-(3-(5-((1-phenyl-1H-1,2,3-triazol-4-yl)methyl)hexahydropyrrolo[3,4-c]pyrrol-2(1H)-yl)phenyl)methanesulfonamide,
N-(3-(methyl(1-((1-phenyl-1H-1,2,3-triazol-4-yl)methyl)pyrrolidin-3-yl)amino)phenyl)methanesulfonamide,
N-(3-(methyl(1-((1-phenyl-1H-1,2,3-triazol-4-yl)methyl)azetidin-3-yl)amino)phenyl)methanesulfonamide,
N-(3-(4-((1-(pyridin-2-ylmethyl)-1H-1,2,3-triazol-4-yl)methyl)piperazin-1-yl)phenyl)propane-2-sulfonamide,
N-(3-(4-((1-(pyridin-2-yl)-1H-1,2,3-triazol-4-yl)methyl)piperazin-1-yl)phenyl)propane-2-sulfonamide,
N-(3-(4-((1-(5-fluoropyridin-2-yl)-1H-1,2,3-triazol-4-yl)methyl)piperazin-1-yl)phenyl)propane-2-sulfonamide,
N-(3-(4-((1-phenyl-1H-1,2,3-triazol-4-yl)methyl)piperazin-1-yl)phenyl)cyclopropanesulfonamide,
N-(3-(4-((1-(3-fluoropyridin-2-yl)-1H-1,2,3-triazol-4-yl)methyl)piperazin-1-yl)phenyl)propane-2-sulfonamide,
N-(3-(4-((1-(4-fluoropyridin-2-yl)-1H-1,2,3-triazol-4-yl)methyl)piperazin-1-yl)phenyl)propane-2-sulfonamide,
N-(3-((1R,5S)-3-((1-phenyl-1H-1,2,3-triazol-4-yl)methyl)-3,8-diazabicyclo[3.2.1]octan-8-yl)phenyl)methanesulfonamide,
N-(3-(4-((2-(pyridin-2-yl)-2H-1,2,3-triazol-4-yl)methyl)piperazin-1-yl)phenyl)propane-2-sulfonamide,
N-(3-(4-((1-phenyl-1H-1,2,3-triazol-4-yl)methyl)-1,4-diazepan-1-yl)phenyl)methanesulfonamide,
N-(3-(methyl(1-((1-phenyl-1H-1,2,3-triazol-4-yl)methyl)pyrrolidin-3-yl)amino)phenyl)propane-2-sulfonamide,
N-(3-(4-((1-(3-fluorophenyl)-1H-1,2,3-triazol-4-yl)methyl)piperazin-1-yl)phenyl)propane-2-sulfonamide,
N-(3-(4-((1-(4-fluorophenyl)-1H-1,2,3-triazol-4-yl)methyl)piperazin-1-yl)phenyl)propane-2-sulfonamide,
N-(3-(4-((1-(6-fluoropyridin-2-yl)-1H-1,2,3-triazol-4-yl)methyl)piperazin-1-yl)phenyl)propane-2-sulfonamide,
N-(3-(5-((1-phenyl-1H-1,2,3-triazol-4-yl)methyl)hexahydropyrrolo[3,4-c]pyrrol-2(1H)-yl)phenyl)propane-2-sulfonamide, N-tert-butyl-3-(4-((1-phenyl-1H-1,2,3-triazol-4-yl)methyl)piperazin-1-yl)benzenesulfonamide,
N-(3-(4-((1-phenyl-1H-pyrazol-4-yl)methyl)piperazin-1-yl)phenyl)methanesulfonamide,
N-(3-(4-((1-benzyl-1H-pyrazol-4-yl)methyl)piperazin-1-yl)phenyl)methanesulfonamide,
N-(3-(4-((1-(pyridin-2-ylmethyl)-1H-pyrazol-4-yl)methyl)piperazin-1-yl)phenyl)methanesulfonamide,
N-(3-(4-((1-phenyl-1H-pyrazol-4-yl)methyl)piperazin-1-yl)phenyl)propane-2-sulfonamide,
3-(4-((1-phenyl-1H-pyrazol-4-yl)methyl)piperazin-1-yl)phenol,
N-(3-(4-((1-(pyridin-2-yl)-1H-pyrazol-4-yl)methyl)piperazin-1-yl)phenyl)methanesulfonamide,
N-(3-(4-((1-(pyridin-2-yl)-1H-pyrazol-4-yl)methyl)piperazin-1-yl)phenyl)propane-2-sulfonamide,
N-(3-(4-((1-benzyl-1H-imidazol-4-yl)methyl)piperazin-1-yl)phenyl)propane-2-sulfonamide,
N-(6-(4-((1-phenyl-1H-1,2,3-triazol-4-yl)methyl)piperazin-1-yl)pyridin-2-yl)methanesulfonamide,
N-(6-(4-((1-phenyl-1H-1,2,3-triazol-4-yl)methyl)piperazin-1-yl)pyridin-2-yl)propane-2-sulfonamide,
N-(6-(4-((1-(2-fluorophenyl)-1H-1,2,3-triazol-4-yl)methyl)piperazin-1-yl)pyridin-2-yl)propane-2-sulfonamide,
N-(6-(4-((1-(2-fluorophenyl)-1H-1,2,3-triazol-4-yl)methyl)piperazin-1-yl)pyridin-2-yl)cyclopropanesulfonamide,
N-(6-(4-((1-(2-fluorophenyl)-1H-1,2,3-triazol-4-yl)methyl)piperazin-1-yl)pyridin-2-yl)propionamide,
N-(6-(4-((1-(2-hydroxyphenyl)-1H-1,2,3-triazol-4-yl)methyl)piperazin-1-yl)pyridin-2-yl)propane-2-sulfonamide,
N-(6-(4-((1-(pyridin-2-yl)-1H-pyrazol-4-yl)methyl)piperazin-1-yl)pyridin-2-yl)propane-2-sulfonamide,
N-(6-(4-((1-(2,6-difluorophenyl)-1H-1,2,3-triazol-4-yl)methyl)piperazin-1-yl)pyridin-2-yl)propane-2-sulfonamide,
N-(6-(4-((1-(3,4-difluorophenyl)-1H-1,2,3-triazol-4-yl)methyl)piperazin-1-yl)pyridin-2-yl)propane-2-sulfonamide,
N-(6-(4-((1-(4-chloro-2-fluorophenyl)-1H-1,2,3-triazol-4-yl)methyl)piperazin-1-yl)pyridin-2-yl)propane-2-sulfonamide,
N-(6-(4-((1-phenyl-1H-1,2,3-triazol-4-yl)methyl)piperazin-1-yl)pyridin-2-yl)cyclopropanesulfonamide,
N-(5-chloro-6-(4-((1-phenyl-1H-1,2,3-triazol-4-yl)methyl)piperazin-1-yl)pyridin-2-yl)propane-2-sulfonamide,
N-(6-(5-((1-phenyl-1H-1,2,3-triazol-4-yl)methyl)hexahydropyrrolo[3,4-c]pyrrol-2(1H)-yl)pyridin-2-yl)propane-2-sulfonamide,
N-(6-(5-((1-benzyl-1H-1,2,3-triazol-4-yl)methyl)hexahydropyrrolo[3,4-c]pyrrol-2(1H)-yl)pyridin-2-yl)propane-2-sulfonamide,
N-(6-(5-((1-(pyridin-2-ylmethyl)-1H-1,2,3-triazol-4-yl)methyl)hexahydropyrrolo[3,4-c]pyrrol-2(1H)-yl)pyridin-2-yl)propane-2-sulfonamide,
N-(6-(4-((1-(5-methoxypyridin-3-yl)-1H-1,2,3-triazol-4-yl)methyl)piperazin-1-yl)pyridin-2-yl)propane-2-sulfonamide,
N-(6-(4-((1-phenyl-1H-1,2,3-triazol-4-yl)methyl)-1,4-diazepan-1-yl)pyridin-2-yl)propane-2-sulfonamide,
N-(6-(4-((1-(5-chloropyridin-2-yl)-1H-1,2,3-triazol-4-yl)methyl)piperazin-1-yl)pyridin-2-yl)propane-2-sulfonamide,
N-(6-(4-((1-(pyridin-2-ylmethyl)-1H-1,2,3-triazol-4-yl)methyl)-1,4-diazepan-1-yl)pyridin-2-yl)propane-2-sulfonamide,
N-(6-(4-((1-(2-fluorophenyl)-1H-1,2,3-triazol-4-yl)methyl)-1-1,4-diazepan-1-yl)pyridin-2-yl)propane-2-sulfonamide,
N-(6-(5-((1-(2-fluorophenyl)-1H-1,2,3-triazol-4-yl)methyl)hexahydropyrrolo[3,4-c]pyrrol-2(1H)-yl)pyridin-2-yl)propane-2-sulfonamide, and
N-(6-(4-((1-(pyridin-2-yl)-1H-imidazol-4-yl)methyl)piperazin-1-yl)pyridin-2-yl)propane-2-sulfonamide;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention according to general formulas I, II, III, or IV the compound is selected from
N-(3-(4-((1-phenyl-1H-1,2,3-triazol-4-yl)methyl)piperazin-1-yl)phenyl)propane-2-sulfonamide,
N-(3-(4-((1-phenyl-1H-1,2,3-triazol-4-yl)methyl)piperazin-1-yl)phenyl)methanesulfonamide,
3-(4-((1-benzyl-1H-1,2,3-triazol-4-yl)methyl)piperazin-1-yl)phenol,
N-(3-(4-((1-(2-fluorophenyl)-1H-1,2,3-triazol-4-yl)methyl)piperazin-1-yl)phenyl)propane-2-sulfonamide,
N-(3-(4-((1-phenyl-1H-1,2,3-triazol-4-yl)methyl)piperazin-1-yl)phenyl)ethanesulfonamide,
N-(3-(1-((1-phenyl-1H-1,2,3-triazol-4-yl)methyl)pyrrolidin-3-ylamino)phenyl)methanesulfonamide,
N-(3-(1-((1-phenyl-1H-1,2,3-triazol-4-yl)methyl)azetidin-3-ylamino)phenyl)methanesulfonamide,
N-(3-(5-((1-phenyl-1H-1,2,3-triazol-4-yl)methyl)hexahydropyrrolo[3,4-c]pyrrol-2(1H)-yl)phenyl)methanesulfonamide,
N-(3-(methyl(1-((1-phenyl-1H-1,2,3-triazol-4-yl)methyl)pyrrolidin-3-yl)amino)phenyl)methanesulfonamide,
N-(3-(methyl(1-((1-phenyl-1H-1,2,3-triazol-4-yl)methyl)azetidin-3-yl)amino)phenyl)methanesulfonamide,
N-(3-(4-((1-(pyridin-2-yl)-1H-1,2,3-triazol-4-yl)methyl)piperazin-1-yl)phenyl)propane-2-sulfonamide,
N-(3-(4-((1-phenyl-1H-1,2,3-triazol-4-yl)methyl)piperazin-1-yl)phenyl)cyclopropanesulfonamide,
N-(3-(4-((1-phenyl-1H-1,2,3-triazol-4-yl)methyl)-1,4-diazepan-1-yl)phenyl)methanesulfonamide,
N-(3-(methyl(1-((1-phenyl-1H-1,2,3-triazol-4-yl)methyl)pyrrolidin-3-yl)amino)phenyl)propane-2-sulfonamide,
N-(3-(4-((1-(3-fluorophenyl)-1H-1,2,3-triazol-4-yl)methyl)piperazin-1-yl)phenyl)propane-2-sulfonamide,
N-(3-(4-((1-(4-fluorophenyl)-1H-1,2,3-triazol-4-yl)methyl)piperazin-1-yl)phenyl)propane-2-sulfonamide,
N-(3-(4-((1-(6-fluoropyridin-2-yl)-1H-1,2,3-triazol-4-yl)methyl)piperazin-1-yl)phenyl)propane-2-sulfonamide,
N-(3-(5-((1-phenyl-1H-1,2,3-triazol-4-yl)methyl)hexahydropyrrolo[3,4-c]pyrrol-2(1H)-yl)phenyl)propane-2-sulfonamide,
N-(3-(4-((1-phenyl-1H-pyrazol-4-yl)methyl)piperazin-1-yl)phenyl)methanesulfonamide,
N-(3-(4-((1-benzyl-1H-pyrazol-4-yl)methyl)piperazin-1-yl)phenyl)methanesulfonamide,
N-(3-(4-((1-phenyl-1H-pyrazol-4-yl)methyl)piperazin-1-yl)phenyl)propane-2-sulfonamide,
3-(4-((1-phenyl-1H-pyrazol-4-yl)methyl)piperazin-1-yl)phenol,
N-(3-(4-((1-(pyridin-2-yl)-1H-pyrazol-4-yl)methyl)piperazin-1-yl)phenyl)methanesulfonamide,
N-(3-(4-((1-(pyridin-2-yl)-1H-pyrazol-4-yl)methyl)piperazin-1-yl)phenyl)propane-2-sulfonamide, N-(3-(4-((1-benzyl-1H-imidazol-4-yl)methyl)piperazin-1-yl)phenyl)propane-2-sulfonamide,
N-(6-(4-((1-phenyl-1H-1,2,3-triazol-4-yl)methyl)piperazin-1-yl)pyridin-2-yl)methanesulfonamide,
N-(6-(4-((1-phenyl-1H-1,2,3-triazol-4-yl)methyl)piperazin-1-yl)pyridin-2-yl)propane-2-sulfonamide,
N-(6-(4-((1-(2-fluorophenyl)-1H-1,2,3-triazol-4-yl)methyl)piperazin-1-yl)pyridin-2-yl)propane-2-sulfonamide,
N-(6-(4-((1-(2-fluorophenyl)-1H-1,2,3-triazol-4-yl)methyl)piperazin-1-yl)pyridin-2-yl)cyclopropanesulfonamide,
N-(6-(4-((1-(2-hydroxyphenyl)-1H-1,2,3-triazol-4-yl)methyl)piperazin-1-yl)pyridin-2-yl)propane-2-sulfonamide,
N-(6-(4-((1-(pyridin-2-yl)-1H-pyrazol-4-yl)methyl)piperazin-1-yl)pyridin-2-yl)propane-2-sulfonamide,
N-(6-(4-((1-(3,4-difluorophenyl)-1H-1,2,3-triazol-4-yl)methyl)piperazin-1-yl)pyridin-2-yl)propane-2-sulfonamide,
N-(6-(4-((1-(4-chloro-2-fluorophenyl)-1H-1,2,3-triazol-4-yl)methyl)piperazin-1-yl)pyridin-2-yl)propane-2-sulfonamide,
N-(6-(4-((1-phenyl-1H-1,2,3-triazol-4-yl)methyl)piperazin-1-yl)pyridin-2-yl)cyclopropanesulfonamide,
N-(5-chloro-6-(4-((1-phenyl-1H-1,2,3-triazol-4-yl)methyl)piperazin-1-yl)pyridin-2-yl)propane-2-sulfonamide,
N-(6-(5-((1-phenyl-1H-1,2,3-triazol-4-yl)methyl)hexahydropyrrolo[3,4-c]pyrrol-2(1H)-yl)pyridin-2-yl)propane-2-sulfonamide,
N-(6-(4-((1-phenyl-1H-1,2,3-triazol-4-yl)methyl)-1,4-diazepan-1-yl)pyridin-2-yl)propane-2-sulfonamide,
N-(6-(4-((1-(2-fluorophenyl)-1H-1,2,3-triazol-4-yl)methyl)-1-1,4-diazepan-1-yl)pyridin-2-yl)propane-2-sulfonamide,
N-(6-(5-((1-(2-fluorophenyl)-1H-1,2,3-triazol-4-yl)methyl)hexahydropyrrolo[3,4-c]pyrrol-2(1H)-yl)pyridin-2-yl)propane-2-sulfonamide, and
N-(6-(4-((1-(pyridin-2-yl)-1H-imidazol-4-yl)methyl)piperazin-1-yl)pyridin-2-yl)propane-2-sulfonamide, optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another highly preferred embodiment of the compound according to the invention according to general formulas I, II, III, or IV the compound is selected from
N-(3-(4-((1-phenyl-1H-1,2,3-triazol-4-yl)methyl)piperazin-1-yl)phenyl)propane-2-sulfonamide,
N-(3-(4-((1-(2-fluorophenyl)-1H-1,2,3-triazol-4-yl)methyl)piperazin-1-yl)phenyl)propane-2-sulfonamide,
N-(3-(methyl(1-((1-phenyl-1H-1,2,3-triazol-4-yl)methyl)pyrrolidin-3-yl)amino)phenyl)methanesulfonamide,
N-(3-(4-((1-phenyl-1H-1,2,3-triazol-4-yl)methyl)piperazin-1-yl)phenyl)cyclopropanesulfonamide,
N-(3-(methyl(1-((1-phenyl-1H-1,2,3-triazol-4-yl)methyl)pyrrolidin-3-yl)amino)phenyl)propane-2-sulfonamide,
N-(3-(4-((1-(3-fluorophenyl)-1H-1,2,3-triazol-4-yl)methyl)piperazin-1-yl)phenyl)propane-2-sulfonamide,
N-(3-(5-((1-phenyl-1H-1,2,3-triazol-4-yl)methyl)hexahydropyrrolo[3,4-c]pyrrol-2(1H)-yl)phenyl)propane-2-sulfonamide,
N-(3-(4-((1-phenyl-1H-pyrazol-4-yl)methyl)piperazin-1-yl)phenyl)methanesulfonamide,
N-(3-(4-((1-phenyl-1H-pyrazol-4-yl)methyl)piperazin-1-yl)phenyl)propane-2-sulfonamide,
3-(4-((1-phenyl-1H-pyrazol-4-yl)methyl)piperazin-1-yl)phenol,
N-(3-(4-((1-(pyridin-2-yl)-1H-pyrazol-4-yl)methyl)piperazin-1-yl)phenyl)propane-2-sulfonamide,
and
N-(6-(4-((1-phenyl-1H-1,2,3-triazol-4-yl)methyl)-1,4-diazepan-1-yl)pyridin-2-yl)propane-2-sulfonamide;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

As this invention is aimed at providing a compound or a chemically related series of compounds which act as dual ligands of the σ₁ receptor and the μ-opiod receptor it is a very preferred embodiment in which the compounds are selected which act as dual ligands of the σ₁ receptor and the μ-opiod receptor and especially compounds which have a binding expressed as K, which is <100 nm for both receptors.

In the following the phrase "compound of the invention" is used. This is to be understood as any compound according to the invention as described above according to general formulas I, II, III, IV, or V.

The compounds of the invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

In general the processes are described below in the experimental part. The starting materials are commercially available or can be prepared by conventional methods.

A preferred aspect of the invention is also a process for the production of a compound according to formula I,

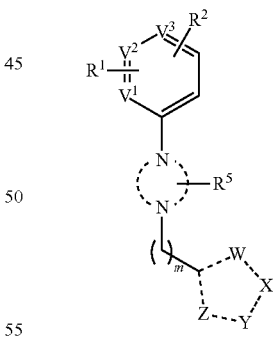

wherein $R^1$, $R^2$, $R^5$, $V^1$, $V^2$, $V^3$, W, X, Y, Z and m as well as

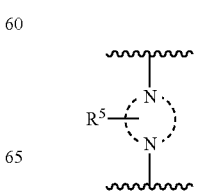

are as defined in claim 1 or according to formula Ia

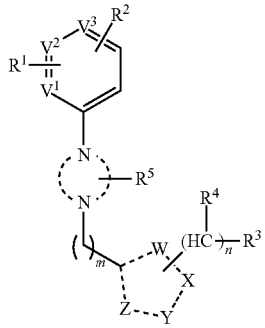

wherein $R^1$, $R^2$, $R^3$, $R^4$, $R^5$, $V^1$, $V^2$, $V^3$, W, X, Y, Z, n and m are as defined in claim 1
wherein a compound of formula VI or its suitable salt like the hydrochloride

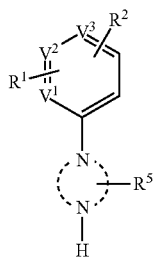

wherein $R^1$, $R^2$, $R^5$, $V^1$, $V^2$, and $V^3$ are as defined for Formula I, is reacted with a compound according to formula VII (for a compound according to formula I) or according to formula VIIa (for a compound according to formula Ia) under the conditions of Step 1

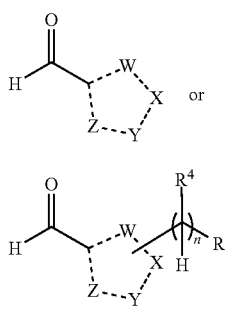

wherein $R^3$, $R^4$, W, X, Y, Z and n are as defined in Formula I, leading to a compound according to formula (I) or formula (Ia) respectively,
wherein the reductive amination reaction of the compounds of formula (VI) and (VII or VIIa) of Step 1 is carried out with a reductive reagent in an aprotic solvent in the presence of an organic base,
Preferably in the reaction of Step 1 above the reductive reagent is sodium triacetoxyborohydride, the aprotic solvent is dichloroethane and/or the organic base is diisopropylethylamine.
Another preferred aspect of the invention is a process for the production of a compound according to the invention, wherein a compound of formula V

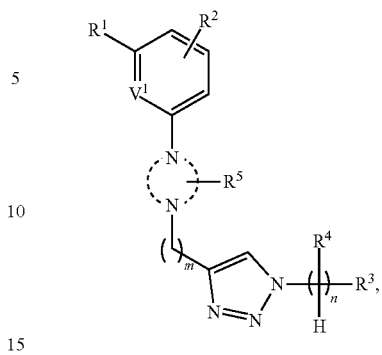

wherein $R^1$, $R^2$, $R^3$, $R^4$, $R^5$, n and m as well as

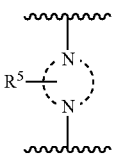

are as defined in claim 7,
wherein a compound of formula VIII or its suitable salt like the hydrochloride

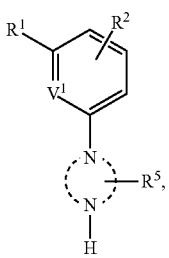

wherein $R^1$, $R^2$, and $R^5$ are as defined in claim 7, is reacted with a compound according to formula X under the conditions of Step 2

wherein m is as defined in claim 7, leading to a compound according to formula IX,

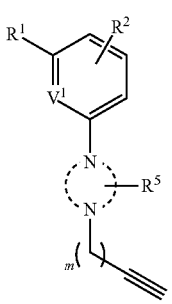

wherein $R^1$, $R^2$, $R^5$ and m are as defined in claim 7, followed by reacting said compound according to formula IX with a compound according to formula XI under the conditions of Step 3

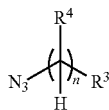
(XI)

wherein R$^3$, R$^4$ and n are as defined in claim 7, under the conditions of Step 3, leading to a compound according to formula (V), wherein X is a leaving group like a halogen (F, Cl, I, Br) or sulphate like chlorine, wherein the reaction of Step 2 of said compounds of general formula (VIII) with said compounds of formula (X) is carried out in the presence of a base in an aprotic solvent.

wherein the reaction of Step 3 of said compounds of general formula (IX) with said compounds of formula (XI) is carried out in the presence of a copper salt and sodium ascorbate in a mixture of protic organic solvent and water.

Preferably in the reaction of Step 2 above the base is Et$_3$N, the aprotic solvent is tetrahydrofurane (THF) and/or the reaction is preferably carried out at a temperature range of 25-75° C. The temperature may be raised by conventional methods or by use of microwave.

Preferably in the reaction of Step 3 above the copper salt is CuSO$_4$.5H$_2$O and the mixture of protic organic solvent and water is a mixture of t-BuOH:H$_2$O 1:1 and/or the reaction is preferably carried out at room temperature.

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formulas I, II, III, IV, or V or a pharmaceutically acceptable salt or steroisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to a compound of the invention according as described above according to general formulas I, II, III, IV, or V or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general spirit of the present invention.

EXAMPLES

General Experimental Part (Methods and Equipment of the Synthesis and Analysis

All solvents used for synthesis were p. a. quality.
Method I
A process is described for the preparation of compounds of general formula ($I_{ex}$) where $R_1$, $R_2$, $R_3$, $R_4$, A, B, Y, Z, W, n and m have the meanings as defined above (with "A", "B", "Y", and "Z" being "X", "Y", "W", "Z" in the above description, respectively, and "W" being "$V^1$" in the above description), comprising the reaction of compound of formula ($II_{ex}$), or its suitable salt such as hydrochloride, with a compound of general formula ($III_{ex}$) as described in Scheme 1. The reductive amination reaction of compounds of formula ($II_{ex}$) and ($III_{ex}$) is preferably carried out with a reductive reagent, preferably sodium triacetoxyborohydride, in an aprotic solvent, preferably dichloroethane, in the presence of an organic base preferably diisopropylethylamine.

Scheme 1:

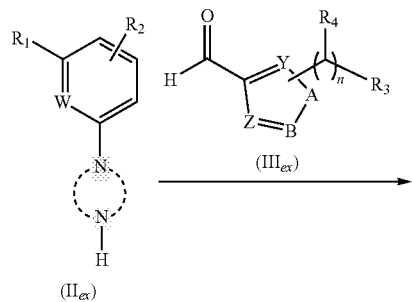

Method II

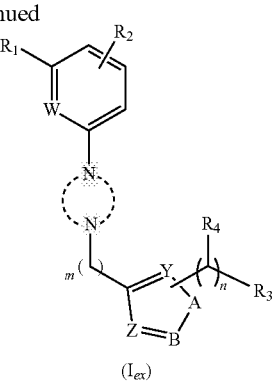

A process is described for the preparation of compounds of general formula ($Ia_{ex}$ and $Ib_{ex}$) where $R_1$, $R_2$, $R_3$, $R_4$, $R_5$, W, n and m have the meanings as defined above (with "W" being "$V^1$" in the above description), comprising the reaction of compound of formula ($II_{ex}$) with a compound of formula ($IV_{ex}$), where X is a suitable leaving group such as an halogen or sulfonate, and the reaction of the resulting intermediate ($V_{ex}$) with convenient reagents such as ($VI_{ex}$), ($VII_{ex}$) or ($VIII_{ex}$) to give the triazoles ($Ia_{ex}$) and ($Ib_{ex}$). As indicated in Scheme 2, different methods can be used in the practical realization of these two reactions. In some cases, the intermediate ($V_{ex}$) can be isolated but in other cases the two steps may be carried out one-pot. The compounds of formula ($IV_{ex}$) and the reagents of formula ($VI_{ex}$), ($VII_{ex}$) or ($VIII_{ex}$) are either commercially available or can be prepared following conventional methods reported in the literature. Alternately, some of the azides can be prepared in situ.

Scheme 2:

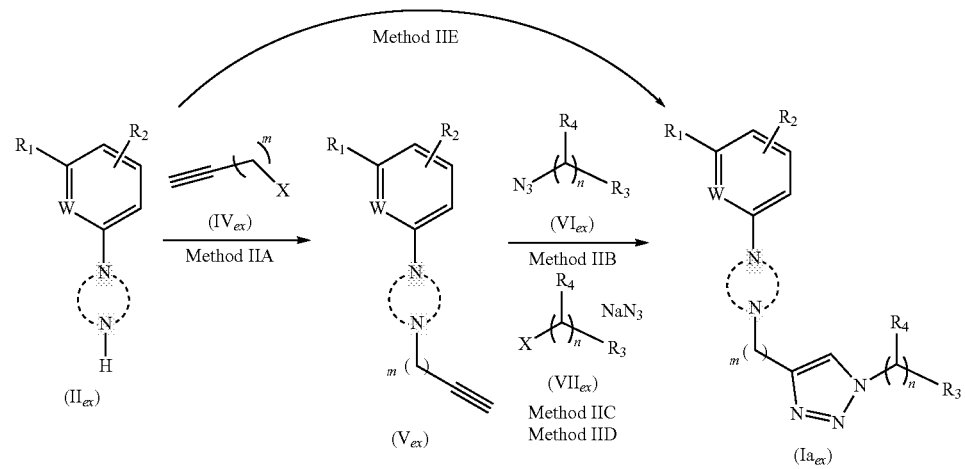

In Method IIA the reaction of compounds of general formula ($II_{ex}$) with compounds of formula ($IV_{ex}$) where X is a suitable leaving group, such as a halogen or sulfonate, is carried out in the presence of a base, preferably $Et_3N$, in an aprotic solvent such as tetrahydrofurane (THF) at a temperature range of 25-75° C., using conventional heating or a microwave reactor.

In Method IIB the reaction of compounds of formula ($V_{ex}$) with azides of general formula ($VI_{ex}$) is carried out in the presence of a copper salt, preferably $CuSO_4.5H_2O$ and sodium ascorbate, in a mixture of protic organic solvent and water, preferably a mixture of t-BuOH:$H_2O$ 1:1 at room temperature.

In Method IIC the azide is generated in situ. The precursor of the azide ($VII_{ex}$), where X is a suitable leaving group such as an halogen or sulfonate, is treated with sodium azide and a copper salt, preferably CuI, in an organic solvent, preferably dimethylformamide, at 100° C. using microwave irradiation. Alternatively, some additives such as $N_1,N_2$-dimethylethane-1,2-diamine (DMEDA) and sodium ascorbate can be added to the reaction mixture.

In Method IIID the precursor of the azide of general formula ($VII_{ex}$) is treated with sodium azide in a mixture of a protic organic solvent and water, preferably a mixture of t-BuOH:$H_2O$ 1:1, at 100° C. using microwave irradiation for a suitable time, such as 1 h or until completed reaction. The in situ formed azide is then treated with compounds of general formula ($V_{ex}$) in the presence of a copper salt, preferably $CuSO_4.5H_2O$ and sodium ascorbate at room temperature.

In Method IIIE the intermediates of general formula ($Ia_{ex}$) are prepared in a one-pot procedure comprising the reaction of compounds of general formula ($II_{ex}$) and propargyl bromide in the presence of a base, preferably $Et_3N$, in water at room temperature for 1 h or until completed reaction, after which compounds of general formula ($VI_{ex}$) are added in the presence of a copper salt, preferably CuI, at room temperature (Tetrahedron 2005, 61, 9331-9337).

Additionally the compounds of formula $I_{ex}$ can be prepared by interconversion of functional groups present in the final molecules. In this, functional groups that are present on some part of the final molecule could be converted into other related functional groups either with or without an intermediate product by inducing a chemical reaction.

Synthesis of Intermediates of General Formula (II)

In some cases, compounds of formula ($II_{ex}$) are commercially available or they can be obtained by conventional methods. Alternatively, a compound of formula ($II_{ex}$) can be obtained following different methods:
Method III

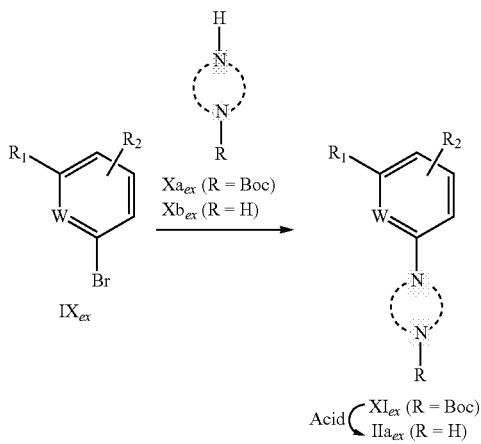

Scheme 3

Method IIIA comprises:
a) The reaction of compounds of formula ($IX_{ex}$) with a compound of formula ($Xa_{ex}$) in the presence of a palladium catalyst, preferably Pd(OAc), a phosphine ligand, preferably di-tert-butyl(2'-methyl-[1,1'-biphenyl]-2-yl)phosphine, [1,1'-biphenyl]-2-yldi-tert-butylphosphine or ((2,2'-bis(diphenylphosphino)-1,1'-binaphthyl)), in the presence of a base, preferably sodium tert-butoxide, in an organic solvent, preferably toluene, at a range of temperature of 80° to 120° C.
b) The hydrolysis of the resulting compound ($XI_{ex}$) in an acidic medium, preferably HCl in an organic solvent, preferably 1,4-dioxane.

Method IIIB comprises the reaction of compounds of formula ($IX_{ex}$) with a compound of formula ($Xb_{ex}$) at a range of temperature of 80 to 220° C. in a polar solvent, preferably n-buthanol. Alternatively, the reaction can be carried out with microwave irradiation.

Method IV

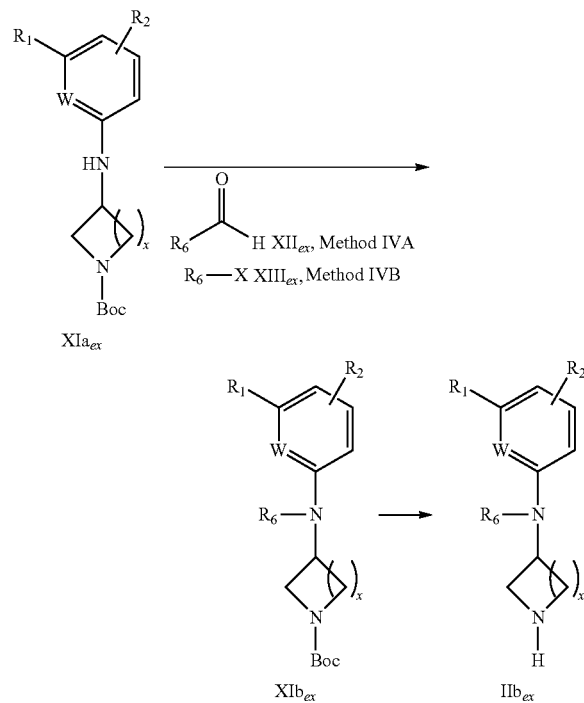

Scheme 4

Intermediates of general formula ($IIb_{ex}$) may be prepared according to the reaction sequence shown in scheme 4 (Method IV).
a) Method IVA comprises the reductive amination reaction of the intermediate ($XIa_{ex}$) with an aldehyde of general formula ($XII_{ex}$) in the presence of a reductive reagent, preferably sodium triacetoxyborohydride, in an aprotic solvent, preferably dichloroethane; in some cases, in the presence of an acid as additive, preferably acetic acid.
Method IVB comprises the reaction of the intermediate ($XIa_{ex}$) with a compound of general formula ($XIII_{ex}$) where X is a suitable leaving group such as an halogen or sulfonate, in the presence of a base, in an organic solvent.
b) The hydrolysis of the resulting compound ($XIb_{ex}$) in an acidic medium, preferably HCl in an organic solvent, preferably 1,4-dioxane.

Method V

Scheme 5

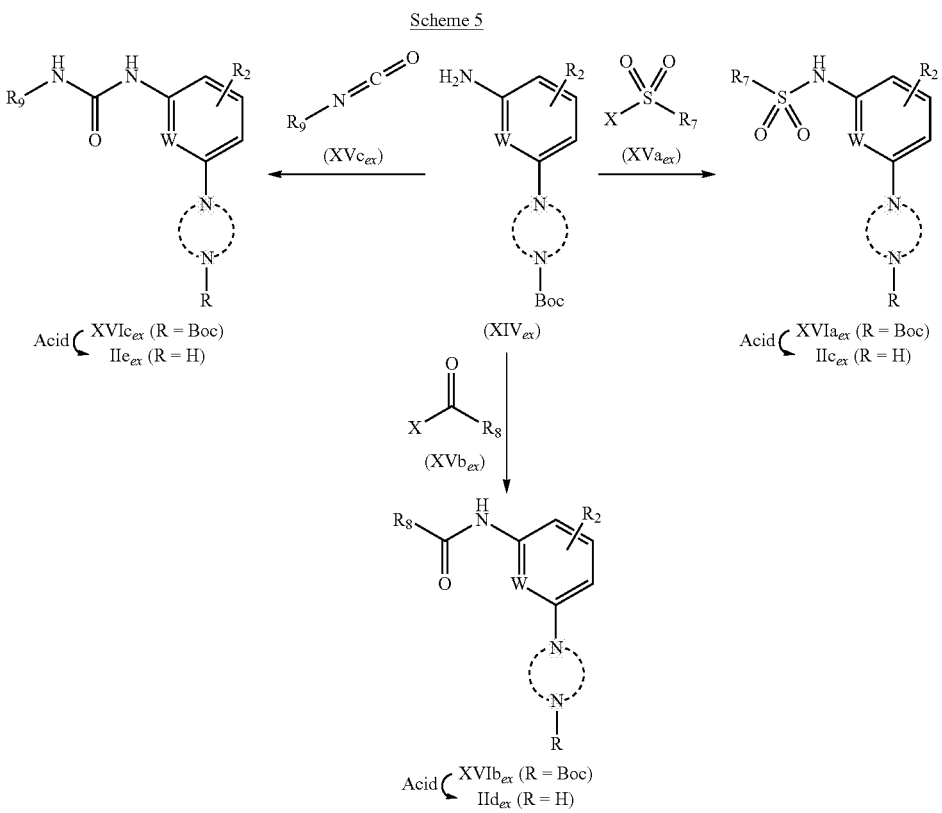

The process for the preparation of intermediates of general formula ($IIc_{ex}$-$e_{ex}$) where W, $R_2$ $R_7$, $R_8$, and $R_9$ have the meanings as defined above (with "W" being "$V^1$" in the above description), according to the reaction sequence shown in scheme 5, which comprises:

a) The reaction of intermediate ($XIV_{ex}$) with a compound of formula ($XVa_{ex}$-$c_{ex}$, where X is a suitable leaving group, such as halogen, in the presence of a base, preferably pyridine, $Et_3N$, NaH, $K_2CO_3$ or $Cs_2CO_3$ at a range of temperature of 0° C. to 120° C., in the presence of a suitable solvent, such as dichloromethane or alternatively, the reactions can be carried out in a microwave reactor.

b) The deprotection of the resulting compounds ($XVIa_{ex}$-$c_{ex}$) in an acidic medium, preferably HCl in an organic solvent, preferably 1,4-dioxane.

Synthesis of Intermediates of General Formula III

The aldehydes of general formula ($III_{ex}$) where $R_3$, $R_4$, A, B, Y, Z and n have the meanings as defined above (with "A", "B", "Y", and "Z" being "X", "Y", "W", "Z" in the above description, respectively), are commercially available or can be prepared by methods described in the bibliography (for example, WO2010046780 A2, WO2008157844 A1) or by the methods described below and summarized in Scheme 6.

Scheme 6

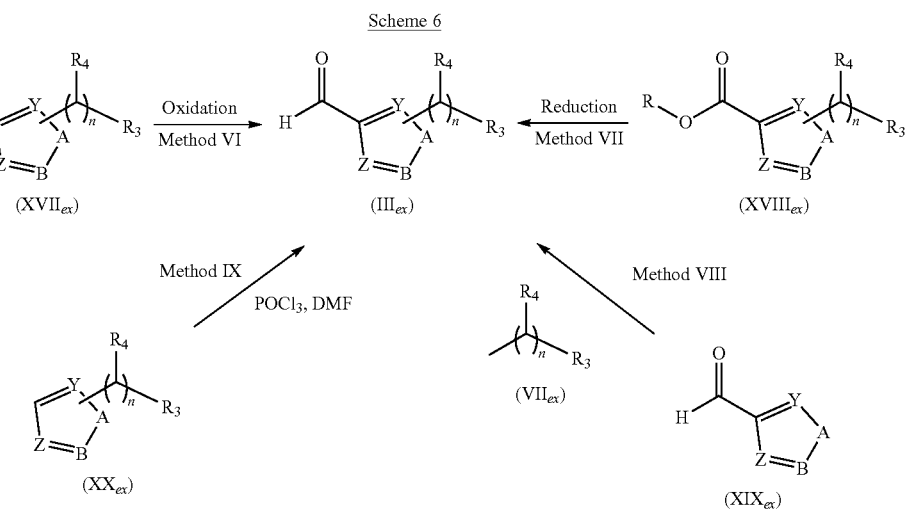

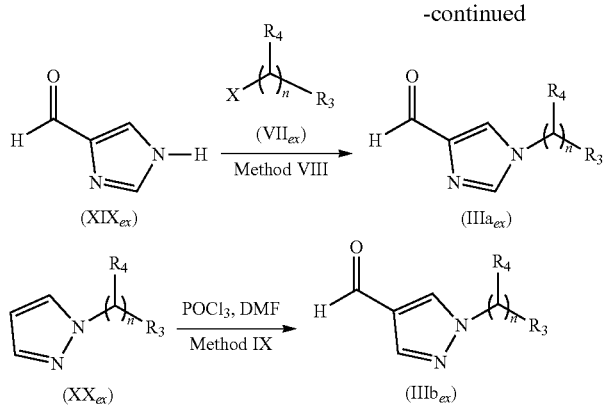

Method VI involves the oxidation of compounds of general formula (XVII$_{ex}$), using a suitable oxidizing reagent, such as MnO$_2$, in an aprotic solvent such as dichloromethane.

Method VII involves the reduction of compounds of general formula (XVIII$_{ex}$) with a suitable reducing agent such as DIBAL-H at −78° C. in an aprotic solvent, preferably dichloromethane.

Method VIII, which is exemplified for the preparation of compounds of formula IIIa, comprises the reaction between compounds of formula (XIX$_{ex}$) with compounds of general formula (VII$_{ex}$) where X is a suitable leaving group as an halogen or sulfonate, in the presence of an inorganic base, preferably K$_2$CO$_3$, in a polar solvent preferably DMF at 140° C. using microwaves irradiation. Alternatively, using an aqueous solution of NaOH as base and a phase transfer catalyst, preferably tetra-n-butylammonium bromide, in an aprotic solvent, preferably toluene at room temperature. Alternatively, using proline and CuI as catalysts, in the presence of a base, preferably K$_2$CO$_3$, in a polar solvent, preferably DMSO at a temperature range of 90-110° C.

Method IX, which is exemplified for the preparation of compounds of formula IIIb, comprises the reaction between the compounds of general formula (XX$_{ex}$) with POCl$_3$ in DMF as solvent at 90-110° C.

Synthesis of Intermediates of General Formula XVII

The alcohols of general formula (XVII$_{ex}$) where R$_3$, R$_4$, A, B, Y, Z and n have the meanings as defined above (with "A", "B", "Y", and "Z" being "X", "Y", "W", "Z" in the above description, respectively), are commercially available or can be prepared by methods described in the bibliography (for example J. Org. Chem. 2010, 75, 6540-6548, WO2010080864, Org. Lett. 2009, 21, 4954-4957, J. Med. Chem. 2011, 54, 5988-5999). In particular, alcohols of formula XVIIa$_{ex}$ and XVIIb$_{ex}$ can be prepared by the methods outlined in Scheme 7.

Scheme 7

Method X

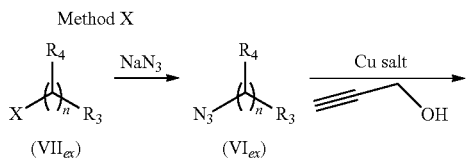

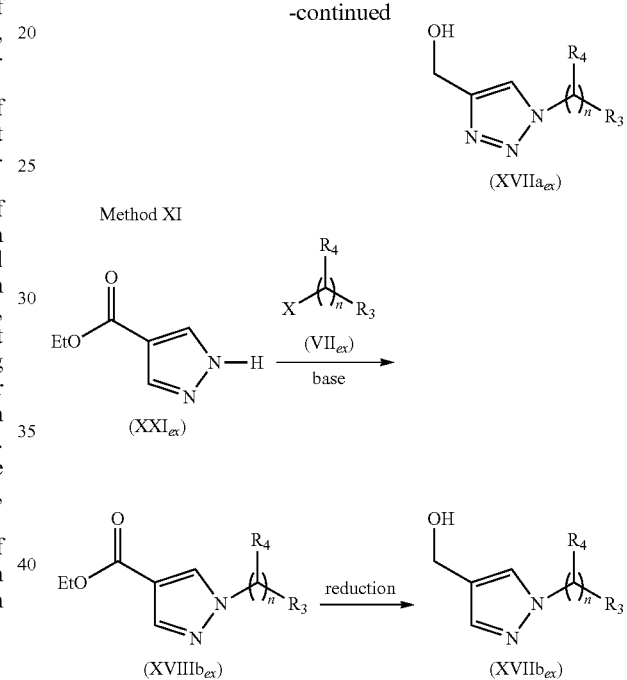

Method X comprises the cycloaddition reaction of an azide of general formula (VI$_{ex}$) with propargyl alcohol in the presence of a copper salt as catalyst. The azides of general formula (VI$_{ex}$) are commercially available or may be prepared following conventional methods reported in the literature; alternately, some of the azides can be prepared in situ. The reaction is performed in the presence of a copper salt, preferably CuSO$_4$.5H$_2$O and sodium ascorbate in a mixture of protic organic solvent and water, preferably a mixture of t-BuOH:H$_2$O 1:1 at room temperature Alternatively, CuI can be used as copper salt in a polar solvent as dimethylformamide at 100° C. using microwave irradiation or Cu(OAc)$_2$ can be used as copper salt in a polar solvent, such as tert-butanol at room temperature. The reaction can also be effected using a one-pot procedure, in which case it is performed late with sodium azide in a mixture of protic organic solvent and water, preferably a mixture of t-BuOH:H$_2$O 1:1, heating at 100° C. using microwave irradiation for 1 h or until completed reaction, followed by the reaction with propargyl alcohol in the presence of a copper salt, preferably CuSO$_4$.5H$_2$O and sodium ascorbate at room temperature.

Compounds of general formula (XVIIb$_{ex}$), where R$_3$, R$_4$, and n have the meanings as defined above can be prepared using Method XI. This process comprises:

a) The reaction between compound of formula (XXI$_{ex}$) with a compound of general formula (VII$_{ex}$) where X is a suitable leaving group such as an halogen or sulfonate, in the presence of a base, preferably K$_2$CO$_3$, in a polar solvent, preferably acetone at 60° C.

b) The reduction of the resulting compound (XVIIIb$_{ex}$) with a suitable hydride reagent, preferably LiAlH$_4$ at 0° C., in an aprotic solvent, preferably THF.

Synthesis of Intermediates of General Formula XVIII

The esters of general formula (XVIII$_{ex}$), where R$_3$, R$_4$, A, B, Y, Z and n have the meanings as defined above (with "A", "B", "Y", and "Z" being "X", "Y", "W", "Z" in the above description, respectively), are commercially available or can be prepared by methods described in the bibliography (*Synthesis*, 1975, 9, 609-610; WO2011098904; *Org. Lett.* 2010, 12, 9, 2166-2169, Org. Lett. 2008, 10, 5389-5392). In particular, esters of general formula XVIIIa$_{ex}$ and XVIIIb$_{ex}$ can be prepared by the methods outlined in Scheme 8.

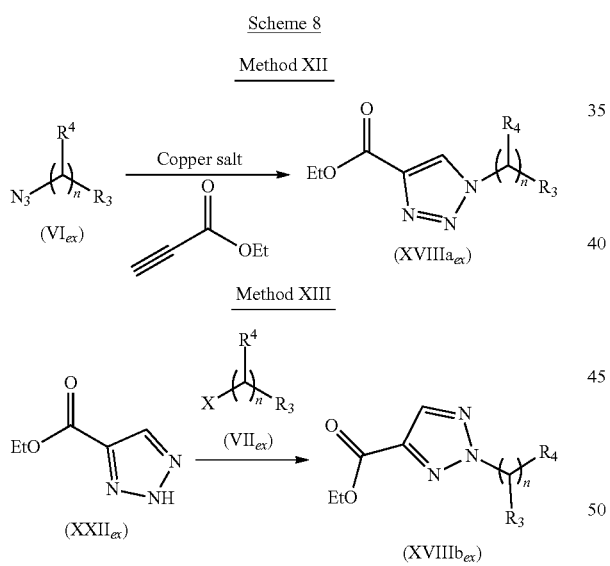

Scheme 8
Method XII

Method XIII

Method XII comprises the cycloaddition reaction of an azide of general formula (VI$_{ex}$) with ethyl propiolate in the presence of a copper salt as catalyst, preferably Cu(OTf)$_2$*C$_6$H$_6$ in an aprotic solvent, preferably toluene, at 70-100° C.

Method XIII comprises the reaction between compound of formula (XXII$_{ex}$) with a compound of general formula (VII$_{ex}$) where X is a suitable leaving group such as an halogen or sulfonate, in the presence of a base, preferably K$_2$CO$_3$, a copper salt, preferably CuCl, and a ligand, preferably proline, in a polar solvent, preferably DMSO at 85-170° C. under microwaves irradiation.

Synthesis of Intermediates

Examples of Preparation of an Intermediate of Formula (V$_{ex}$), Method IIA

Synthesis of N-(6-(4-(prop-2-yn-1-yl)piperazin-1-yl)pyridin-2-yl)propane-2-sulfonamide

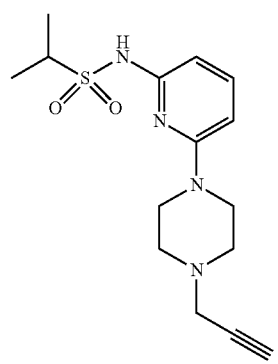 [SMILES: C#CCN1CCN(c2cccc(NS(=O)(=O)C(C)C)n2)CC1]

A suspension of N-(6-piperazin-1-yl)pyridin-2-yl)propane-2-sulfonamide (85 mg, 0.30 mmol), Et$_3$N (54 µl, 0.39 mmol) and propargyl bromide (37 µL, 80% wt in toluene, 0.33 mmol) in THF (4.5 ml) was irradiated with microwaves at 75° C. for 1 h. The reaction mixture was cooled and the solvent evaporated. Purification by flash chromatography, silica gel, gradient hexane to ethyl acetate afforded the title product (54 mg, 56% yield). $^1$H-NMR (300 MHz, CDCl$_3$), δ ppm: 7.41 (t, J=8 Hz, 1H), 7.14 (bs, 1H), 6.49 (d, J=8 Hz, 1H), 6.32 (d, J=8 Hz, 1H), 3.57 (septet, J=7 Hz, 1H), 3.54 (m, 4H), 3.35 (d, J=2.4 Hz, 2H), 2.64 (m, 4H), 2.27 (t, J=2.4 Hz, 1H), 1.41 (d, J=7 Hz, 6H).

Example of Preparation of an Intermediate of Formula (IIa$_{ex}$), Method IIIa

Synthesis of N-(3-(pyrrolidin-3-ylamino)phenyl)methanesulfonamide

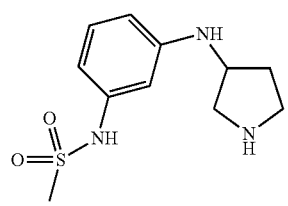 [SMILES: CS(=O)(=O)Nc1cccc(NC2CCNC2)c1]

tert-Butyl 3-((3-methylsulfonamido)phenyl)amino)pyrrolidine-1-carboxylate

An oven-dried schlenk was evacuated and backfilled with argon. The flask was charged with Pd(OAc)$_2$ (5 mg, 0.022 mmol), [1,1'-biphenyl]-2-yldi-tert-butylphosphine (13 mg, 0.045 mmol), NaOtBu (38 mg, 0.392 mmol), and N-(3-bromophenyl) methanesulfonamide (70 mg, 0.280 mmol)

and evacuated and backfilled with argon. Toluene (0.6 mL) and tert-butyl 3-aminopyrrolidine-1-carboxylate (61 µl; 0.336 mmol) were added and heated at 100° C. for 2 h. The reaction mixture was cooled and filtered through a pad of celite and the solvent was removed. The crude was purified by flash chromatography, silica gel, gradient from hexane to hexane:ethyl acetate (1:1) to afford the desired product (55 mg, 55% yield). $^1$H-NMR (500 MHz, CDCl$_3$), δ ppm: 7.15 (m, 1H), 6.94 (bs, 1H), 6.56 (m, 2H), 6.42 (d, J=7.3 Hz, 1H), 4.03 (m, 2H), 3.74 (m, 1H), 3.51 (m, 2H), 3.28 (m, 1H), 3.02 (s, 3H), 2.20 (m, 1H), 1.90 (m, 1H), 1.49 (s, 9H).

N-(3-(Pyrrolidin-3-ylamino)phenyl)methanesulfonamide

To a solution of tert-butyl 3-((3-(methylsulfonamido) phenyl)amino)pyrrolidine-1-carboxylate (80 mg, 0.225 mmol) in dioxane (0.40 ml) was added a solution of 4M HCl in dioxane (0.78 ml, 3.15 mmol) and stirred at rt overnight. The reaction mixture was concentrated to afford the desired product as a hydrochloride (74 mg, 100%). $^1$H-NMR (400 MHz, CD$_3$OD), δ ppm: 7.35 (m, 1H), 7.00 (m, 1H), 6.87 (m, 1H), 6.73 (m, 1H), 4.40 (m, 1H), 3.70 (m, 2H), 3.56 (m, 2H), 3.11 (s, 3H), 2.50 (m, 1H), 2.30 (m, 1H).

Example of Preparation of an Intermediate of Formula (IIa$_{ex}$), Method IIIb

Synthesis of N-(6-(piperazin-1-yl)pyridin-2-yl)cyclopropanesulfonamide

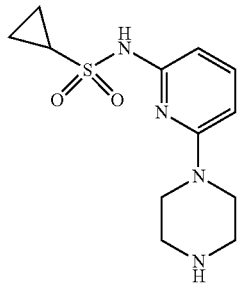 [SMILES: O=S(=O)(Nc1cccc(N2CCNCC2)n1)C1CC1]

N-(6-Bromopyridin-2-yl)cyclopropanesulfonamide

To a solution of 6-bromopyridin-2-amine (300 mg, 1.73 mmol) in pyridine (2 ml), cyclopropanesulfonyl chloride (317 mg, 2.25 mmol) was added and the mixture was heated at 50° C. in a sealed tube for 16 h. The reaction mixture was concentrated and purified by flash chromatography, silica gel, gradient from hexane to hexane:ethyl acetate (1:1) to afford the desired product (400 mg, 83% yield). $^1$H-NMR (400 MHz, CDCl$_3$), δ ppm: 7.55 (t, J=8 Hz, 1H), 7.40 (bs, 1H), 7.34 (dd, J=8, 1 Hz, 1H), 7.25 (dd, J=8, 1 Hz, 1H), 2.72 (m, 1H), 1.31 (m, 1H), 1.07 (m, 1H).

N-(6-(Piperazin-1-yl)pyridin-2-yl)cyclopropanesulfonamide

In a sealed tube, a mixture of N-(6-bromopyridin-2-yl) cyclopropanesulfonamide (100 mg, 0.36 mmol) and piperazine (311 mg, 3.61 mmol) in n-BuOH (4.5 ml) was irradiated with MW at 200° C. for 1 h. The reaction mixture was concentrated and purified by flash chromatography, silica gel, gradient from dichloromethane to 35% MeOH to afford the desired product (96 mg, 94% yield) as white solid. $^1$H-NMR (300 MHz, CD$_3$OD), δ ppm: 7.52 (t, J=8 Hz, 1H), 6.51 (d, J=8 Hz, 1H), 6.41 (d, J=8 Hz, 1H), 3.74 (m, 4H), 3.19 (m, 4H), 3.01 (m, 1H), 1.18 (m, 2H), 1.03 (m, 1H).

Example of Preparation of an Intermediate of Formula (IIb$_{ex}$), Method IVA

Synthesis of N-(3-(methyl(pyrrolidin-3-yl)amino) phenyl)methanesulfonamide

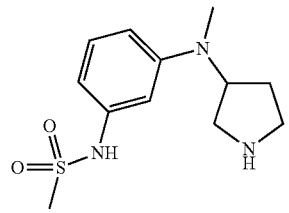 [SMILES: CN(c1cccc(NS(C)(=O)=O)c1)C1CCNC1]

tert-Butyl 3-(methyl(3-(methylsulfonamido)phenyl) amino)pyrrolidine-1-carboxylate To a solution of tert-butyl 3-((3-(methylsulfonamido) phenyl)-amino)pyrrolidine-1-carboxylate (55 mg, 0.15 mmol) in dichloroethane (3 mL), paraformaldehyde (20 mg, 0.61 mmol), NaBH(OAc)$_3$ (131 mg, 0.61 mmol) and acetic acid (8.9 µL, 0.15 mmol) were added. The reaction mixture was stirred at r.t. overnight in a sealed tube. An aqueous NaHCO$_3$ saturated solution was added and extracted with dichloromethane. The organic phases were dried over Na$_2$SO$_4$ and the solvent was removed to afford the title product (54 mg, 94%). $^1$H-NMR (400 MHz, CDCl$_3$), δ ppm: 7.20 (dd, J=7.8, 8.4 Hz, 1H), 6.79 (bs, 1H), 6.71 (t, J=2.2 Hz, 1H), 6.65 (dd, J=2.2, 8.4 Hz, 1H), 6.61 (d, J=7.8 Hz, 1H), 4.40 (m, 1H), 3.56 (m, 2H), 3.36 (m, 2H), 3.02 (s, 3H), 2.85 (s, 3H), 2.10 (m, 2H), 1.49 (s, 9H).

N-(3-(Methyl(pyrrolidin-3-yl)amino)phenyl)methanesulfonamide

To a solution of tert-butyl 3-(methyl(3-(methylsulfonamido)phenyl)amino)pyrrolidine-1-carboxylate (54 mg, 0.14 mmol) in dioxane (0.27 ml), a solution of 4M HCl in dioxane (0.51 ml; 2.04 mmol) was added. The reaction mixture was stirred at rt overnight. The mixture was concentrated to afford the title product as a hydrochloride (50 mg, 100%). $^1$H-NMR (500 MHz, CD$_3$OD), δ ppm: 7.68 (bs, 1H), 7.55 (m, 2H), 7.36 (d, J=7.5 Hz, 1H), 4.80 (m, 1H), 3.70 (m, 3H), 3.45 (m, 1H), 3.34 (s, 3H), 3.10 (s, 3H), 2.43 (m, 2H).

Example of Preparation of an Intermediate of Formula (IIc$_{ex}$), Method V

Synthesis of N-(3-(piperazin-1-yl)phenyl)propane-2-sulfonamide

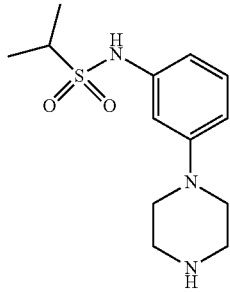 [SMILES: CC(C)S(=O)(=O)Nc1cccc(N2CCNCC2)c1]

tert-Butyl 4-(3-(1-methylethylsulfonamido)phenyl)piperazine-1-carboxylate

To a solution of tert-butyl 4-(3-aminophenyl)piperazine-1-carboxylate (100 mg, 0.36 mmol) in pyridine (0.44 ml, 5.41 mmol), isopropylsulfonyl chloride (48 μl, 0.43 mmol) was added and the reaction mixture was stirred at 50° C. overnight. Solvent was removed under vacuum and the residue was purified by flash chromatography, silica gel, gradient from hexane to ethyl acetate to afford the desired product (87 mg, 63% yield). $^1$H-NMR (400 MHz, CDCl$_3$), δ ppm: 7.20 (t, J=8 Hz, 1H), 6.87 (s, 1H), 6.71 (m, 2H), 6.56 (s, 1H), 3.59 (m, 4H), 3.33 (septet, J=7 Hz, 1H), 3.16 (m, 4H), 1.50 (s, 9H), 1.40 (d, J=7 Hz, 6H).

N-(3-(Piperazin-1-yl)phenyl)propane-2-sulfonamide

To a solution of tert-butyl 4-(3-(1-methylethylsulfonamido)phenyl)piperazine-1-carboxylate (64 mg, 0.17 mmol) in dioxane (0.3 ml), a solution of 4M HCl in dioxane (0.6 ml, 2.34 mmol) was added and stirred at rt overnight. The mixture was concentrated to dryness to afford the title compound (57 mg, 96% yield) as hydrochloride. $^1$H-NMR (300 MHz, MeOD) δ ppm: 7.27 (t, J=8 Hz, 1H), 7.00 (s, 1H), 6.84 (m, 2H), 3.44 (m, 8H), 3.32 (septet, J=7 Hz, 1H), 1.36 (d, J=7 Hz, 6H).

Examples of Preparation of an Intermediate of Formula (III$_{ex}$), Method VI

Synthesis of 1-(2-fluorophenyl)-1H-1,2,3-triazole-4-carbaldehyde

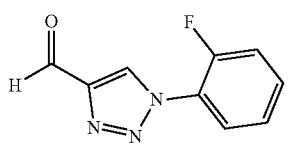 [SMILES: O=Cc1cn(-c2ccccc2F)nn1]

To a solution of (1-(2-fluorophenyl)-1H-1,2,3-triazol-4-yl)methanol (100 mg, 0.52 mmol) in dry dichloromethane (5 ml), MnO$_2$ (465 mg, 4.70 mmol) was added and the resulting dark solution was stirred during 4 h at rt. Then, the reaction mixture was filtered on Celite and the solvent was removed under vacuum to afford the desired product (84 mg, 74% yield). $^1$H-NMR (400 MHz, CDCl$_3$), δ ppm: 10.24 (s, 1H), 8.64 (d, J=2 Hz, 1H), 8.00 (td, J=8, 1 Hz, 1H), 7.52 (m, 1H), 7.32-7.41 (m, 2H).

Examples of Preparation of an Intermediate of Formula (III$_{ex}$), Method VII

Synthesis of 1-(5-fluoropyridin-2-yl)-1H-1,2,3-triazole-4-carbaldehyde

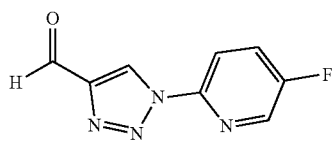 [SMILES: O=Cc1cn(-c2ccc(F)cn2)nn1]

DIBAL-H (0.95 ml, 1 M in DCM, 0.95 mmol) was added dropwise to a solution of ethyl 1-(5-fluoropyridin-2-yl)-1H-1,2,3-triazole-4-carboxylate (204 mg, 0.86 mmol) in dichloromethane (9 mL) at −78° C. under argon atmosphere. The resulting mixture was stirred for 1 h at this temperature and then an additional amount of DIBAL-H (0.95 ml, 1 M in DCM, 0.95 mmol) was added. After stirring for 1 h at −78° C., the mixture was quenched with methanol and water at −78° C. Then, the reaction mixture was filtered on celite and the filtrate was washed with dichloromethane. The solvent was removed under vacuum and the residue was purified by flash chromatography, silica gel, gradient hexane to ethyl acetate to provide the desired product (146 mg, 88% yield) as a white solid. $^1$H-NMR (500 MHz, CDCl$_3$), δ ppm: 10.24 (s, 1H), 9.04 (s, 1H), 8.40 (d, J=3 Hz, 1H), 8.28 (dd, J=9, 4 Hz, 1H), 7.71 (ddd, J=9, 7, 3 Hz, 1H) Examples of preparation of an intermediate of formula (IIIa$_{ex}$), Method VIII Synthesis of 1-(pyridin-2-yl)-1H-imidazole-4-carbaldehyde

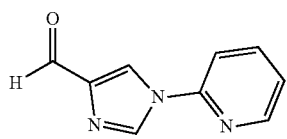 [SMILES: O=Cc1cn(-c2ccccn2)cn1]

A mixture of K$_2$CO$_3$ (283 mg, 2.05 mmol), 2-bromopyridine (162 mg, 1.02 mmol) and 1H-imidazole-4-carbaldehyde (108 mg, 1.128 mmol) in DMF (5 ml) was irradiated with microwaves at 140° C. for 1.5 h. Water was added and the aqueous phase was extracted with dichloromethane. The combined organic phases were washed with brine and water, dried over Na$_2$SO$_4$, filtered and concentrated. Purification by flash chromatography, silica gel, gradient from dichloromethane to 30% methanol afforded the title product (12 mg, 6% yield). $^1$H-NMR (500 MHz, CDCl$_3$), δ ppm: 9.99 (s, 1H), 8.56 (m, 1H), 8.46 (d, J=1.3 Hz, 1H), 8.35 (d, J=1.3 Hz, 1H), 7.92 (m, 1H), 7.46 (m, 1H), 7.37 (m, 1H).

Synthesis of
1-(2-fluorophenyl)-1H-imidazole-4-carbaldehyde

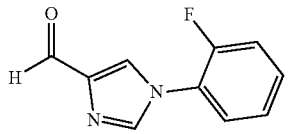 [SMILES: O=Cc1cn(-c2ccccc2F)cn1]

To a mixture of S-Proline (48 mg, 0.416 mmol) and CuI (79 mg, 0.416 mmol) under argon atmosphere, anh. DMSO (4 mL) was added and the mixture was stirred for 5 min at rt. Imidazole-4-carbaldehyde (200 mg, 2.08 mmol), 1-fluoro-2-iodobenzene (508 mg, 2.29 mmol) and anh. $K_2CO_3$ (863 mg, 6.24 mmol) were added and the mixture was heated at 90° C. for 16 h. The reaction mixture was cooled at rt, DCM was added and washed with $NH_4Cl$ sat. solution and brine, dried over $Na_2SO_4$, filtered and concentrated. Purification by flash chromatography, silica gel, gradient from hexane to hexane:ethyl acetate (1:1) afforded the title product (73 mg, 18% yield). $^1$H-NMR (500 MHz, $CDCl_3$), b ppm: 9.97 (s, 1H), 7.93 (m, 1H), 7.88 (m, 1H), 7.43 (m, 2H), 7.31 (m, 2H).

Examples of Preparation of an Intermediate of Formula (IIIb$_{ex}$), Method IX

Synthesis of
1-(pyridin-2-yl)-1H-pyrazole-4-carbaldehyde

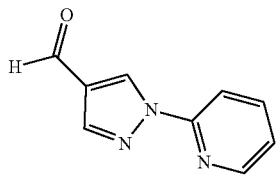 [SMILES: O=Cc1cnn(-c2ccccn2)c1]

To a solution of 2-(1H-pyrazol-1-yl)pyridine (128 mg, 0.88 mmol) in DMF (0.7 ml) at 0° C., $POCl_3$ (0.68 ml, 7.50 mmol) was added. The mixture was stirred at this temperature for 10 min and then heated at 95° C. for 3 h. Purification by flash chromatography, silica gel, gradient from hexane to ethyl acetate afforded the desired product (40 mg, 31% yield) as a yellow oil. $^1$H-NMR (400 MHz, $CDCl_3$), δ ppm: 10.00, (s, 1H), 9.10 (d, J=1 Hz, 1H), 8.46 (ddd, J=5, 2, 1 Hz, 1H), 8.17 (s, 1H), 8.03 (dt, J=8, 1 Hz, 1H), 7.22 (ddd, J=8, 8, 5 Hz, 1H), 7.30 (ddd, J=8, 5, 1 Hz, 1H).

Examples of Preparation of an Intermediate of Formula (XVIIa$_{ex}$), Method XA

Synthesis of (1-(2-fluorophenyl)-1H-1,2,3-triazol-4-yl)methanol

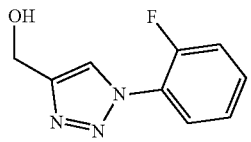 [SMILES: OCc1cn(-c2ccccc2F)nn1]

Propargyl alcohol (64 mg, 1.12 mmol) was added to a mixture of 1-azido-2-fluorobenzene (143 mg, 0.94 mmol), $CuSO_4.5H_2O$ (29 mg, 0.12 mmol) and sodium ascorbate (40 mg, 0.2 mmol) in t-BuOH:$H_2O$ 1:1 (10 mL) and the reaction mixture was stirred at rt overnight. An aqueous $NH_4Cl$ saturated solution was added and the mixture was extracted with EtOAc; the organic phase was washed with $NH_4Cl$ saturated solution, brine, dried over $Na_2SO_4$, filtered and concentrated. Purification by flash chromatography, silica gel, gradient dichloromethane to 10% methanol afforded the title product (101 mg, 56% yield). $^1$H-NMR (500 MHz, $CDCl_3$), δ ppm: 8.08 (d, J=2 Hz, 1H), 7.93 (td, J=8, 1 Hz, 1H), 7.43 (m, 1H), 7.26-7.35 (m, 2H), 4.90 (s, 2H), 2.94 (bs, 1H).

Example of Preparation of an Intermediate of Formula (XVIIb$_{ex}$), Method XI

Synthesis of
1-(pyridin-2-ylmethyl)-1H-pyrazol-4-yl)methanol

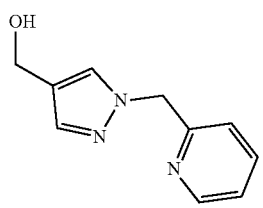 [SMILES: OCc1cnn(Cc2ccccn2)c1]

Ethyl 1-(pyridin-2-ylmethyl)-1H-pyrazole-4-carboxylate

To a solution of ethyl-1H-pyrazole-4-carboxylate (450 mg, 3.15 mmol) in acetone (6.3 mL) $K_2CO_3$ (976 mg, 7.06 mmol), 2-(chloromethyl)pyridine hydrochloride (516 mg, 3.15 mmol) and TBAI (119 mg, 0.32 mmol) was added. The mixture was heated at 60° C. overnight. The reaction mixture was cooled and filtered to remove any solids. The filtrate was concentrated. Purification by flash chromatography, silica gel, gradient hexane to ethyl acetate afforded the desired product (605 mg, 83% yield) as a yellow oil. $^1$H-NMR (300 MHz, $CDCl_3$), δ ppm: 8.57 (d, J=5 Hz, 1H), 8.03 (s, 1H), 7.94 (s, 1H), 7.65 (td, J=8, 2 Hz, 1H), 7.22 (dd, J=8, 5 Hz, 1H), 7.11 (d, J=8 Hz, 1H), 5.45 (s, 2H), 4.30 (q, J=7 Hz, 2H), 1.34 (t, J=7 Hz, 3H).

1-(Pyridin-2-ylmethyl)-1H-pyrazol-4-yl)methanol

To a solution of ethyl 1-(pyridin-2-ylmethyl)-1H-pyrazole-4-carboxylate (597 mg, 2.58 mmol) in THF (5 ml) cooled at 0° C. under inert atmosphere, $LiAlH_4$ (1M in THF, 2.58 mL, 2.58 mmol) was added dropwise. The solution was allowed to warm at rt and stirred for 2 h. An aqueous $NH_4Cl$ saturated solution was slowly added and the solvent was removed. Water and ethyl acetate were added, the organic phase was decanted, dried over $Na_2SO_4$ and filtered. The solvent was removed to afford the title product (320 mg, 65% yield). $^1$H-NMR (300 MHz, $CDCl_3$), b ppm: 8.55 (d, J=4.7 Hz, 1H), 7.64 (td, J=7.8, 2 Hz, 1H), 7.54 (d, J=4.7 Hz, 2H), 7.21 (dd, J=7.4, 4.7 Hz, 1H), 7.06 (d, J=7.8 Hz, 1H), 5.40 (s, 2H), 4.59 (s, 2H).

Example of Preparation of an Intermediate of Formula (XVIIIa$_{ex}$), Method XII Synthesis of ethyl 1-(5-fluoropyridin-2-yl)-1H-1,2,3-triazole-4-carboxylate

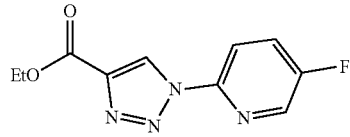 [SMILES: CCOC(=O)c1cn(-c2ccc(F)cn2)nn1]

2-Azido-5-fluoropyridine

A microwave vial was charged with a solution of 2-bromo-5-fluoropyridine (0.52 g, 2.96 mmol), NaN$_3$ (196 mg, 3.01 mmol), sodium ascorbate (31 mg, 0.15 mmol), CuI (57 mg, 0.30 mmol), N,N'-dimethylethylenediamine (49 μL, 0.44 mmol) and a mixture of EtOH:H$_2$O (7:3) (12.4 mL) and the mixture was irradiated with microwaves at 100° C. for 60 min. The reaction mixture was cooled, water was added and extracted with ethyl acetate. The organic phase was dried over Na$_2$SO$_4$ and the solvent was removed to afford the title product (0.27 g, 66% yield) as a yellow solid. $^1$H-NMR (400 MHz, CDCl$_3$), δ ppm: 8.77 (td, J=3, 1 Hz, 1H), 8.06 (dd, J=12, 6 Hz, 1H), 7.62 (ddd, J=12, 9, 3 Hz, 1H).

Ethyl 1-(5-fluoropyridin-2-yl)-1H-1,2,3-triazole-4-carboxylate

To a mixture of 2-azido-5-fluoropyridine (0.32 g, 1.97 mmol) and (CuOTf)$_2$·C$_6$H$_6$ (112 mg, 0.20 mmol) under argon, dry toluene (7.7 mL) was added, followed by ethyl propiolate (240 μL, 2.36 mmol). The reaction mixture was stirred at 100° C. overnight. Toluene was removed under reduced pressure and the reaction mixture was then diluted with dichloromethane, washed with water, brine and dried over Na$_2$SO$_4$. The mixture was filtered and the filtrate was concentrated under reduced pressure. Purification by flash chromatography, silica gel, gradient hexane to ethyl acetate afforded the desired product (450 mg, 97% yield). $^1$H-NMR (500 MHz, CDCl$_3$), δ ppm: 9.00 (s, 1H), 8.38 (d, J=3 Hz, 1H), 8.27 (dd, J=9, 4 Hz, 1H), 7.68 (ddd, J=9, 7, 3 Hz, 1H), 4.47 (q, J=7 Hz, 2H), 1.44 (t, J=7 Hz, 3H).

Example of Preparation of an Intermediate of Formula (XVIIIb$_{ex}$), Method XIII Synthesis of ethyl 2-(pyridine-2-yl)-2H-1,2,3-triazole-4-carboxylate

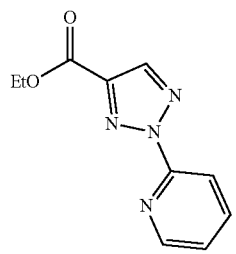 [SMILES: CCOC(=O)c1cnn(-c2ccccn2)n1]

A microwave vial was charged with ethyl 2H-1,2,3-triazole-4-carboxylate (250 mg, 1.50 mmol), K$_2$CO$_3$ (416 mg, 3.01 mmol), L-proline (35 mg, 0.30 mmol) and CuCl (15 mg, 0.15 mmol). The mixture was evacuated and back-filled with argon, DMSO (1.25 mL) and 2-bromopyridine (357 mg, 2.25 mmol) were added and the mixture was irradiated with microwaves at 160° C. for 40 min. After cooling, water was added and extracted with ethyl acetate. The combined organic phases were washed with brine and dried over Na$_2$SO$_4$. The solvent was removed under vacuum. Purification by flash chromatography, silica gel, gradient from hexane to ethyl acetate afforded the title product (40 mg, 12% yield). $^1$H-NMR (300 MHz, CDCl$_3$), δ ppm: 8.65 (m, 1H), 8.32 (s, 1H), 8.17 (m, 1H), 7.94 (m, 1H), 7.41 (m, 1H), 4.48 (q, J=7 Hz, 2H), 1.44 (t, J=7 Hz, 3H).

Synthesis of Examples

Example of Preparation of Compounds of General Formula (I$_{ex}$), Method I

Example 1: N-(3-(4-((1-phenyl-1H-1,2,3-triazol-4-yl)methyl)piperazin-1-yl)phenyl)-propane-2-sulfonamide

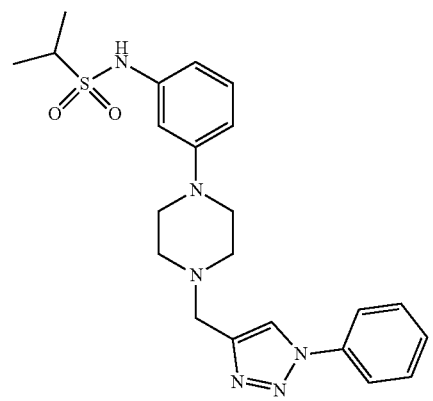 [SMILES: CC(C)S(=O)(=O)Nc1cccc(N2CCN(Cc3cn(-c4ccccc4)nn3)CC2)c1]

To a suspension of N-(3-(piperazin-1-yl)phenyl)propane-2-sulfonamide hydrochloride (1.06 g, 2.99 mmol) in dichloroethane (60 mL), N,N-diisopropylethylamine (2.09 mL, 11.98 mmol) was added and the mixture was stirred at rt for 5 min. Then, 1-phenyl-1H-1,2,3-triazole-4-carbaldehyde (0.67 g, 3.91 mmol) and NaBH(OAc)$_3$ (1.34 g, 6.03 mmol) were added and the reaction mixture was stirred at rt overnight. Dichloromethane was added and washed with NaHCO$_3$ sat solution and brine, dried over Na$_2$SO$_4$, filtered and concentrated. Purification by flash chromatography, silica gel, gradient from hexane to ethyl acetate afforded the title product (1.22 g, 93% yield). HPLC retention time: 5.61 min; HRMS: 441.2068 (M+H).

This method was used for the preparation of the examples of formula (I$_{ex}$) 1, 3-45, 47-49, 51-55, 57-73.

Example of Preparation of Compounds of General Formula (Ia$_{ex}$), Method IIB

Example 2: N-(6-(4-((1-(5-chloropyridin-3-yl)-1H-1,2,3-triazol-4-yl)methyl)-piperazin-1-yl)pyridin-2-yl)propane-2-sulfonamide

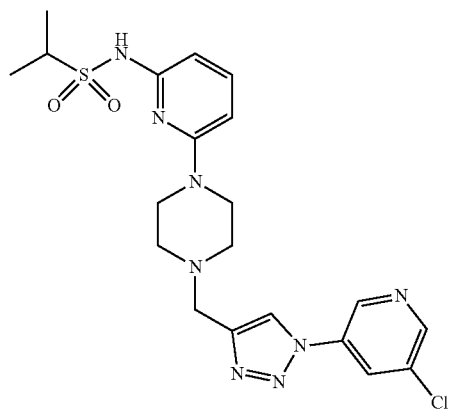 [SMILES: CC(C)S(=O)(=O)Nc1cccc(N2CCN(Cc3cn(-c4cncc(Cl)c4)nn3)CC2)n1]

A mixture of N-(6-(4-(prop-2-yn-1-yl)piperazin-1-yl)pyridin-2-yl)propane-2-sulfonamide (55 mg, 0.17 mmol), 3-azido-5-chloropyridine (40 mg, 0.25 mmol), CuSO$_4$.5H$_2$O (4.3 mg, 0.017 mmol) and sodium ascorbate (6.7 mg, 0.034 mmol) in t-BuOH:H$_2$O 1:1 (6 ml) was stirred at rt for 3 days. Ethyl acetate was added to the reaction mixture and washed with saturated NH$_4$Cl aqueous solution and brine, dried over Na$_2$SO$_4$ and concentrated. Purification was carried out by flash chromatography, silica gel, gradient hexane to acetone to afford the title product (66 mg, 81% yield). HPLC retention time: 5.27 min; HRMS: 475.1433 (M−H).

This method was used for the preparation of the examples of formula (Ia$_{ex}$) 2, 46, 50, 56.

Table of Examples with Results of HRMS and Binding to the μ-Opioid Receptor and the σ1-Receptor:

HPLC:

column: Agilent Eclipse XDB-C18, 4.6×150 mm, 5 mm, flux: 1 ml/min.

A:H$_2$O (0.05% TFA), B:ACN.

Conditions: 1°/gradient 5% to 95% B in 7 min. 2°/isocratic 95% B 5 min.

HRMS:

Source type: ESI; Ion Polarity: Positive or Negative

| EX | Structure | Chemical name | Ret time (min) | HRMS |
|---|---|---|---|---|
| 1 | (structure) | N-(3-(4-((1-phenyl-1H-1,2,3-triazol-4-yl)methyl)piperazin-1-yl)phenyl)propane-2-sulfonamide | 5.61 | 441.2068 (M + H) |
| 2 | (structure) | N-(6-(4-((1-(5-chloropyridin-3-yl)-1H-1,2,3-triazol-4-yl)methyl)piperazin-1-yl)pyridin-2-yl)propane-2-sulfonamide | 5.27 | 475.1433 (M − H) |

-continued

| EX | Structure | Chemical name | Ret time (min) | HRMS |
|---|---|---|---|---|
| 3 | 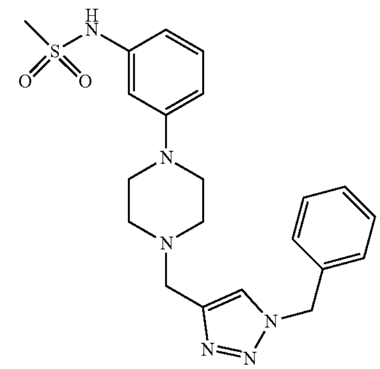 [SMILES: CS(=O)(=O)Nc1cccc(N2CCN(Cc3cn(Cc4ccccc4)nn3)CC2)c1] | N-(3-(4-((1-benzyl-1H-1,2,3-triazol-4-yl)methyl)piperazin-1-yl)phenyl) methanesulfonamide | 5.26 | 425.1758 (M − H) |
| 4 | 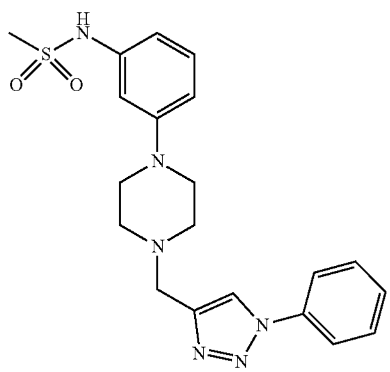 [SMILES: CS(=O)(=O)Nc1cccc(N2CCN(Cc3cn(-c4ccccc4)nn3)CC2)c1] | N-(3-(4-((1-phenyl-1H-1,2,3-triazol-4-yl)methyl)piperazin-1-yl)phenyl) methanesulfonamide | 5.22 | 413.1766 (M + H) |
| 5 | 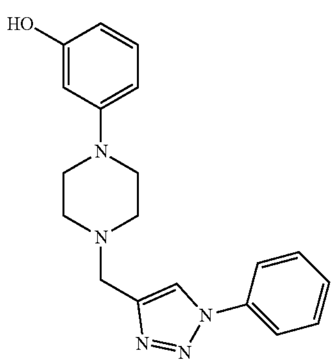 [SMILES: Oc1cccc(N2CCN(Cc3cn(-c4ccccc4)nn3)CC2)c1] | 3-(4-((1-phenyl-1H-1,2,3-triazol-4-yl)methyl)piperazin-1-yl)phenol | 5.12 | 334.1672 (M − H) |
| 6 | 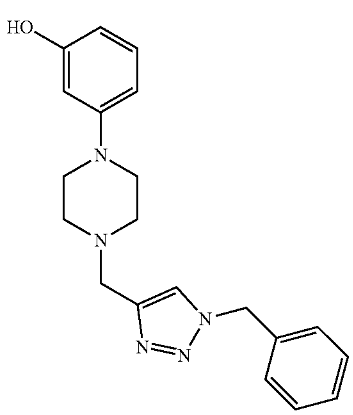 [SMILES: Oc1cccc(N2CCN(Cc3cn(Cc4ccccc4)nn3)CC2)c1] | 3-(4-((1-benzyl-1H-1,2,3-triazol-4-yl)methyl)piperazin-1-yl)phenol | 5.11 | 348.1828 (M − H) |

-continued

| EX | Structure | Chemical name | Ret time (min) | HRMS |
|---|---|---|---|---|
| 7 | 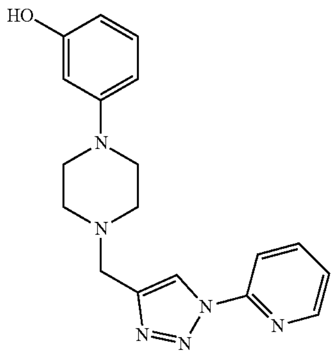 [SMILES: Oc1cccc(N2CCN(Cc3cn(-c4ccccn4)nn3)CC2)c1] | 3-(4-((1-(pyridin-2-yl)-1H-1,2,3-triazol-4-yl)methyl)piperazin-1-yl)phenol | 4.73 | 335.1620 (M − H) |
| 8 | 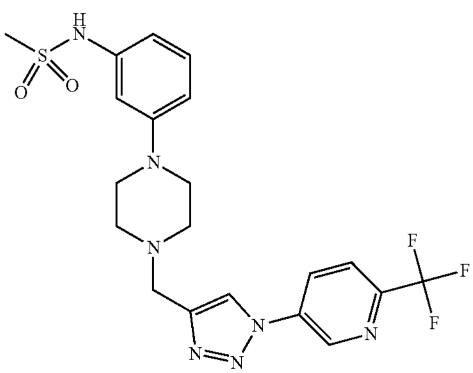 [SMILES: CS(=O)(=O)Nc1cccc(N2CCN(Cc3cn(-c4ccc(C(F)(F)F)nc4)nn3)CC2)c1] | N-(3-(4-((1-(6-(trifluoromethyl)pyridin-3-yl)-1H-1,2,3-triazol-4-yl)methyl)piperazin-1-yl)phenyl)methanesulfonamide | 5.49 | 482.1585 (M + H) |
| 9 | 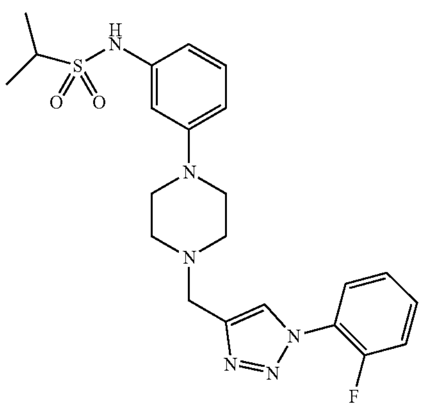 [SMILES: CC(C)S(=O)(=O)Nc1cccc(N2CCN(Cc3cn(-c4ccccc4F)nn3)CC2)c1] | N-(3-(4-((1-(2-fluorophenyl)-1H-1,2,3-triazol-4-yl)methyl)piperazin-1-yl)phenyl)propane-2-sulfonamide | 5.59 | 459.1973 (M + H) |
| 10 | 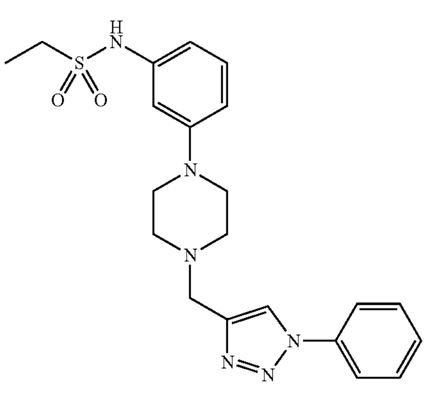 [SMILES: CCS(=O)(=O)Nc1cccc(N2CCN(Cc3cn(-c4ccccc4)nn3)CC2)c1] | N-(3-(4-((1-phenyl-1H-1,2,3-triazol-4-yl)methyl)piperazin-1-yl)phenyl)ethanesulfonamide | 5.38 | 427.1913 (M + H) |

| EX | Structure | Chemical name | Ret time (min) | HRMS |
|---|---|---|---|---|
| 11 | 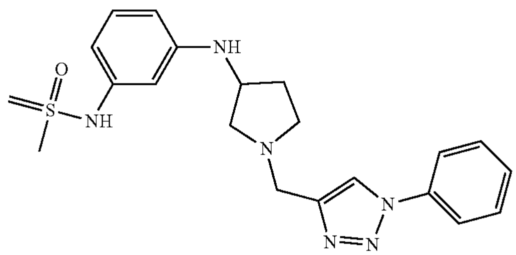 [SMILES: C=S(C)(=O)Nc1cccc(NC2CCN(Cc3cn(-c4ccccc4)nn3)C2)c1] | N-(3-(1-((1-phenyl-1H-1,2,3-triazol-4-yl)methyl)pyrrolidin-3-ylamino)phenyl) methanesulfonamide | 5.21 | 411.1601 (M − H) |
| 12 | 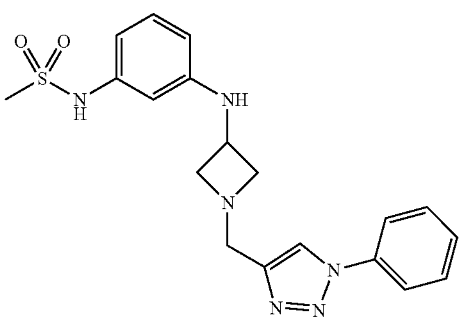 [SMILES: CS(=O)(=O)Nc1cccc(NC2CN(Cc3cn(-c4ccccc4)nn3)C2)c1] | N-(3-(1-((1-phenyl-1H-1,2,3-triazol-4-yl)methyl)azetidin-3-ylamino)phenyl) methanesulfonamide | 5.19 | 399.1609 (M + H) |
| 13 | 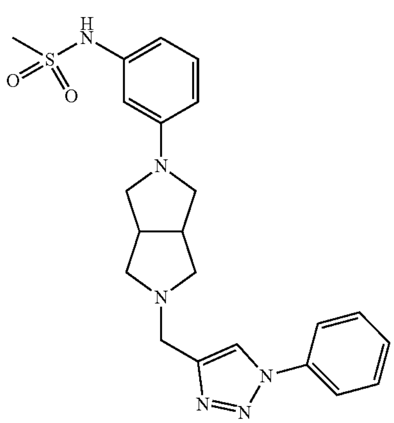 [SMILES: CS(=O)(=O)Nc1cccc(N2CC3CN(Cc4cn(-c5ccccc5)nn4)CC3C2)c1] | N-(3-(5-((1-phenyl-1H-1,2,3-triazol-4-yl)methyl) hexahydropyrrolo[3,4-c]pyrrol-2(1H)-yl)phenyl) methanesulfonamide | 5.43 | 439.1918 (M + H) |
| 14 | 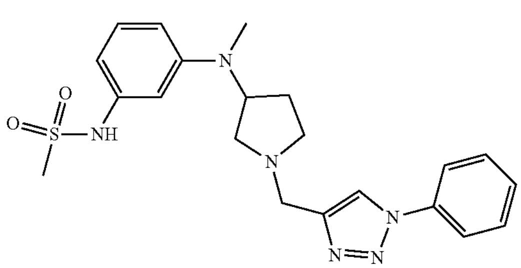 [SMILES: CN(c1cccc(NS(C)(=O)=O)c1)C1CCN(Cc2cn(-c3ccccc3)nn2)C1] | N-(3-(methyl(1-((1-phenyl-1H-1,2,3-triazol-4-yl)methyl)pyrrolidin-3-yl)amino)phenyl) methanesulfonamide | 5.40 | 427.1917 (M + H) |

| EX | Structure | Chemical name | Ret time (min) | HRMS |
|---|---|---|---|---|
| 15 | 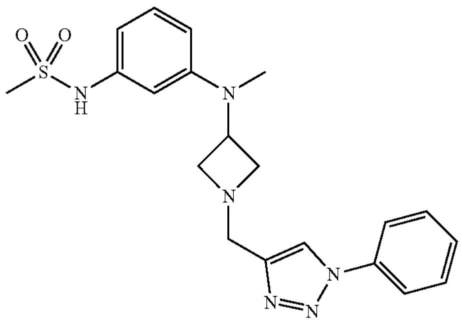 [SMILES: CN(c1cccc(NS(C)(=O)=O)c1)C1CN(Cc2cn(-c3ccccc3)nn2)C1] | N-(3-(methyl(1-((1-phenyl-1H-1,2,3-triazol-4-yl)methyl)azetidin-3-yl)amino)phenyl)methanesulfonamide | 5.35 | 413.1763 (M + H) |
| 16 | 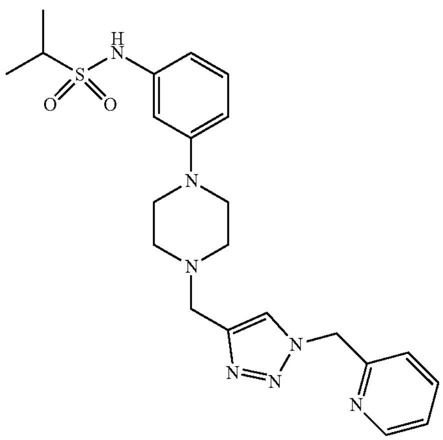 [SMILES: CC(C)S(=O)(=O)Nc1cccc(N2CCN(Cc3cn(Cc4ccccn4)nn3)CC2)c1] | N-(3-(4-((1-(pyridin-2-ylmethyl)-1H-1,2,3-triazol-4-yl)methyl)piperazin-1-yl)phenyl)propane-2-sulfonamide | 4.86 | 456.2187 (M + H) |
| 17 | 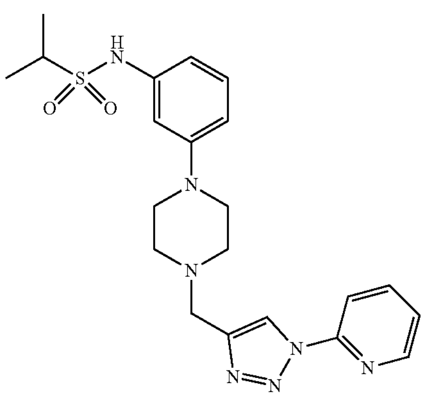 [SMILES: CC(C)S(=O)(=O)Nc1cccc(N2CCN(Cc3cn(-c4ccccn4)nn3)CC2)c1] | N-(3-(4-((1-(pyridin-2-yl)-1H-1,2,3-triazol-4-yl)methyl)piperazin-1-yl)phenyl)propane-2-sulfonamide | 5.26 | 442.2032 (M + H) |
| 18 | 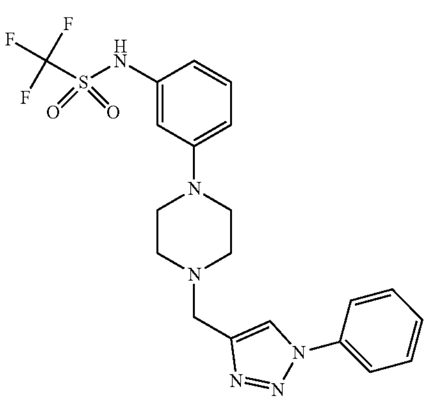 [SMILES: O=S(=O)(Nc1cccc(N2CCN(Cc3cn(-c4ccccc4)nn3)CC2)c1)C(F)(F)F] | 1,1,1-trifluoro-N-(3-(4-((1-phenyl-1H-1,2,3-triazol-4-yl)methyl)piperazin-1-yl)phenyl)methanesulfonamide | 6.14 | 467.1 (M + H) |

| EX | Structure | Chemical name | Ret time (min) | HRMS |
|---|---|---|---|---|
| 19 | 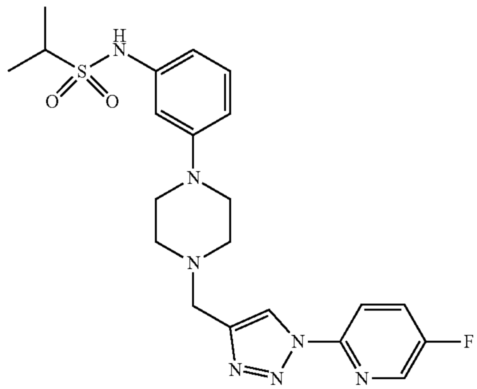 [SMILES: CC(C)S(=O)(=O)Nc1cccc(N2CCN(Cc3cn(-c4ccc(F)cn4)nn3)CC2)c1] | N-(3-(4-((1-(5-fluoropyridin-2-yl)-1H-1,2,3-triazol-4-yl)methyl)piperazin-1-yl)phenyl)propane-2-sulfonamide | 5.49 | 460.1928 (M + H) |
| 20 | 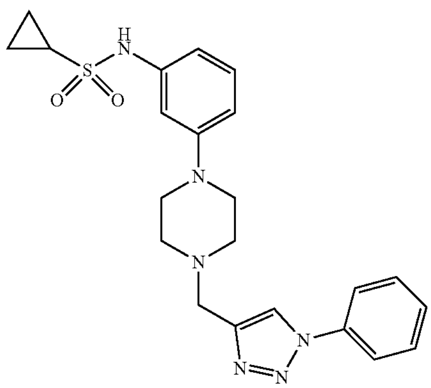 [SMILES: O=S(=O)(Nc1cccc(N2CCN(Cc3cn(-c4ccccc4)nn3)CC2)c1)C1CC1] | N-(3-(4-((1-phenyl-1H-1,2,3-triazol-4-yl)methyl)piperazin-1-yl)phenyl)cyclopropanesulfonamide | 5.14 | 437.1 (M − H) |
| 21 | 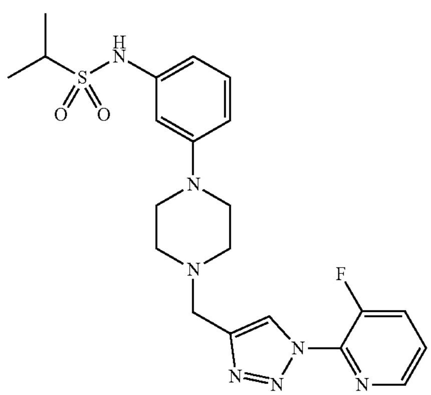 [SMILES: CC(C)S(=O)(=O)Nc1cccc(N2CCN(Cc3cn(-c4ncccc4F)nn3)CC2)c1] | N-(3-(4-((1-(3-fluoropyridin-2-yl)-1H-1,2,3-triazol-4-yl)methyl)piperazin-1-yl)phenyl)propane-2-sulfonamide | 5.17 | 460.1936 (M + H) |
| 22 | 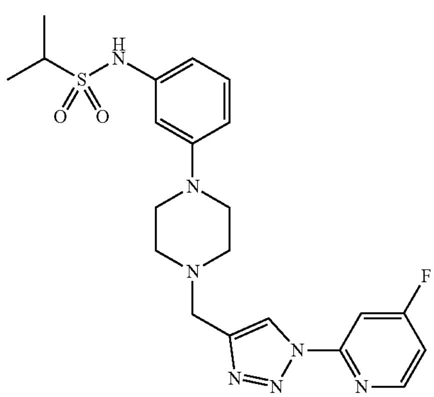 [SMILES: CC(C)S(=O)(=O)Nc1cccc(N2CCN(Cc3cn(-c4cc(F)ccn4)nn3)CC2)c1] | N-(3-(4-((1-(4-fluoropyridin-2-yl)-1H-1,2,3-triazol-4-yl)methyl)piperazin-1-yl)phenyl)propane-2-sulfonamide | 5.49 | 460.1934 (M + H) |

| EX | Structure | Chemical name | Ret time (min) | HRMS |
|---|---|---|---|---|
| 23 | 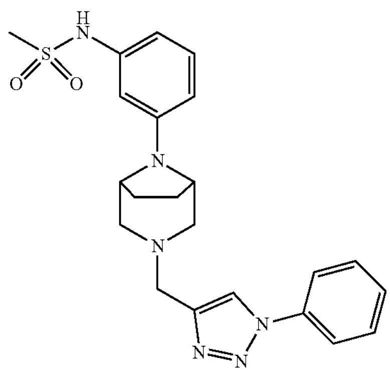 [SMILES: CS(=O)(=O)Nc1cccc(N2C3CCC2CN(Cc2cn(-c4ccccc4)nn2)C3)c1] | N-(3-((1R,5S)-3-((1-phenyl-1H-1,2,3-triazol-4-yl)methyl)-3,8-diazabicyclo[3.2.1]octan-8-yl)phenyl)methanesulfonamide | 5.30 | 439.1912 (M + H) |
| 24 | 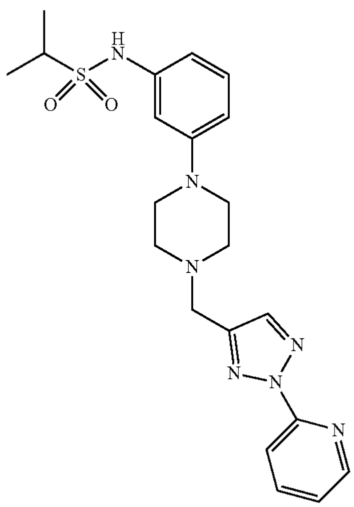 [SMILES: CC(C)S(=O)(=O)Nc1cccc(N2CCN(Cc3cnn(-c4ccccn4)n3)CC2)c1] | N-(3-(4-((2-(pyridin-2-yl)-2H-1,2,3-triazol-4-yl)methyl)piperazin-1-yl)phenyl)propane-2-sulfonamide | 5.18 | 442.2028 (M + H) |
| 25 | 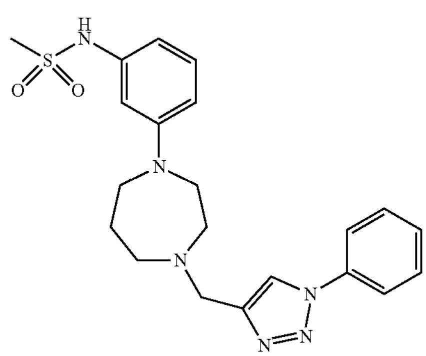 [SMILES: CS(=O)(=O)Nc1cccc(N2CCCN(Cc3cn(-c4ccccc4)nn3)CC2)c1] | N-(3-(4-((1-phenyl-1H-1,2,3-triazol-4-yl)methyl)-1,4-diazepan-1-yl)phenyl)methanesulfonamide | 5.35 | 427.2 (M + H) |

-continued

| EX | Structure | Chemical name | Ret time (min) | HRMS |
|---|---|---|---|---|
| 26 | 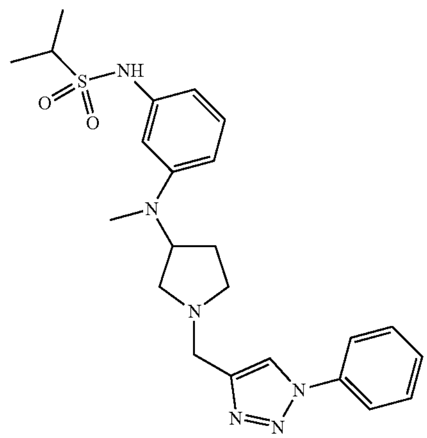 [SMILES: CC(C)S(=O)(=O)Nc1cccc(N(C)C2CCN(Cc3cn(-c4ccccc4)nn3)C2)c1] | N-(3-(methyl(1-((1-phenyl-1H-1,2,3-triazol-4-yl)methyl)pyrrolidin-3-yl)amino)phenyl)propane-2-sulfonamide | 5.81 | 455.2236 (M + H) |
| 27 | 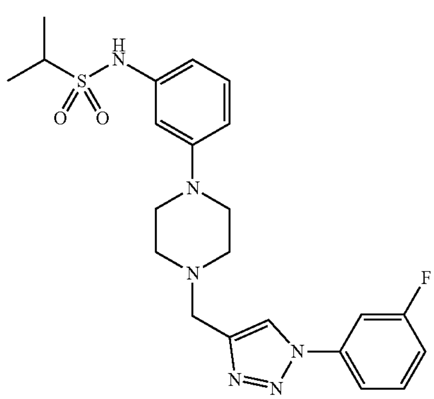 [SMILES: CC(C)S(=O)(=O)Nc1cccc(N2CCN(Cc3cn(-c4cccc(F)c4)nn3)CC2)c1] | N-(3-(4-((1-(3-fluorophenyl)-1H-1,2,3-triazol-4-yl)methyl)piperazin-1-yl)phenyl)propane-2-sulfonamide | 5.78 | 459.1980 (M + H) |
| 28 | 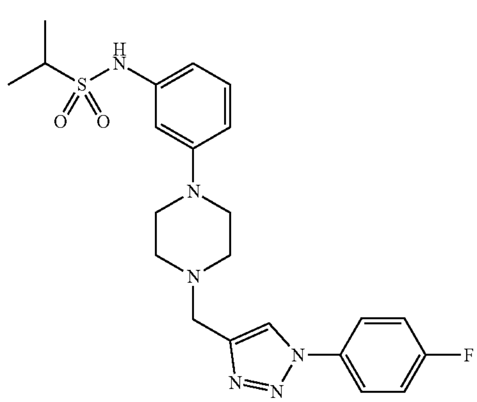 [SMILES: CC(C)S(=O)(=O)Nc1cccc(N2CCN(Cc3cn(-c4ccc(F)cc4)nn3)CC2)c1] | N-(3-(4-((1-(4-fluorophenyl)-1H-1,2,3-triazol-4-yl)methyl)piperazin-1-yl)phenyl)propane-2-sulfonamide | 5.74 | 459.1981 (M + H) |

-continued

| EX | Structure | Chemical name | Ret time (min) | HRMS |
|---|---|---|---|---|
| 29 | 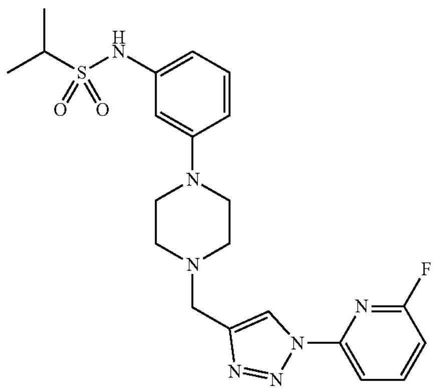 [SMILES: CC(C)S(=O)(=O)Nc1cccc(N2CCN(Cc3cn(-c4cccc(F)n4)nn3)CC2)c1] | N-(3-(4-((1-(6-fluoropyridin-2-yl)-1H-1,2,3-triazol-4-yl)methyl)piperazin-1-yl)phenyl)propane-2-sulfonamide | 5.56 | 458.1781 (M − H) |
| 30 | 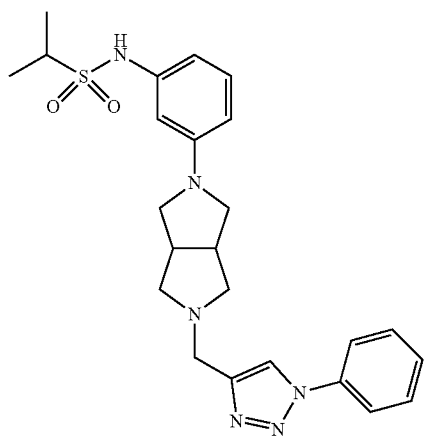 [SMILES: CC(C)S(=O)(=O)Nc1cccc(N2CC3CN(Cc4cn(-c5ccccc5)nn4)CC3C2)c1] | N-(3-(5-((1-phenyl-1H-1,2,3-triazol-4-yl)methyl)hexahydropyrrolo[3,4-c]pyrrol-2(1H)-yl)phenyl)propane-2-sulfonamide | 5.88 | 465.2 (M − H) |
| 31 | 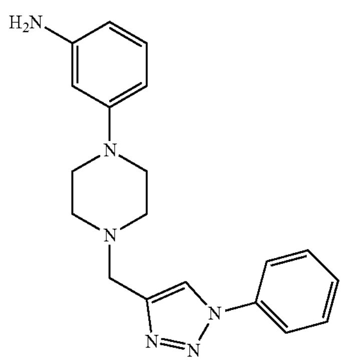 [SMILES: Nc1cccc(N2CCN(Cc3cn(-c4ccccc4)nn3)CC2)c1] | 3-(4-((1-phenyl-1H-1,2,3-triazol-4-yl)methyl)piperazin-1-yl)aniline | 4.45 | 335.1983 (M + H) |
| 32 | 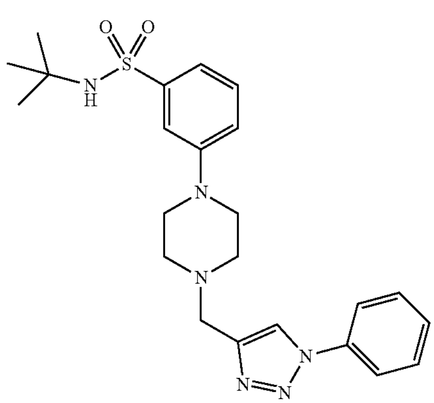 [SMILES: CC(C)(C)NS(=O)(=O)c1cccc(N2CCN(Cc3cn(-c4ccccc4)nn3)CC2)c1] | N-tert-butyl-3-(4-((1-phenyl-1H-1,2,3-triazol-4-yl)methyl)piperazin-1-yl)benzenesulfonamide | 5.01 | 455.2227 (M + H) |

-continued
| EX | Structure | Chemical name | Ret time (min) | HRMS |
|---|---|---|---|---|
| 33 | 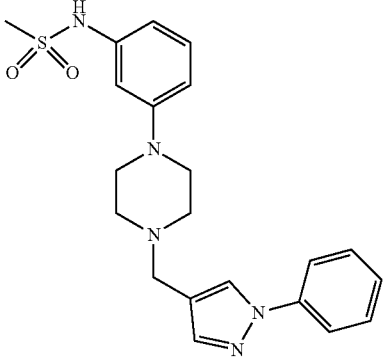 | N-(3-(4-((1-phenyl-1H-pyrazol-4-yl)methyl)piperazin-1-yl)phenyl)methanesulfonamide | 4.88 | 410.1666 (M − H) |
| 34 | 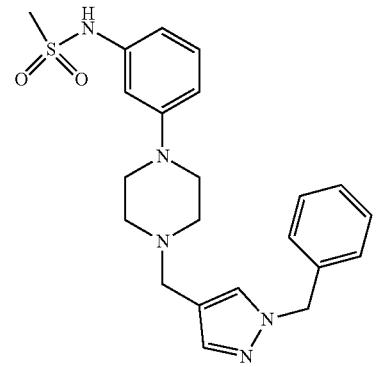 [SMILES: CS(=O)(=O)Nc1cccc(N2CCN(Cc3cnn(Cc4ccccc4)c3)CC2)c1] | N-(3-(4-((1-benzyl-1H-pyrazol-4-yl)methyl)piperazin-1-yl)phenyl)methanesulfonamide | 5.29 | 424.1813 (M − H) |
| 35 | 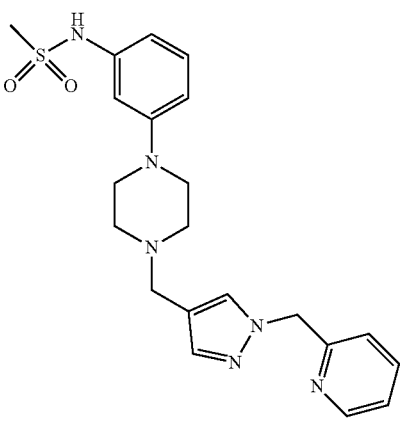 [SMILES: CS(=O)(=O)Nc1cccc(N2CCN(Cc3cnn(Cc4ccccn4)c3)CC2)c1] | N-(3-(4-((1-(pyridin-2-ylmethyl)-1H-pyrazol-4-yl)methyl)piperazin-1-yl)phenyl)methanesulfonamide | 4.27 | 425.1767 (M − H) |
| 36 | 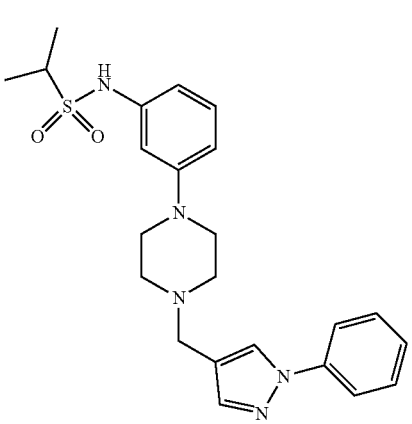 [SMILES: CC(C)S(=O)(=O)Nc1cccc(N2CCN(Cc3cnn(-c4ccccc4)c3)CC2)c1] | N-(3-(4-((1-phenyl-1H-pyrazol-4-yl)methyl)piperazin-1-yl)phenyl)propane-2-sulfonamide | 5.69 | 438.1963 (M − H) |

| EX | Structure | Chemical name | Ret time (min) | HRMS |
|---|---|---|---|---|
| 37 | 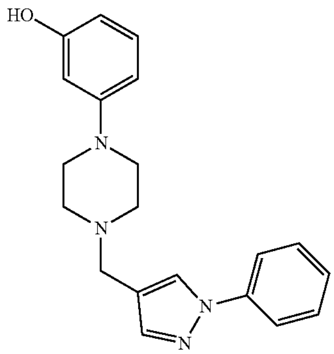 [SMILES: Oc1cccc(N2CCN(Cc3cnn(-c4ccccc4)c3)CC2)c1] | 3-(4-((1-phenyl-1H-pyrazol-4-yl)methyl)piperazin-1-yl)phenol | 5.26 | 333.1720 (M − H) |
| 38 | 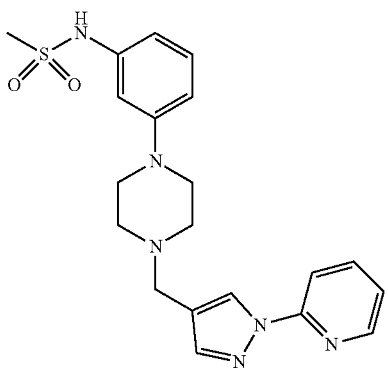 [SMILES: CS(=O)(=O)Nc1cccc(N2CCN(Cc3cnn(-c4ccccn4)c3)CC2)c1] | N-(3-(4-((1-(pyridin-2-yl)-1H-pyrazol-4-yl)methyl)piperazin-1-yl)phenyl)methanesulfonamide | 5.04 | 413.1755 (M + H) |
| 39 | 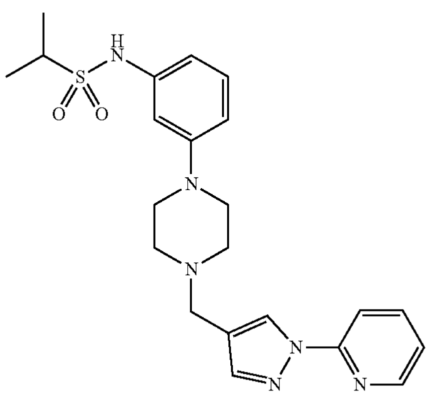 [SMILES: CC(C)S(=O)(=O)Nc1cccc(N2CCN(Cc3cnn(-c4ccccn4)c3)CC2)c1] | N-(3-(4-((1-(pyridin-2-yl)-1H-pyrazol-4-yl)methyl)piperazin-1-yl)phenyl)propane-2-sulfonamide | 5.12 | 441.2083 (M + H) |
| 40 | 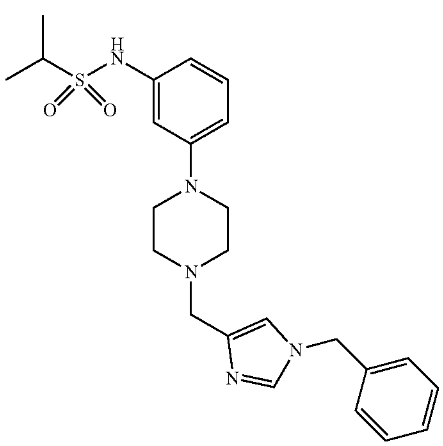 [SMILES: CC(C)S(=O)(=O)Nc1cccc(N2CCN(Cc3cn(Cc4ccccc4)cn3)CC2)c1] | N-(3-(4-((1-benzyl-1H-imidazol-4-yl)methyl)piperazin-1-yl)phenyl)propane-2-sulfonamide | 5.09 | 452.2120 (M − H) |

-continued

| EX | Structure | Chemical name | Ret time (min) | HRMS |
|---|---|---|---|---|
| 41 | 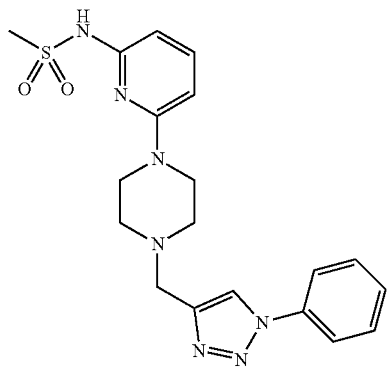 [SMILES: CS(=O)(=O)Nc1cccc(N2CCN(Cc3cn(-c4ccccc4)nn3)CC2)n1] | N-(6-(4-((1-phenyl-1H-1,2,3-triazol-4-yl)methyl)piperazin-1-yl)pyridin-2-yl)methanesulfonamide | 5.10 | 414.1721 (M + H) |
| 42 | 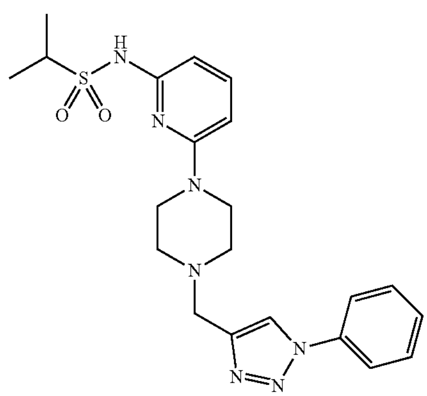 [SMILES: CC(C)S(=O)(=O)Nc1cccc(N2CCN(Cc3cn(-c4ccccc4)nn3)CC2)n1] | N-(6-(4-((1-phenyl-1H-1,2,3-triazol-4-yl)methyl)piperazin-1-yl)pyridin-2-yl)propane-2-sulfonamide | 5.47 | 442.2022 (M + H) |
| 43 | 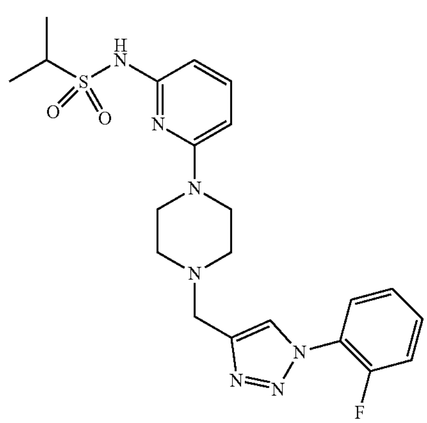 [SMILES: CC(C)S(=O)(=O)Nc1cccc(N2CCN(Cc3cn(-c4ccccc4F)nn3)CC2)n1] | N-(6-(4-((1-(2-fluorophenyl)-1H-1,2,3-triazol-4-yl)methyl)piperazin-1-yl)pyridin-2-yl)propane-2-sulfonamide | 5.54 | 460.1922 (M + H) |

| EX | Structure | Chemical name | Ret time (min) | HRMS |
|---|---|---|---|---|
| 44 | 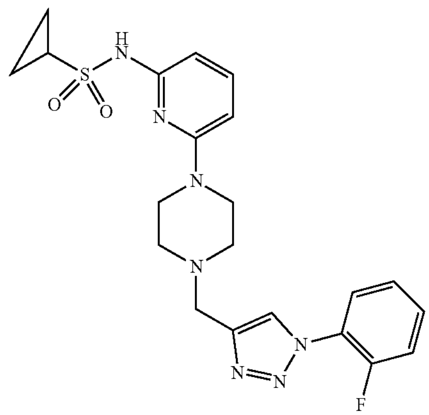 [SMILES: O=S(=O)(Nc1cccc(N2CCN(Cc3cn(-c4ccccc4F)nn3)CC2)n1)C1CC1] | N-(6-(4-((1-(2-fluorophenyl)-1H-1,2,3-triazol-4-yl)methyl)piperazin-1-yl)pyridin-2-yl)cyclopropanesulfonamide | 5.47 | 458.1768 (M + H) |
| 45 | 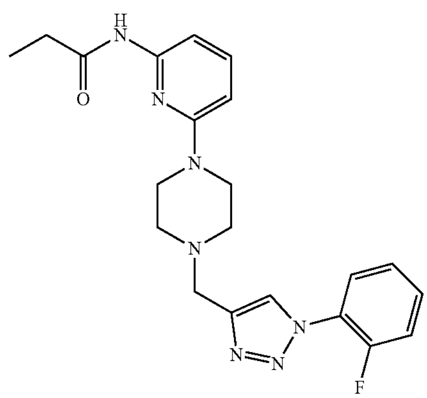 [SMILES: CCC(=O)Nc1cccc(N2CCN(Cc3cn(-c4ccccc4F)nn3)CC2)n1] | N-(6-(4-((1-(2-fluorophenyl)-1H-1,2,3-triazol-4-yl)methyl)piperazin-1-yl)pyridin-2-yl)propionamide | 5.30 | 410.2092 (M + H) |
| 46 | 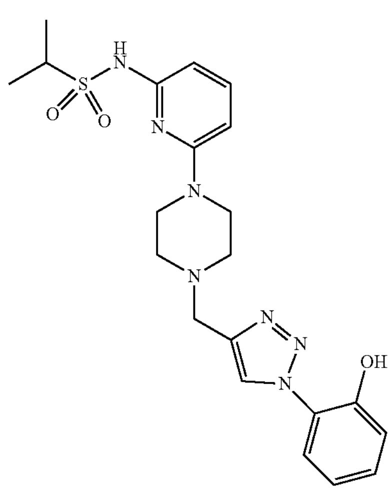 [SMILES: CC(C)S(=O)(=O)Nc1cccc(N2CCN(Cc3cn(-c4ccccc4O)nn3)CC2)n1] | N-(6-(4-((1-(2-hydroxyphenyl)-1H-1,2,3-triazol-4-yl)methyl)piperazin-1-yl)pyridin-2-yl)propane-2-sulfonamide | 5.23 | 456.1819 (M − H) |

| EX | Structure | Chemical name | Ret time (min) | HRMS |
|---|---|---|---|---|
| 47 | 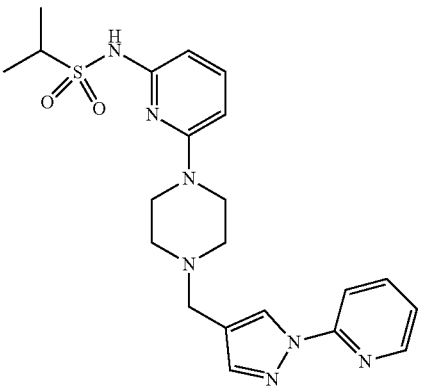 [SMILES: CC(C)S(=O)(=O)Nc1cccc(N2CCN(Cc3cnn(-c4ccccn4)c3)CC2)n1] | N-(6-(4-((1-(pyridin-2-yl)-1H-pyrazol-4-yl)methyl)piperazin-1-yl)pyridin-2-yl)propane-2-sulfonamide | 5.27 | 442.1 (M + H) |
| 48 | 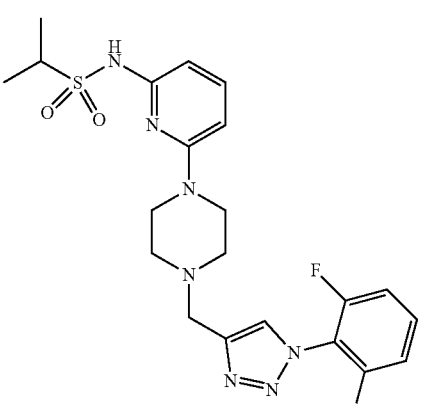 | N-(6-(4-((1-(2,6-difluorophenyl)-1H-1,2,3-triazol-4-yl)methyl)piperazin-1-yl)pyridin-2-yl)propane-2-sulfonamide | 5.48 | 478.1 (M + H) |
| 49 | 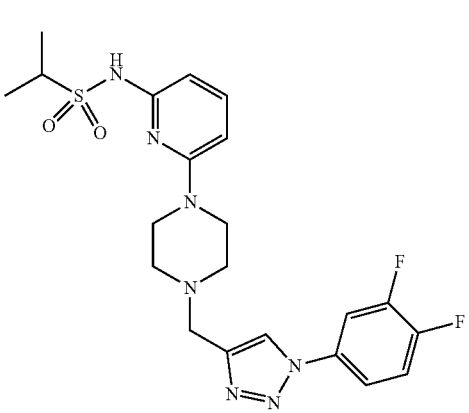 [SMILES: CC(C)S(=O)(=O)Nc1cccc(N2CCN(Cc3cn(-c4ccc(F)c(F)c4)nn3)CC2)n1] | N-(6-(4-((1-(3,4-difluorophenyl)-1H-1,2,3-triazol-4-yl)methyl)piperazin-1-yl)pyridin-2-yl)propane-2-sulfonamide | 5.70 | 478.1 (M + H) |

-continued

| EX | Structure | Chemical name | Ret time (min) | HRMS |
|---|---|---|---|---|
| 50 | 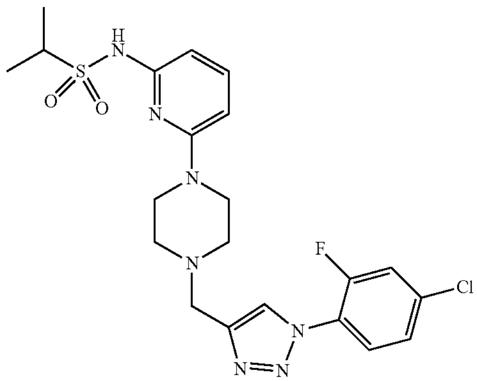 [SMILES: CC(C)S(=O)(=O)Nc1cccc(N2CCN(Cc3cn(-c4ccc(Cl)cc4F)nn3)CC2)n1] | N-(6-(4-((1-(4-chloro-2-fluorophenyl)-1H-1,2,3-triazol-4-yl)methyl)piperazin-1-yl)pyridin-2-yl)propane-2-sulfonamide | 5.82 | 494.1549 (M + H) |
| 51 | 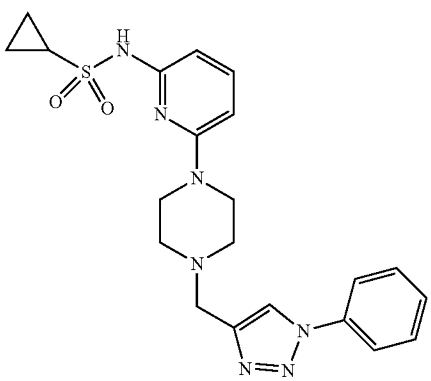 [SMILES: O=S(=O)(Nc1cccc(N2CCN(Cc3cn(-c4ccccc4)nn3)CC2)n1)C1CC1] | N-(6-(4-((1-phenyl-1H-1,2,3-triazol-4-yl)methyl)piperazin-1-yl)pyridin-2-yl) cyclopropanesulfonamide | 5.35 | 440.1861 (M + H) |
| 52 | 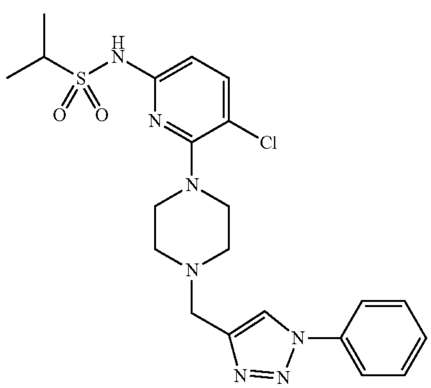 [SMILES: CC(C)S(=O)(=O)Nc1ccc(Cl)c(N2CCN(Cc3cn(-c4ccccc4)nn3)CC2)n1] | N-(5-chloro-6-(4-((1-phenyl-1H-1,2,3-triazol-4-yl)methyl)piperazin-1-yl)pyridin-2-yl)propane-2-sulfonamide | 5.69 | 476.1636 (M + H) |

-continued

| EX | Structure | Chemical name | Ret time (min) | HRMS |
|---|---|---|---|---|
| 53 | 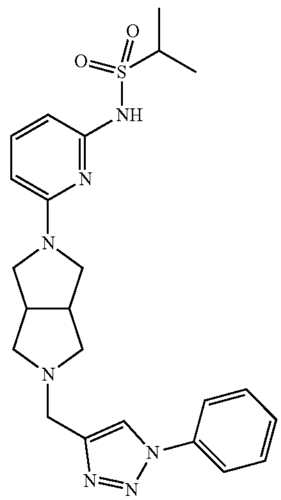 [SMILES: CC(C)S(=O)(=O)Nc1cccc(N2CC3CN(Cc4cn(-c5ccccc5)nn4)CC3C2)n1] | N-(6-(5-((1-phenyl-1H-1,2,3-triazol-4-yl)methyl) hexahydropyrrolo [3,4-c]pyrrol-2(1H)-yl)pyridin-2-yl)propane-2-sulfonamide | 5.55 | 468.2179 (M + H) |
| 54 | 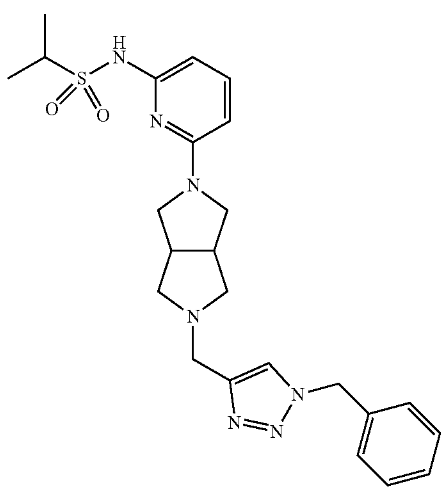 [SMILES: CC(C)S(=O)(=O)Nc1cccc(N2CC3CN(Cc4cn(Cc5ccccc5)nn4)CC3C2)n1] | N-(6-(5-((1-benzyl-1H-1,2,3-triazol-4-yl)methyl) hexahydropyrrolo [3,4-c]pyrrol-2(1H)-yl)pyridin-2-yl)propane-2-sulfonamide | 5.51 | 482.2335 (M + H) |
| 55 | 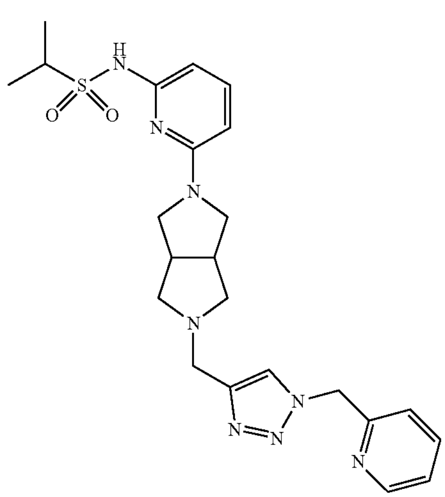 [SMILES: CC(C)S(=O)(=O)Nc1cccc(N2CC3CN(Cc4cn(Cc5ccccn5)nn4)CC3C2)n1] | N-(6-(5-((1-(pyridin-2-ylmethyl)-1H-1,2,3-triazol-4-yl)methyl) hexahydropyrrolo [3,4-c]pyrrol-2(1H)-yl)pyridin-2-yl)propane-2-sulfonamide | 4.84 | 483.2284 (M + H) |

| EX | Structure | Chemical name | Ret time (min) | HRMS |
|---|---|---|---|---|
| 56 | 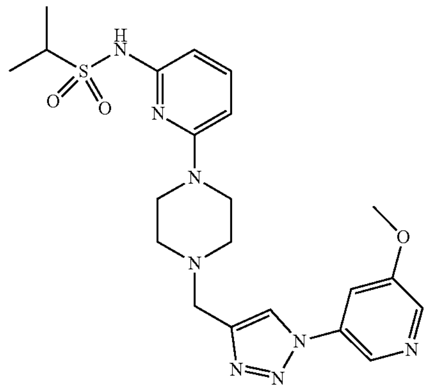 [SMILES: COc1cncc(-n2cc(CN3CCN(c4cccc(NS(=O)(=O)C(C)C)n4)CC3)nn2)c1] | N-(6-(4-((1-(5-methoxypyridin-3-yl)-1H-1,2,3-triazol-4-yl)methyl)piperazin-1-yl)pyridin-2-yl)propane-2-sulfonamide | 5.01 | 473.2068 (M + H) |
| 57 | 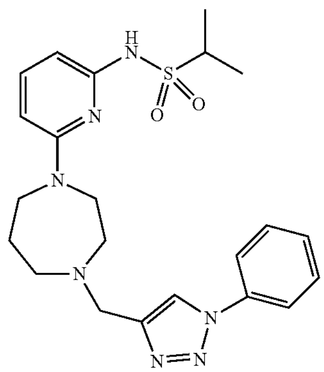 [SMILES: CC(C)S(=O)(=O)Nc1cccc(N2CCCN(Cc3cn(-c4ccccc4)nn3)CC2)n1] | N-(6-(4-((1-phenyl-1H-1,2,3-triazol-4-yl)methyl)-1,4-diazepan-1-yl)pyridin-2-yl)propane-2-sulfonamide | 5.54 | 456.2182 (M + H) |
| 58 | 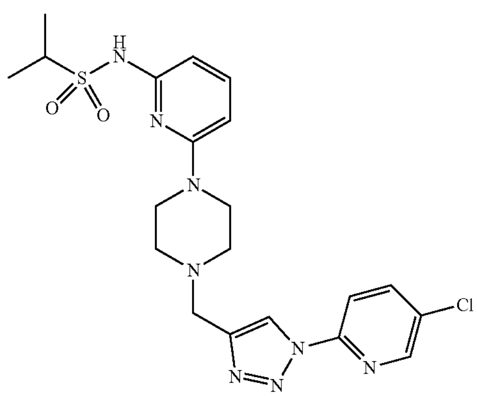 [SMILES: CC(C)S(=O)(=O)Nc1cccc(N2CCN(Cc3cn(-c4ccc(Cl)cn4)nn3)CC2)n1] | N-(6-(4-((1-(5-chloropyridin-2-yl)-1H-1,2,3-triazol-4-yl)methyl)piperazin-1-yl)pyridin-2-yl)propane-2-sulfonamide | 5.59 | 477.1580 (M + H) |
| 59 | 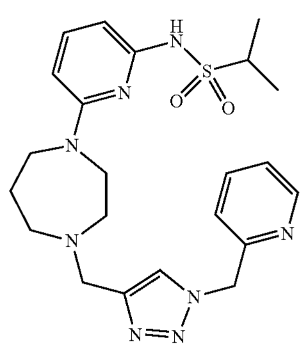 [SMILES: CC(C)S(=O)(=O)Nc1cccc(N2CCCN(Cc3cn(Cc4ccccn4)nn3)CC2)n1] | N-(6-(4-((1-(pyridin-2-ylmethyl)-1H-1,2,3-triazol-4-yl)methyl)-1,4-diazepan-1-yl)pyridin-2-yl)propane-2-sulfonamide | 4.80 | 493.2111 (M + Na) |

| EX | Structure | Chemical name | Ret time (min) | HRMS |
|---|---|---|---|---|
| 60 | 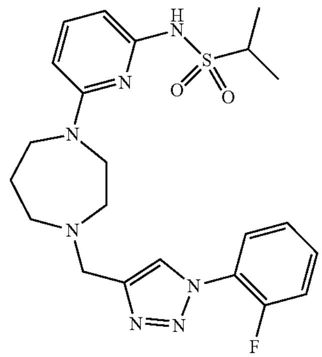 [SMILES: CC(C)S(=O)(=O)Nc1cccc(N2CCCN(Cc3cn(-c4ccccc4F)nn3)CC2)n1] | N-(6-(4-((1-(2-fluorophenyl)-1H-1,2,3-triazol-4-yl)methyl)-1,4-diazepan-1-yl)pyridin-2-yl)propane-2-sulfonamide | 5.57 | 474.2094 (M + H) |
| 61 | 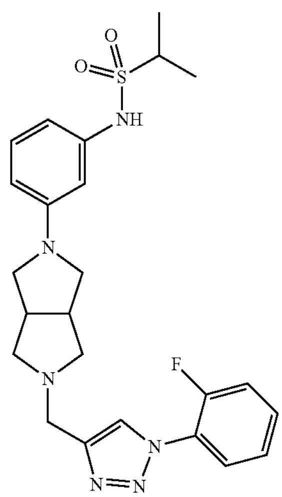 [SMILES: CC(C)S(=O)(=O)Nc1cccc(N2CC3CN(Cc4cn(-c5ccccc5F)nn4)CC3C2)c1] | N-(6-(5-((1-(2-fluorophenyl)-1H-1,2,3-triazol-4-yl)methyl) hexahydropyrrolo [3,4-c]pyrrol-2(1H)-yl)pyridin-2-yl)propane-2-sulfonamide | 5.57 | 486.2079 (M + H) |
| 62 | 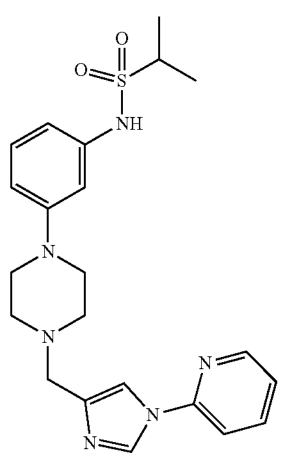 [SMILES: CC(C)S(=O)(=O)Nc1cccc(N2CCN(Cc3cn(-c4ccccn4)cn3)CC2)c1] | N-(6-(4-((1-(pyridin-2-yl)-1H-imidazol-4-yl)methyl)piperazin-1-yl)pyridin-2-yl)propane-2-sulfonamide | 4.89 | 442.2018 (M + H) |

-continued
| EX | Structure | Chemical name | Ret time (min) | HRMS |
|---|---|---|---|---|
| 63 | 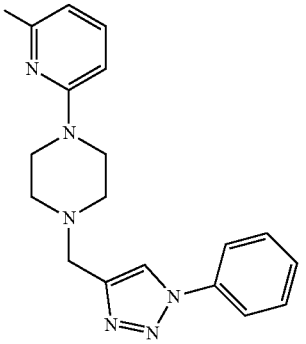 | 6-(4-((1-phenyl-1H-1,2,3-triazol-4-yl)methyl)piperazin-1-yl)pyridin-2-amine | 4.40 | 336.1922 (M + H) |
| 64 | 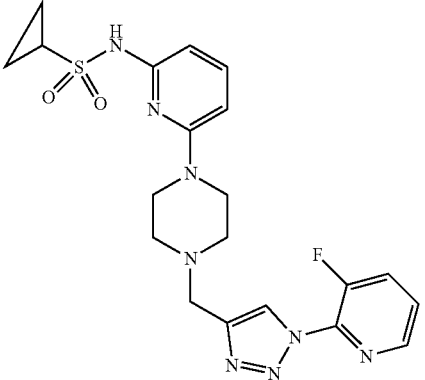 [SMILES: O=S(=O)(Nc1cccc(N2CCN(Cc3cn(-c4ncccc4F)nn3)CC2)n1)C1CC1] | N-(6-(4-((1-(3-fluoropyridin-2-yl)-1H-1,2,3-triazol-4-yl)methyl)piperazin-1-yl)pyridin-2-yl)cyclopropanesulfonamide | 5.03 | 457.1562 (M − H) |
| 65 | 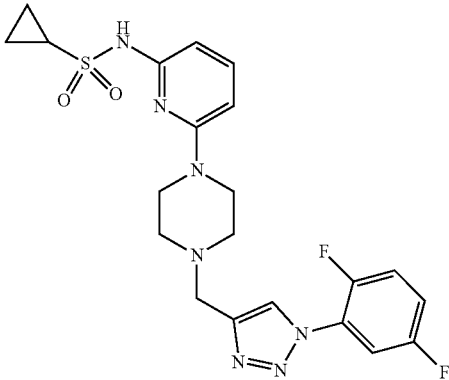 [SMILES: O=S(=O)(Nc1cccc(N2CCN(Cc3cn(-c4cc(F)ccc4F)nn3)CC2)n1)C1CC1] | N-(6-(4-((1-(2,5-difluorophenyl)-1H-1,2,3-triazol-4-yl)methyl)piperazin-1-yl)pyridin-2-yl)cyclopropanesulfonamide | 5.56 | 476.1680 (M + H) |

-continued

| EX | Structure | Chemical name | Ret time (min) | HRMS |
|---|---|---|---|---|
| 66 | 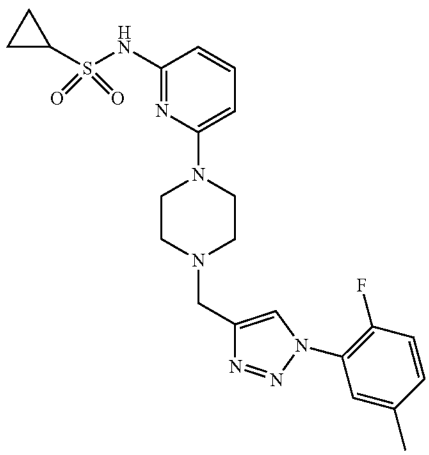 [SMILES: Cc1ccc(F)c(-n2cc(CN3CCN(c4cccc(NS(=O)(=O)C5CC5)n4)CC3)nn2)c1] | N-(6-(4-((1-(2-fluoro-5-methylphenyl)-1H-1,2,3-triazol-4-yl)methyl)piperazin-1-yl)pyridin-2-yl)cyclopropanesulfonamide | 5.72 | 472.1907 (M + H) |
| 67 | 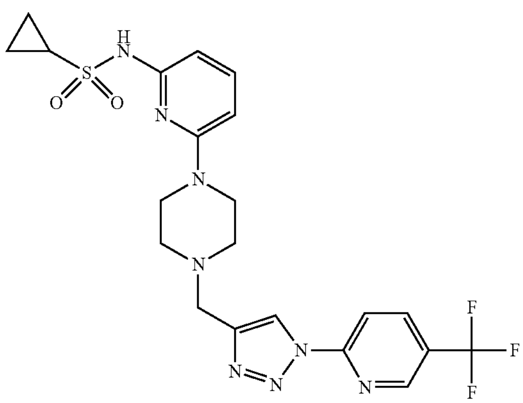 [SMILES: O=S(=O)(Nc1cccc(N2CCN(Cc3cn(-c4ccc(C(F)(F)F)cn4)nn3)CC2)n1)C1CC1] | N-(6-(4-((1-(5-(trifluoromethyl)pyridin-2-yl)-1H-1,2,3-triazol-4-yl)methyl)piperazin-1-yl)pyridin-2-yl)cyclopropanesulfonamide | 5.82 | 509.1684 (M + H) |
| 68 | 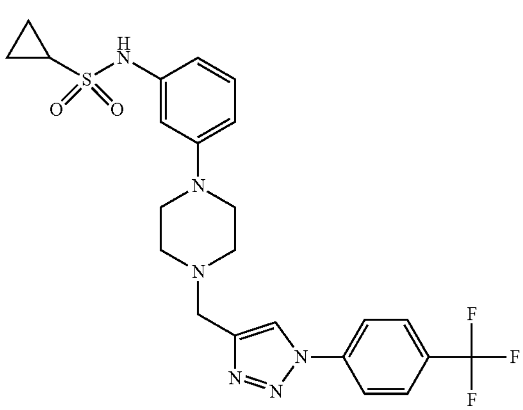 [SMILES: O=S(=O)(Nc1cccc(N2CCN(Cc3cn(-c4ccc(C(F)(F)F)cc4)nn3)CC2)c1)C1CC1] | N-(6-(4-((1-(4-(trifluoromethyl)phenyl)-1H-1,2,3-triazol-4-yl)methyl)piperazin-1-yl)pyridin-2-yl)cyclopropanesulfonamide | 6.04 | 508.1738 (M + H) |

| EX | Structure | Chemical name | Ret time (min) | HRMS |
|---|---|---|---|---|
| 69 | 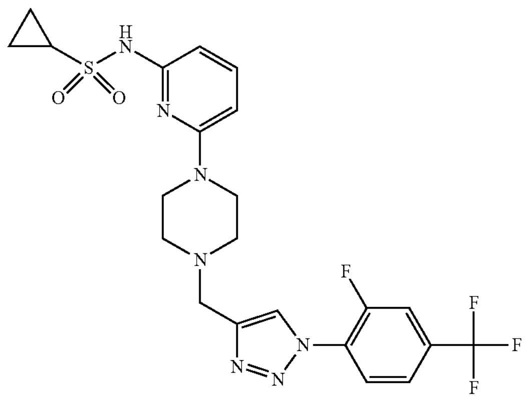 [SMILES: O=S(=O)(Nc1cccc(N2CCN(Cc3cn(-c4ccc(C(F)(F)F)cc4F)nn3)CC2)n1)C1CC1] | N-(6-(4-((1-(2-fluoro-4-(trifluoromethyl)phenyl)-1H-1,2,3-triazol-4-yl)methyl)piperazin-1-yl)pyridin-2-yl)cyclopropanesulfonamide | 6.05 | 524.0 (M − H) |
| 70 | 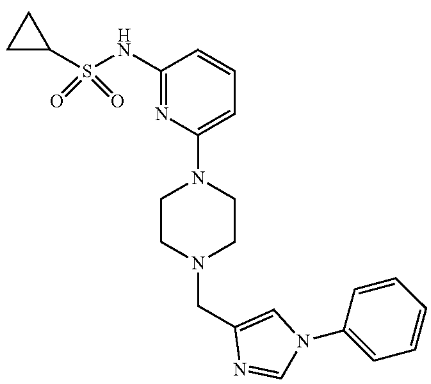 [SMILES: O=S(=O)(Nc1cccc(N2CCN(Cc3cn(-c4ccccc4)cn3)CC2)n1)C1CC1] | N-(6-(4-((1-phenyl-1H-imidazol-4-yl)methyl)piperazin-1-yl)pyridin-2-yl)cyclopropanesulfonamide | 5.25 | 439.1932 (M + H) |
| 71 | 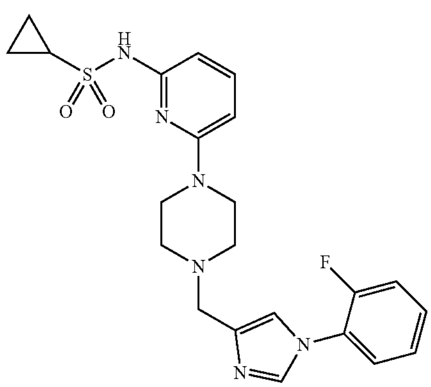 [SMILES: O=S(=O)(Nc1cccc(N2CCN(Cc3cn(-c4ccccc4F)cn3)CC2)n1)C1CC1] | N-(6-(4-((1-(2-fluorophenyl)-1H-imidazol-4-yl)methyl)piperazin-1-yl)pyridin-2-yl)cyclopropanesulfonamide | 5.34 | 457.1824 (M + H) |
| 72 | 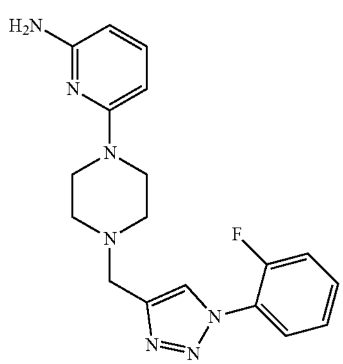 [SMILES: Nc1cccc(N2CCN(Cc3cn(-c4ccccc4F)nn3)CC2)n1] | 6-(4-((1-(2-fluorophenyl)-1H-1,2,3-triazol-4-yl)methyl)piperazin-1-yl)pyridin-2-amine | 4.25 | 376.1653 (M + Na) |

| EX | Structure | Chemical name | Ret time (min) | HRMS |
|---|---|---|---|---|
| 73 | 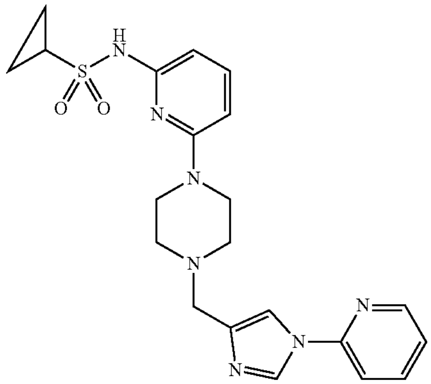 [SMILES: O=S(=O)(Nc1cccc(N2CCN(Cc3cn(-c4ccccn4)cn3)CC2)n1)C1CC1] | N-(6-(4-((1-(pyridin-2-yl)-1H-imidazol-4-yl)methyl)piperazin-1-yl)pyridin-2-yl) cyclopropanesulfonamide | 4.94 | 440.1863 (M + H) |

Biological Activity
Pharmacological Study
Human $\sigma_1$ Receptor Radioligand Assay To investigate binding properties of $\sigma_1$ receptor ligands to human $\sigma_1$ receptor, transfected HEK-293 membranes and [$^3$H](+)-pentazocine (Perkin Elmer, NET-1056), as the radioligand, were used. The assay was carried out with 7 μg of membrane suspension, 5 nM of [$^3$H](+)-pentazocine in either absence or presence of either buffer or 10 μM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH7.4). Filters were dried and counted at approximately 40% efficiency in a MicroBeta scintillation counter (Perkin-Elmer) using EcoScint liquid scintillation cocktail Human μ-Opioid Receptor Radioligand Assay To investigate binding properties of p-opioid receptor ligands to human p-opioid receptor, transfected CHO-K1 cell membranes and [$^3$H]-DAMGO (Perkin Elmer, ES-542-C), as the radioligand, were used. The assay was carried out with 20 μg of membrane suspension, 1 nM of [$^3$H]-DAMGO in either absence or presence of either buffer or 10 μM Naloxone for total and non-specific binding, respectively. Binding buffer contained Tris-HCl 50 mM, MgCl2 5 mM at pH 7.4. Plates were incubated at 27° C. for 60 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail.

Results:

As this invention is aimed at providing a compound or a chemically related series of compounds which act as dual ligands of the $\sigma_1$ receptor and the μ-opiod receptor it is a very preferred embodiment in which the compounds are selected which act as dual ligands of the $\sigma_1$ receptor and the μ-opiod receptor and especially compounds which have a binding expressed as K, which is preferably <1000 nM for both receptors, more preferably <500 nM, even more preferably <100 nM.

The following scale as been adopted for representing the binding to the the $\sigma_1$ receptor and the μ-opiod receptor expressed as $K_i$:
+ Both $K_i$-μ and $K_i$-$\sigma_1$>=500 nM
++ One K, <500 nM while the other K, is >=500 nM
+++ Both $K_i$-μ and $K_i$-$\sigma_1$<500 nM
++++ Both $K_i$-μ and $K_i$-$\sigma_1$<100 nM All compounds prepared in the present application exhibit binding to the $\sigma_1$ receptor and the μ-opiod receptor, in particular the following binding results are shown:

| EX | μ and $\sigma_1$ dual binding |
|---|---|
| 1 | ++++ |
| 2 | ++ |
| 3 | ++ |
| 4 | +++ |
| 5 | ++ |
| 6 | ++ |
| 7 | ++ |
| 8 | + |
| 9 | ++++ |
| 10 | +++ |
| 11 | +++ |
| 12 | +++ |
| 13 | +++ |
| 14 | ++++ |
| 15 | +++ |
| 16 | ++ |
| 17 | +++ |
| 18 | + |
| 19 | ++ |
| 20 | ++++ |
| 21 | ++ |
| 22 | ++ |
| 23 | ++ |
| 24 | + |
| 25 | +++ |
| 26 | ++++ |
| 27 | ++++ |
| 28 | +++ |
| 29 | +++ |
| 30 | ++++ |
| 31 | + |
| 32 | ++ |
| 33 | ++++ |
| 34 | +++ |
| 35 | ++ |
| 36 | ++++ |
| 37 | ++++ |
| 38 | +++ |

-continued

| EX | μ and σ₁ dual binding |
|----|----|
| 39 | ++++ |
| 40 | +++ |
| 41 | ++ |
| 42 | +++ |
| 43 | ++ |
| 44 | +++ |
| 45 | ++ |
| 46 | ++ |
| 47 | +++ |
| 48 | ++ |
| 49 | ++ |
| 50 | ++ |
| 51 | +++ |
| 52 | +++ |
| 53 | +++ |
| 54 | ++ |
| 55 | ++ |
| 56 | ++ |
| 57 | ++++ |
| 58 | ++ |
| 59 | ++ |
| 60 | +++ |
| 61 | ++ |
| 62 | +++ |
| 63 | + |
| 64 | ++ |
| 65 | ++ |
| 66 | ++ |
| 67 | ++ |
| 68 | ++ |
| 69 | ++ |
| 70 | +++ |
| 71 | +++ |
| 72 | ++ |
| 73 | +++ |

The invention claimed is:

1. A compound of Formula IV:

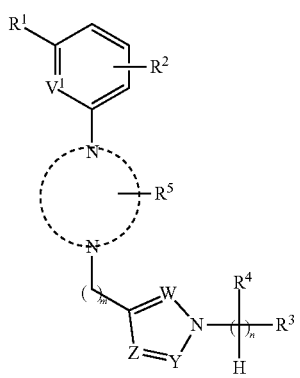

(IV)

wherein
m is 1 or 2;
n is 0 or 1;
$V^1$ is nitrogen or carbon;
$R^1$ is hydroxyl, —$NR^6R^7$, —$NR^6S(O)_2R^7$, —$NR^6COR^7$, —$NR^6CONR^7R^8$, —$SR^6$, —$S(O)_2R^6$, —$S(O)_2NR^6R^7$ or —$CONR^6R^7$;
$R^2$ is hydrogen, halogen, —$NR^6R^7$, —$SR^6$, —$OR^6$, substituted or unsubstituted alkyl, substituted or unsubstituted alkenyl or substituted or unsubstituted alkynyl;
  wherein the alkyl, alkenyl or alkynyl in $R^2$, if substituted, is substituted with one or more substituents selected from F, Cl, Br, I, $NH_2$, SH or OH, —C(O) OH, or —$OC_{1-4}$alkyl being unsubstituted or substituted by one or more of OH or halogen (F, Cl, I, Br);
$R^3$ is substituted or unsubstituted alkyl, $CONR^6R^7$, substituted or unsubstituted cycloalkyl, substituted or unsubstituted alkenyl, substituted or unsubstituted alkynyl, substituted or unsubstituted aryl or substituted or unsubstituted heterocyclyl;
$R^4$ is hydrogen, substituted or unsubstituted alkyl, substituted or unsubstituted cycloalkyl, substituted or unsubstituted alkenyl, substituted or unsubstituted alkynyl, substituted or unsubstituted aryl or substituted or unsubstituted heterocyclyl;
  wherein the aryl in $R^3$ and/or in $R^4$, if a substituted aryl, is substituted with one or more substituents selected from halogen (F, Cl, I, Br), —OH, —$NH_2$, —SH, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br);
  wherein the heterocyclyl or cycloalkyl in in $R^3$ and/or in $R^4$, if a substituted heterocyclyl or cycloalkyl, is substituted with one or more substituents selected from halogen (F, Cl, I, Br), —OH, —$NH_2$, —SH, =O, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br);
  wherein the alkyl, alkenyl or alkynyl in $R^3$ and/or in $R^4$, if substituted, is substituted with one or more substituents selected from F, Cl, Br, I, $NH_2$, SH or OH, —C(O)OH, or —$OC_{1-4}$alkyl being unsubstituted or substituted by one or more of OH or halogen (F, Cl, I, Br);
$R^5$ is hydrogen, hydroxy, or $CH_3$;
$R^6$, $R^7$ and $R^8$ are independent from each other and selected from the group consisting of hydrogen, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl;
  wherein the aryl in $R^6$, in $R^7$, and/or in $R^8$, if a substituted aryl, is substituted with one or more substituents selected from halogen (F, Cl, I, Br), —OH, —$NH_2$, —SH, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br);
  wherein the heterocyclyl or cycloalkyl in in $R^6$, in $R^7$, and/or in $R^8$, if a substituted heterocyclyl or cycloalkyl, is substituted with one or more substituents selected from halogen (F, Cl, I, Br), —OH, —$NH_2$, —SH, =O, —C(O)OH, —$OC_{1-4}$alkyl being unsubstituted or substituted by one or more of OH or halogen (F, Cl, I, Br), —CN, or —$C_{1-4}$alkyl being unsubstituted or substituted by one or more of OH or halogen (F, Cl, I, Br);
  wherein the alkyl, alkenyl or alkynyl in $R^6$, in $R^7$, and/or in $R^8$, if substituted, is substituted with one or more substituents selected from F, Cl, Br, I, $NH_2$, SH or OH, —C(O)OH, or —$OC_{1-4}$alkyl being unsubstituted or substituted by one or more of OH or halogen (F, Cl, I, Br);

and W, Y and Z are independently N or CH with only 1 or 2 of them being CH;
and wherein

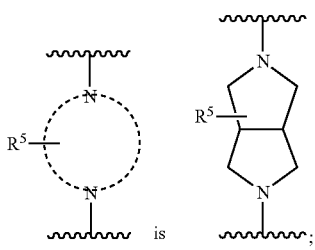

optionally as a stereoisomer, including enantiomers and diastereomers, a racemate or a mixture of at least two stereoisomers, including enantiomers and/or diastereomers, in any mixing ratio, or a salt thereof;
with the following proviso:
with the proviso that if $V^1$ is carbon, 2 of W, Y and Z are CH, n is 0 and $R^3$ is —CH$_3$ or C$_2$H$_5$, then $R^1$ may not be —NH$_2$.

2. The compound according to claim 1, wherein $R^3$ is CONR$^6$R$^7$, substituted or unsubstituted cycloalkyl, substituted or unsubstituted aryl or substituted or unsubstituted heterocyclyl.

3. The compound according to claim 2, wherein $R^3$ is substituted or unsubstituted cycloalkyl, substituted or unsubstituted aryl or substituted or unsubstituted heterocyclyl.

4. The compound according to claim 1, which is a compound of Formula V:

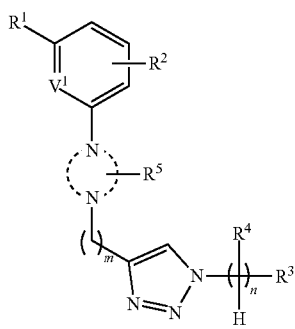

wherein
m is 1 or 2;
n is 0 or 1;
$V^1$ is nitrogen or carbon;
$R^1$ is hydroxyl, —NR$^6$R$^7$, —NR$^6$S(O)$_2$R$^7$, —NR$^6$COR$^7$, —NR$^6$CONR$^7$R$^8$, —SR$^6$, —S(O)$_2$R$^6$, —S(O)$_2$NR$^6$R$^7$ or —CONR$^6$R$^7$;
$R^2$ is hydrogen, halogen, —NR$^6$R$^7$, —SR$^6$, —OR$^6$, substituted or unsubstituted alkyl, substituted or unsubstituted alkenyl, or substituted or unsubstituted alkynyl;
$R^3$ is substituted or unsubstituted alkyl, CONR$^6$R$^7$, substituted or unsubstituted cycloalkyl, substituted or unsubstituted alkenyl, substituted or unsubstituted alkynyl, substituted or unsubstituted aryl or substituted or unsubstituted heterocyclyl;
$R^4$ is hydrogen, substituted or unsubstituted alkyl, substituted or unsubstituted cycloalkyl, substituted or unsubstituted alkenyl, substituted or unsubstituted alkynyl, substituted of unsubstituted aryl or substituted of unsubstituted heterocyclyl;
$R^5$ is hydrogen, hydroxy, or CH$_3$;
$R^6$, $R^7$ and $R^8$ are independent from each other and selected from the group consisting of hydrogen, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl;
and wherein

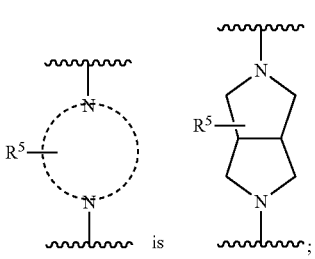

optionally as a stereoisomer, including enantiomers and diastereomers, a racemate or a mixture of at least two stereoisomers, including enantiomers and/or diastereomers, in any mixing ratio, or a salt thereof.

5. The compound according to claim 1, wherein
$R^1$ is hydroxyl, —NR$^6$R$^7$, —NR$^6$S(O)$_2$R$^7$, —SR$^6$, —S(O)$_2$R$^6$, or —S(O)$_2$NR$^6$R$^7$;
$R^2$ is hydrogen, halogen, —NR$^6$R$^7$, —SR$^6$, —OR$^6$, substituted or unsubstituted alkyl, substituted or unsubstituted alkenyl, or substituted or unsubstituted alkynyl, wherein
the alkyl is C$_{1-8}$alkyl;
the alkenyl is C$_{2-10}$-alkenyl;
the alkynyl is C$_{2-10}$-alkynyl;
the halogen is fluorine, chlorine, iodine or bromine;
$R^3$ is substituted or unsubstituted alkyl, CONR$^6$R$^7$, substituted or unsubstituted cycloalkyl, substituted or unsubstituted alkenyl, substituted or unsubstituted alkynyl, substituted or unsubstituted aryl or substituted or unsubstituted heterocyclyl, wherein
the aryl is phenyl, naphthyl or anthracene;
the heterocyclyl is a heterocyclic ring system of one or more saturated or unsaturated rings of which at least one ring contains one or more heteroatoms selected from the group consisting of nitrogen, oxygen and sulfur;
the alkyl is C$_{1-8}$alkyl;
the alkenyl is C$_{2-10}$-alkenyl;
the alkynyl is C$_{2-10}$-alkynyl;
the cycloalkyl is C$_{3-8}$cycloalkyl;
$R^4$ is hydrogen, substituted or unsubstituted alkyl, substituted or unsubstituted cycloalkyl, substituted or unsubstituted alkenyl, substituted or unsubstituted alkynyl, substituted or unsubstituted aryl or substituted or unsubstituted heterocyclyl, wherein
the aryl is phenyl, naphthyl or anthracene;
the heterocyclyl is a heterocyclic ring system of one or more saturated or unsaturated rings of which at least one ring contains one or more heteroatoms selected from the group consisting of nitrogen, oxygen and sulfur;

the alkyl is $C_{1-8}$alkyl;
the alkenyl is $C_{2-10}$-alkenyl;
the alkynyl is $C_{2-10}$-alkynyl;
the cycloalkyl is $C_{3-8}$cycloalkyl;
$R^5$ is hydrogen, hydroxy, or $CH_3$;
$R^6$, $R^7$ and $R^8$ are independent from each other and selected from the group consisting of hydrogen, substituted or unsubstituted alkyl, substituted or unsubstituted cycloalkyl, substituted or unsubstituted alkenyl, substituted or unsubstituted alkynyl, substituted or unsubstituted aryl and substituted or unsubstituted heterocyclyl, wherein
the aryl is phenyl, naphthyl or anthracene;
the heterocyclyl is a heterocyclic ring system of one or more saturated or unsaturated rings of which at least one ring contains one or more heteroatoms selected from the group consisting of nitrogen, oxygen and sulfur;
the alkyl is $C_{1-8}$alkyl;
the alkenyl is $C_{2-10}$-alkenyl;
the alkynyl is $C_{2-10}$-alkynyl;
the cycloalkyl is $C_{3-8}$cycloalkyl.

6. The compound according to claim 1, wherein
$R^1$ is hydroxyl, —$NR^6R^7$, —$NR^6S(O)_2R^7$, —$NR^6COR^7$, —$NR^6CONR^7R^8$, —$S(O)_2R^6$, —$S(O)_2NR^6R^7$, or —$CONR^6R^7$;
$R^2$ is hydrogen, fluorine, $CH_3$ or $CF_3$;
$R^3$ is substituted or unsubstituted propyl or butyl, diethylacetamide, substituted or unsubstituted cyclopentyl or cyclohexyl, substituted or unsubstituted phenyl, or substituted or unsubstituted pyridyl, imidazolyl, indenyl, 2,3-dihydroindenyl, benzofuryl, or pyrimidinyl;
$R^4$ is hydrogen, $CH_3$ or $CH_2OH$;
$R^5$ is hydrogen or $CH_3$; and
$R^6$, $R^7$, and $R^8$ are independently from each other selected from the group consisting of hydrogen, substituted or unsubstituted methyl, ethyl, propyl or butyl, substituted or unsubstituted phenyl, or substituted or unsubstituted pyrrolidinyl, or substituted or unsubstituted cyclopropyl.

7. The compound according to claim 1, wherein
m is 1 or 2;
n is 0 or 1;
$V^1$ is nitrogen or carbon;
$R^1$ is hydroxyl, —$NR^6R^7$, —$NR^6S(O)_2R^7$, —$NR^6COR^7$, —$NR^6CONR^7R^8$, —$S(O)_2R^6$, —$S(O)_2NR^6R^7$, or —$CONR^6R^7$;
$R^2$ is hydrogen, halogen, or $C_{1-4}$alkyl;
$R^3$ is selected from substituted or unsubstituted cycloalkyl, substituted or unsubstituted aryl, or substituted or unsubstituted heterocyclyl;
$R^4$ is hydrogen or substituted or unsubstituted $C_{1-4}$alkyl;
$R^5$ is hydrogen, hydroxy, or $CH_3$;
$R^6$, $R^7$, and $R^8$ are independently from each other selected from hydrogen, substituted or unsubstituted $C_{1-4}$alkyl, substituted or unsubstituted aryl, substituted or unsubstituted heterocyclyl, or substituted or unsubstituted cycloalkyl.

8. The compound according to claim 1, wherein
m is 1 or 2;
n is 0 or 1;
$V^1$ is nitrogen or carbon;
$R^1$ is hydroxyl, —$NR^6R^7$, —$NR^6S(O)_2R^7$, —$NR^6COR^7$, —$NR^6CONR^7R^8$, —$S(O)_2R^6$, —$S(O)_2NR^6R^7$, or —$CONR^6R^7$;
$R^2$ is hydrogen;
$R^3$ is substituted or unsubstituted cyclopentyl, cyclohexyl, substituted or unsubstituted phenyl, or substituted or unsubstituted pyridyl, imidazolyl, indenyl, 2,3-dihydroindenyl, benzofuryl, or pyrimidinyl;
$R^4$ is hydrogen or substituted or unsubstituted $C_{1-4}$alkyl;
$R^5$ is hydrogen, hydroxy, or $CH_3$;
$R^6$, $R^7$ and $R^8$ are independent from each other and selected from the group consisting of hydrogen, substituted or unsubstituted $C_{1-4}$alkyl, substituted or unsubstituted $C_{3-6}$cycloalkyl, and substituted or unsubstituted phenyl;
and W, Y and Z are independently from one another N or CH with only 1 or 2 of them being CH;
and wherein

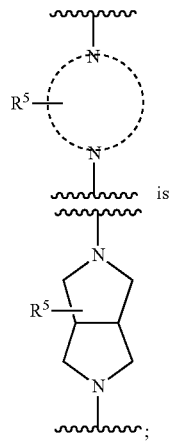

optionally as a stereoisomer, including enantiomers and diastereomers, a racemate or a mixture of at least two stereoisomers, including enantiomers and/or diastereomers, in any mixing ratio, or a salt thereof.

9. The compound according to claim 1 which is selected from:
N-(3-(5-((1-phenyl-1H-1,2,3-triazol-4-yl)methyphexahydropyrrolo[3,4-c]pyrrol-2(1H)-yl)phenyl)methanesulfonamide,
N-(3-(5-((1-phenyl-1H-1,2,3-triazol-4-yl)methyphexahydropyrrolo[3,4-c]pyrrol-2(1H)-yl)phenyl)propane-2-sulfonamide,
N-(6-(5-((1-phenyl-1H-1,2,3-triazol-4-yl)methyphexahydropyrrolo[3,4-c]pyrrol-2(1H)-yl)pyridin-2-yl)propane-2-sulfonamide,
N-(6-(5-((1-benzyl-1H-1,2,3-triazol-4-yl)methyphexahydropyrrolo[3,4-c]pyrrol-2(1H)-yl)pyridin-2-yl)propane-2-sulfonamide,
N-(6-(5-((1-(pyridin-2-ylmethyl)-1H-1,2,3-triazol-4-yl)methyl)hexahydropyrrolo[3,4-c]pyrrol-2(1H)-yl)pyridin-2-yl)propane-2-sulfonamide, and
N-(6-(5-((1-(2-fluorophenyl)-1H-1,2,3-triazol-4-yl)methyphexahydropyrrolo[3,4-c]pyrrol-2(1H)-yl)pyridin-2-yl)propane-2-sulfonamide, optionally as a stereoisomer, including enantiomers and diastereomers, a racemate or a mixture of at least two stereoisomers, including enantiomers and/or diastereomers, in any mixing ratio, or a salt thereof.

10. A process for the production of a compound of formula V according to claim 4

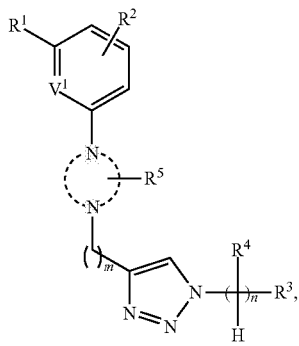

wherein $R^1$, $R^2$, $R^3$, $R^4$, $R^5$, n and m as well as

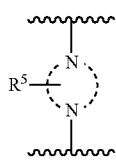

are as defined in claim 4,
wherein a compound of formula VIII or its suitable salt,

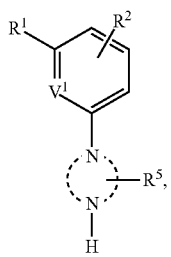

wherein $R^1 R^2$ and $R^5$ are as defined in claim 4, is reacted with a compound of formula X under the conditions of Step 2

wherein m is as defined in claim 4, leading to a compound of formula IX,

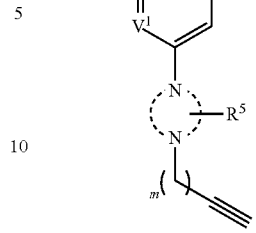

wherein $R^1$, $R^2$, $R^5$ and m are as defined in claim 4,
followed by reacting the compound of formula IX with a compound of formula XI under the conditions of Step 3

wherein $R^3$, $R^4$ and n are as defined in claim 4, under the conditions of Step 3, leading to a compound of formula (V),
wherein X is a leaving group,
wherein the reaction of Step 2 of the compounds of formula (VIII) with the compounds of formula (X) is carried out in the presence of a base in an aprotic solvent,
wherein the reaction of Step 3 of the compounds of formula (IX) with the compounds of formula (XI) is carried out in the presence of a copper salt and sodium ascorbate in a mixture of protic organic solvent and water.

11. A pharmaceutical composition which comprises the compound according to claim 1 or a pharmaceutically acceptable salt thereof, and a pharmaceutically acceptable carrier, adjuvant or vehicle.

12. A method for treating pain in a subject in need thereof, comprising administration of an effective amount of the compound according to claim 1.

13. The method of claim 12, wherein the pain is medium to severe pain, visceral pain, chronic pain, cancer pain, migraine, inflammatory pain, acute pain or neuropathic pain, allodynia or hyperalgesia.

* * * * *

UNITED STATES PATENT AND TRADEMARK OFFICE
CERTIFICATE OF CORRECTION

PATENT NO. : 10,745,361 B2
APPLICATION NO. : 16/426024
DATED : August 18, 2020
INVENTOR(S) : Félix Cuevas-Cordobés, Carmen Almansa-Rosales and Monica Garcia-Lopez Page 1 of 1

It is certified that error appears in the above-identified patent and that said Letters Patent is hereby corrected as shown below:

In the Claims

Column 130, Line 46: "methyphexahy-" should read -- methyl)hexahy- --.
Line 29: "methyphexahy-" should read -- methyl)hexahy- --.
Line 52: "methyphexahy-" should read -- methyl)hexahy- --.
Line 59: "hyphexahydropyrrolo" should read -- hyl)hexahydropyrrolo --.

Signed and Sealed this
Third Day of November, 2020

Andrei Iancu
*Director of the United States Patent and Trademark Office*